United States Patent
Tiden et al.

(10) Patent No.: US 8,026,244 B2
(45) Date of Patent: Sep. 27, 2011

(54) THIOXANTHINE DERIVATIVES AND THEIR USE AS INHIBITORS OF MPO

(75) Inventors: Anna-Karin Tiden, Sodertalje (SE); Jenny Viklund, Sodertalje (SE)

(73) Assignee: AstraZeneca AB, Södertälje (SE)

( * ) Notice: Subject to any disclaimer, the term of this patent is extended or adjusted under 35 U.S.C. 154(b) by 341 days.

(21) Appl. No.: 12/295,306

(22) PCT Filed: Apr. 12, 2007

(86) PCT No.: PCT/SE2007/000349
§ 371 (c)(1),
(2), (4) Date: Sep. 30, 2008

(87) PCT Pub. No.: WO2007/120098
PCT Pub. Date: Oct. 25, 2007

(65) Prior Publication Data
US 2009/0149475 A1    Jun. 11, 2009

Related U.S. Application Data

(60) Provisional application No. 60/791,667, filed on Apr. 13, 2006.

(51) Int. Cl.
| | |
|---|---|
| *C07D 473/22* | (2006.01) |
| *A61K 31/522* | (2006.01) |
| *A61P 9/10* | (2006.01) |
| *A61P 11/00* | (2006.01) |
| *A61P 11/08* | (2006.01) |
| *A61P 25/16* | (2006.01) |
| *C07D 401/06* | (2006.01) |
| *C07D 401/12* | (2006.01) |
| *C07D 403/06* | (2006.01) |
| *C07D 403/12* | (2006.01) |

(52) U.S. Cl. ............ 514/263.2; 514/263.21; 514/263.22; 544/268; 544/269; 544/270; 544/296; 544/310

(58) Field of Classification Search ............... 514/263.2, 514/263.22, 263.21; 544/268, 269, 270
See application file for complete search history.

(56) References Cited

U.S. PATENT DOCUMENTS

| | | | | |
|---|---|---|---|---|
| 5,708,009 | A * | 1/1998 | Glasebrook | 514/324 |
| 6,780,865 | B1 * | 8/2004 | Porubek et al. | 514/263.2 |
| 7,425,560 | B2 * | 9/2008 | Tiden | 514/263.34 |
| 2007/0032468 | A1 * | 2/2007 | Kettle et al. | 514/210.21 |
| 2008/0221133 | A1 * | 9/2008 | Tiden | 514/263.34 |
| 2009/0054468 | A1 * | 2/2009 | Eriksson et al. | 514/263.21 |
| 2009/0286813 | A1 * | 11/2009 | Pivonka et al. | 514/263.2 |

* cited by examiner

*Primary Examiner* — Mark Berch

(57) ABSTRACT

There are disclosed novel compounds of Formula (I) wherein L, R¹, X and Y are as defined in the specification, and pharmaceutically acceptable salts thereof; together with processes for their preparation, compositions containing them and their use in therapy. The compounds are inhibitors of the enzyme MPO and are thereby particularly useful in the treatment or prophylaxis of neuroinflammatory disorders, cardio- and cerebrovascular atherosclerotic disorders and peripheral artery disease and respiratory disorders.

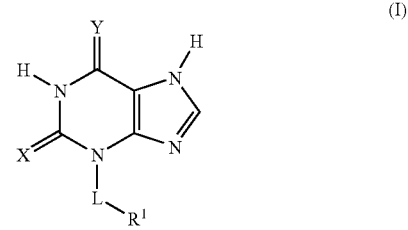

7 Claims, No Drawings

THIOXANTHINE DERIVATIVES AND THEIR USE AS INHIBITORS OF MPO

CROSS-REFERENCE TO RELATED APPLICATIONS

This application is a US National Stage under 35 U.S.C. §371 of International Application No. PCT/SE2007/000349, filed 12 Apr. 2007, which claims priority under 35 U.S.C. §119(e) to U.S. Provisional Application No. 60/791,667, filed 13 Apr. 2006, which is hereby incorporated herein by reference.

FIELD OF THE INVENTION

The present invention relates to novel thioxanthine derivatives, processes for their preparation, compositions containing them and their use in therapy.

BACKGROUND OF THE INVENTION

Myeloperoxidase (MPO) is a heme-containing enzyme found predominantly in polymorphonuclear leukocytes (PMNs). MPO is one member of a diverse protein family of mammalian peroxidases that also includes eosinophil peroxidase, thyroid peroxidase, salivary peroxidase, lactoperoxidase, prostaglandin H synthase, and others. The mature enzyme is a dimer of identical halves. Each half molecule contains a covalently bound heme that exhibits unusual spectral properties responsible for the characteristic green colour of MPO. Cleavage of the disulphide bridge linking the two halves of MPO yields the hemi-enzyme that exhibits spectral and catalytic properties indistinguishable from those of the intact enzyme. The enzyme uses hydrogen peroxide to oxidize chloride to hypochlorous acid. Other halides and pseudohalides (like thiocyanate) are also physiological substrates to MPO.

PMNs are of particular importance for combating infections. These cells contain MPO, with well-documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound. Hypochlorous acid is oxidizing in itself, and reacts most avidly with thiols and thioethers, but also converts amines into chloramines, and chlorinates aromatic amino acids. Macrophages are large phagocytic cells which, like PMNs, are capable of phagocytosing microorganisms. Macrophages can generate hydrogen peroxide and upon activation also produce myeloperoxidase. MPO and hydrogen peroxide can also be released to the outside of the cells where the reaction with chloride can induce damage to adjacent tissue.

Linkage of myeloperoxidase activity to disease has been implicated in neurological diseases with a neuroinflammatory response including multiple sclerosis, Alzheimer's disease, Parkinson's disease and stroke as well as other inflammatory diseases or conditions like asthma, chronic obstructive pulmonary disease, cystic fibrosis, atherosclerosis, ischemic heart disease, heart failure, inflammatory bowel disease, renal glomerular damage and rheumatoid arthritis. Lung cancer has also been suggested to be associated with high MPO levels.

Multiple Sclerosis (MS)

MPO positive cells are immensely present in the circulation and in tissue undergoing inflammation. More specifically MPO containing macrophages and microglia has been documented in the CNS during disease; multiple sclerosis (Nagra R M, et al. Journal of Neuroimmunology 1997; 78(1-2):97-107), Parkinson's disease (Choi D-K. et al. J. Neurosci. 2005; 25(28):6594-600) and Alzheimer's disease (Green P S. et al. Journal of Neurochemistry. 2004; 90(3):724-33). It is supposed that some aspects of a chronic ongoing inflammation result in an overwhelming destruction where agents from MPO reactions have an important role.

The enzyme is released both extracellularly as well as into phagolysosomes in the neutrophils (Hampton M B, Kettle A J, Winterbourn C C. Blood 1998; 92(9): 3007-17). A prerequisite for the MPO activity is the presence of hydrogen peroxide, generated by NADPH oxidase and a subsequent superoxide dismutation. The oxidized enzyme is capable to use a plethora of different substrates of which chloride is most recognized. From this reaction the strong non-radical oxidant—hypochlorous acid (HOCl)— is formed. HOCl oxidizes sulphur containing amino acids like cysteine and methionine very efficiently (Peskin A V, Winterbourn C C. Free Radical Biology and Medicine 2001; 30(5): 572-9). It also forms chloramines with amino groups, both in proteins and other biomolecules (Peskin A V. et al. Free Radical Biology and Medicine 2004; 37(10):1622-30). It chlorinates phenols (like tyrosine) (Hazen S L. et al. Mass Free Radical Biology and Medicine 1997; 23(6): 909-16) and unsaturated bonds in lipids (Albert C J. et al. J. Biol. Chem. 2001; 276 (26): 23733-41), oxidizes iron centers (Rosen H, Klebanoff S J. Journal of Biological Chemistry 1982; 257(22): 13731-354) and crosslinks proteins (Fu X, Mueller D M, Heinecke J W. Biochemistry 2002; 41(4): 1293-301).

Proteolytic cascades participate both in cell infiltration through the BBB as well as the destruction of BBB, myelin and nerve cells (Cuzner M L, Opdenakker G. Journal of Neuroimmunology 1999; 94(1-2): 1-14; Yong V W. et al. Nature Reviews Neuroscience 2001; 2(7):5 02-11). Activation of matrix metalloproteinases (MMPs) can be accomplished through the action of upstream proteases in a cascade as well as through oxidation of a disulfide bridge Fu X. et al. J. Biol. Chem. 2001; 276(44): 41279-87; Gu Z. et al. Science 2002; 297(5584): 1186-90). This oxidation can be either a nitrosylation or HOCl-mediated oxidation. Both reactions can be a consequence of MPO activity. Several reports have suggested a role for MMP's in general and MMP-9 in particular as influencing cell infiltration as well as tissue damage (BBB breakdown and demyelination), both in MS and EAE (for review see Yong V W. et al, supra). The importance of these is specific kinds of mechanisms in MS comes from studies where increased activity and presence of proteases have been identified in MS brain tissue and CSF. Supportive data has also been generated by doing EAE studies with mice deficient in some of the proteases implicated to participate in the MS pathology, or by using pharmacological approaches.

The demyelination is supposed to be dependent on the cytotoxic T-cells and toxic products generated by activated phagocytes (Lassmann H. J Neurol Neurosurg Psychiatry 2003; 74(6): 695-7). The axonal loss is thus influenced by proteases and reactive oxygen and nitrogen intermediates. When MPO is present it will obviously have the capability of both activating proteases (directly as well as through disinhibition by influencing protease inhibitors) and generating reactive species.

Chronic Obstructive Pulmonary Disease (COPD)

Chronic obstructive pulmonary disease (COPD) is a disease state characterised by airflow limitation that is not fully reversible. The airflow limitation is usually both progressive and associated with an abnormal inflammatory response of the lungs to noxious particles or gases. COPD is a major public health problem. It is the fourth leading cause of chronic morbidity and mortality in the United States and is projected to rank fifth in 2020 as a worldwide burden of disease. In the UK the prevalence of COPD is 1.7% in men and 1.4% in women. COPD spans a range of severity from mild to very severe, with the cost of treatment rising rapidly as the severity increases.

Levels of MPO in sputum and BAL are much greater in COPD patients than normal, non-smoking controls (Keatings V. M., Barnes P. J. Am. J Respir Crit. Care Med 1997; 155: 449-453; Pesci, A. et al. Eur Respir J 1998; 12:380-386). MPO levels are further elevated during exacerbations of the disease (Fiorini G. et al. Biomedicine & Pharmacotherapy 2000; 54:274-278; Crooks S. W. et al. European Respiratory Journal. 15(2): 274-80, 2000). The role of MPO is likely to be more important in exacerbations of COPD (Sharon S. D. et al. Am J Respir Crit. Care Med. 2001; 163: 349-355).

In addition to the destructive capacity of MPO there is a strong clinical link with vascular disease (Baldus S. et al. Circulation 2003; 108: 1440-5). Dysfunctional MPO polymorphisms are associated with a reduced risk of mortality from coronary artery disease (Nikpoor B. et al. Am Heart J 2001; 142: 336), and patients with high serum levels of MPO have increased risk of acute coronary syndrome. The effects of MPO on vascular disease may extend to COPD, since there is strong evidence that the pulmonary vasculature is one of the earliest sites of involvement in the smokers' lung. Striking changes in the intima of the pulmonary arteries have been described which show a dose relationship with smoking (Hale K. A., Niewoehner D. E., Cosio M. G. Am Rev Resp Dis 1980; 122: 273-8). The physiological function of MPO is associated with innate host defense. This role, however, is not critical as most cases of MPO deficient patients have relatively benign symptoms (Parry M. F. et al. Ann Int Med. 1981; 95: 293-301, Yang, K. D., Hill, H. R. Pediatr Infect Dis J. 2001; 20: 889-900). In summary, there is considerable evidence that elevated MPO levels in COPD may contribute to the disease via several mechanisms. A selective inhibitor of MPO would therefore be expected to alleviate both the acute and chronic inflammatory aspects of COPD and may reduce the development of emphysema.

Atherosclerosis

An MPO inhibitor should reduce the atherosclerotic burden and/or the vulnerability of existing atherosclerotic lesions and thereby decrease the risk of acute myocardial infarction, unstable angina or stroke, and reduce ischemia/reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al. (1994) J Clin Invest 94(1): 437-44). In eroded and ruptured human lesions, as compared to fatty streaks, an increased number of MPO expressing macrophages have been demonstrated, suggesting a particular role for MPO in acute coronary syndromes (Sugiyama, S. et al. (2001) Am J Pathol 158(3): 879-91). Patients with established coronary artery disease have higher plasma and leukocyte MPO levels than healthy controls (Zhang, R. et al. (2001) Jama 286(17): 2136-42). Moreover, in two large prospective studies plasma levels of MPO predicted the risk of future coronary events or revascularisation (Baldus, S. et al. (2003) Circulation 108(12): 1440-5; Brennan, M. et al. (2003) N Engl J Med 349(17): 1595-604). Total MPO deficiency in humans has a prevalece prevalence of 1 in 2000-4000 individuals. These individuals appear principally healthy but a few cases of severe Candida infection have been reported. Interestingly, MPO deficient humans are less affected by cardiovascular disease than controls with normal MPO levels (Kutter, D. et al. (2000) Acta Haematol 104(1)). A polymorphism in the MPO promoter affects expression leading to high and low MPO expressing individuals. In three different studies the high expression genotype has been associated with an increased risk of cardiovascular disease (Nikpoor, B. et al. (2001) Am Heart J 142(2): 336-9; Makela, R., P. J. Karhunen, et al. (2003) Lab Invest 83(7): 919-25; Asselbergs, F. W., et al. (2004) Am J Med 116(6): 429-30). Data accumulated during the last ten years indicate that the proatherogenic actions of MPO include oxidation of lipoproteins, induction of endothelial dysfunction via consuming nitric oxide and destabilisation of atherosclerotic lesions by activation of proteases (Nicholls, S. J. and S. L. Hazen (2005) Arterioscler Thromb Vasc Biol 25(6): 1102-11). Recently, several studies have focused on nitro- and chlorotyrosine modifications of LDL and HDL lipoproteins. Since chlorotyrosine modifications in vivo only can be generated by hypochlorus acid produced by MPO these modifications are regarded as specific markers of MPO activity (Hazen, S. L. and J. W. Heinecke (1997) J Clin Invest 99(9): 2075-81). LDL particles exposed to MPO in vitro become aggregated, leading to facilitated uptake via macrophage scavenger receptors and foam cell formation (Hazell, L. J. and R. Stocker (1993) Biochem J 290 (Pt 1): 165-72). Chlorotyrosine modification of apoA1, the main apolipoprotein of HDL cholesterol, results in impaired cholesterol acceptor function (Bergt, C., S. et al. (2004) Proc Natl Acad Sci USA; Zheng, L. et al. (2004) J Clin Invest 114(4): 529-41). Systematic studies of these mechanisms have shown that MPO binds to and travels with apoA1 in plasma. Moreover, MPO specifically targets those tyrosine residues of apoA1 that physically interact with the macrophage ABCA1 cassette transporter during cholesterol efflux from the macrophage (Bergt, C. et al. (2004) J Biol Chem 279(9): 7856-66; Shao, B. et al. (2005) J Biol Chem 280(7): 5983-93; Zheng et al. (2005) J Biol Chem 280(1): 38-47). Thus, MPO seems to have a dual aggravating role in atherosclerotic lesions, i.e. increasing lipid accumulation via aggregation of LDL particles and decreasing the reverse cholesterol transport via attack on the HDL protein apoA1.

The present invention discloses novel thioxanthines that surprisingly display useful properties as inhibitors of the enzyme MPO. Furthermore, the novel compounds of the present invention display either one or more than one of the following: (i) improved selectivity towards TPO; (ii) unexpectedly high inhibitory activity towards MPO; (iii) improved brain permeability; (iv) improved solubility and/or (v) improved half-life; when compared to known thioxanthines. Such thioxanthines are disclosed in e.g. WO 03/089430 and WO 05/037835.

DISCLOSURE OF THE PRESENT INVENTION

The present invention relates to a compound of Formula (I)

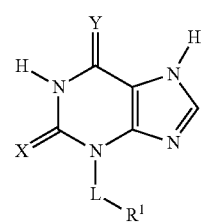

I wherein
at least one of X and Y represents S, and the other represents O or S;
L represents $(R^{12})_p$-Q-$(CR^{13}R^{14})_r$; wherein $(R^{12})_p$ and $(CR^{13}R^{14})_r$ each optionally contain one or two double or triple bonds;
wherein Q is O, S(O)$_n$, $NR^6$, $NR^6C(O)$, $C(O)NR^6$, or a bond;
wherein $R^{12}$ is selected from C1 to 6 alkyl or C1 to 6 alkoxy, said C1 to 6 alkyl or said C1 to 6 alkoxy is optionally substituted with OH, halogen, $CF_3$, $CHF_2$, $CFH_2$, CN, $NR^4R^5$, phenoxy or aryl; and wherein said phenoxy is optionally substituted with C1 to 6 alkyl, halogen or C1 to 6 alkoxy; and wherein said phenoxy optionally incorporates a carbonyl adjacent to the oxygen; and wherein said C1 to 6 alkoxy optionally incorporates a carbonyl is adjacent to the oxygen;
wherein $R^{13}$ and $R^{14}$ are independently selected from hydrogen, OH, halogen, $CF_3$, $CHF_2$, $CFH_2$, CN, $NR^4R^5$, C1 to 6 alkyl, phenoxy and C1 to 6 alkoxy; wherein said phenoxy or C1 to 6 alkoxy optionally incorporates a carbonyl adjacent to the oxygen; and wherein said phenoxy is optionally substituted with C1 to 6 alkyl, halogen or C1 to 6 alkoxy;
wherein p represents an integer 0, 1, 2, 3 or 4 and r represents an integer 0, 1, 2, 3 or 4; and
wherein $1 \leq p+r \leq 7$;
$R^1$ represents a mono- or bicyclic heteroaromatic ring system containing one or more heteroatoms selected from N, O and S; wherein said mono- or bicyclic heteroaromatic ring system is optionally fused with one or two 5- or 6-membered saturated or partially saturated ring(s) containing one or more atoms selected from C, N, O and S, wherein said mono- or bicyclic heteroaromatic ring system alone or when fused with one or two 5- or 6-membered saturated or partially saturated ring(s) is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O or S, and a mono- or bicyclic heteroaromatic ring system containing one or more heteroatoms selected from N, S or O; and wherein said C1 to 7 alkoxy is optionally substituted with C1 to 6 alkoxy or aryl; and wherein said C1 to 7 alkoxy or said phenoxy is optionally incorporating a carbonyl adjacent to the oxygen; and wherein said C1 to 7 alkyl is optionally substituted with hydroxy or C1 to 6 alkoxy; and wherein said C1 to 7 alkyl is optionally incorporating a carbonyl at any position in the C1 to 7 alkyl; and wherein said phenoxy is optionally substituted with C1 to 6 alkyl, halogen or C1 to 6 alkoxy;
at each occurrence, $R^2$, $R^3$, $R^4$, $R^5$, $R^6$, $R^1$ and $R^{10}$ are independently selected from hydrogen, C1 to 6 alkyl, C1 to 6 alkoxy, aryl and phenoxy; said C1 to 6 alkoxy or phenoxy is optionally incorporating a carbonyl adjacent to the oxygen; and said C1 to 6 alkyl is optionally substituted with halogen, C1 to 6 alkoxy, CHO, C2 to 6 alkanoyl, OH, $C(O)NR^7R^8$ or $NR^7C(O)R^8$; and said aryl or said phenoxy is optionally substituted with C1 to 6 alkyl, halogen or C1 to 6 alkoxy;
or the groups $NR^2R^3$, $NR^4R^5$ and $NR^9R^{10}$ each independently represents a 5 to 7 membered saturated azacyclic ring optionally incorporating one additional heteroatom selected from O, S and $NR^{11}$, said ring being optionally further substituted with halogen, C1 to 6 alkoxy, CHO, C2 to 6 alkanoyl, OH, $C(O)NR^7R^8$ or $NR^7C(O)R^8$;
at each occurrence $R^7$, $R^3$ and $R^{11}$ independently represent hydrogen or C1 to 6 alkyl, or the group $NR^7R^8$ represents a 5 to 7 membered saturated azacyclic ring optionally incorporating one additional heteroatom selected from O, S and $NR^{11}$;
n represents an integer 0, 1 or 2;
with the proviso that for $R^1$ thienyl or furyl is excluded;
and with the proviso that when Q is O, S(O)$_n$, $NR^6$, $NR^6C(O)$ or $C(O)NR^6$, then p is greater or equal to 1;
as a pharmaceutically acceptable salt, solvate or solvate of a salt thereof.

One aspect of the present invention relates to a compound according to Formula (I)

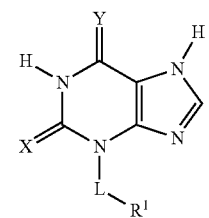

I wherein
at least one of X and Y represents S, and the other represents O or S;
L represents $(R^{12})_p$-Q-$(CR^{13}R^{14})_r$; wherein $(R^{12})_p$ and $(CR^{13}R^{14})_r$ each optionally contain one or two double or triple bonds;
wherein Q is O, S(O)$_n$, $NR^6$, $NR^6C(O)$, $C(O)NR^6$, or a bond;
wherein $R^{12}$ is selected from C1 to 6 alkyl or C1 to 6 alkoxy, said C1 to 6 alkyl or said C1 to 6 alkoxy is optionally substituted with OH, halogen, $CF_3$, $CHF_2$, $CFH_2$, CN, $NR^4R^5$, phenoxy or aryl; and wherein said phenoxy is optionally substituted with C1 to 6 alkyl, halogen or C1 to 6 alkoxy; and wherein said phenoxy optionally incorporates a carbonyl adjacent to the oxygen; and wherein C1 to 6 alkoxy optionally incorporates a carbonyl adjacent to the oxygen
wherein $R^{13}$ and $R^{14}$ are independently selected from hydrogen, OH, halogen, $CF_3$, $CHF_2$, $CFH_2$, CN, $NR^4R^5$, C1 to 6 alkyl, phenoxy and C1 to 6 alkoxy, said phenoxy or C1 to 6 alkoxy optionally incorporates a carbonyl adjacent to the oxygen; and said phenoxy is optionally substituted with C1 to 6 alkyl, halogen or C1 to 6 alkoxy;
wherein p represents an integer 0, 1, 2, 3 or 4 and r represents an integer 0, 1, 2, 3 or 4; and wherein $1 \leq p+r \leq 7$;
$R^1$ represents a mono- or bicyclic heteroaromatic ring system containing one or more heteroatoms selected from N, O and S; wherein said mono- or bicyclic heteroaromatic ring system is optionally fused with one or two 5- or 6-membered saturated or partially saturated ring(s) containing one or more atoms selected from C, N, O and S, wherein said mono- or bicyclic heteroaromatic ring system alone or when fused with one or two 5- or 6-membered saturated or partially saturated ring(s) is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, CN, $C(O)NR^2R^3$, $NR^2C(O)R^3$, $C(O)R^3$, a 5- or 6-membered saturated or partially saturated ring containing one or more atoms selected from C, N, O or S, and a 5- or 6-membered heteroaromatic ring containing one or more heteroatoms selected from N, S or O; and wherein said C1 to 7 alkoxy is optionally substituted with C1 to 6 alkoxy or aryl; and wherein said C1 to 7 alkoxy or said phenoxy is optionally incorporating a carbonyl adjacent to the oxygen; and wherein said C1 to 7 alkyl is optionally substituted with hydroxy or C1 to 6 alkoxy; and wherein said C1 to 7 alkyl is optionally incorporating a carbonyl at any position in the C1 to 7 alkyl; and wherein said phenoxy is optionally substituted with C1 to 6 alkyl, halogen or C1 to 6 alkoxy;

at each occurrence, $R^2$, $R^3$, $R^4$, $R^5$, $R^6$, $R^9$ and $R^{10}$ are independently selected from hydrogen, C1 to 6 alkyl, C1 to 6 alkoxy, aryl and phenoxy; said C1 to 6 alkoxy or phenoxy is optionally incorporating a carbonyl adjacent to the oxygen; and said C1 to 6 alkyl is optionally substituted with halogen, C1 to 6 alkoxy, CHO, C2 to 6 alkanoyl, OH, $C(O)NR^7R^8$ or $NR^7C(O)R^8$; and said aryl or said phenoxy is optionally substituted with C1 to 6 alkyl, halogen or C1 to 6 alkoxy;

or the groups $NR^2R^3$, $NR^4R^5$ and $NR^9R^{10}$ each independently represents a 5 to 7 membered saturated azacyclic ring optionally incorporating one additional heteroatom selected from O, S and $NR^{11}$, said ring being optionally further substituted with halogen, C1 to 6 alkoxy, CHO, C2 to 6 alkanoyl, OH, $C(O)NR^7R^8$ or $NR^7C(O)R^8$;

at each occurrence $R^7$, $R^8$ and $R^{11}$ independently represent hydrogen or C1 to 6 alkyl, or the group $NR^7R^8$ represents a 5 to 7 membered saturated azacyclic ring optionally incorporating one additional heteroatom selected from O, S and $NR^{11}$;

n represents an integer 0, 1 or 2;

with the proviso that for $R^1$ thienyl or furyl is excluded;

and with the proviso that when Q is O, $S(O)_n$, $NR^6$, $NR^6C(O)$ or $C(O)NR^6$, then p is greater or equal to 1;

as a pharmaceutically acceptable salt, solvate or solvate of a salt thereof.

According to one aspect of the present invention, X represents S and Y represents O.

According to another aspect of the present invention, p is 1 or 2.

According to one aspect of the present invention, $R^{12}$ is C1 to 6 alkyl, optionally substituted with OH, halogen, $CF_3$, $CHF_2$, $CFH_2$, CN, $NR^4R^5$, phenoxy or aryl. According to another embodiment of the present invention, $R^{12}$ is C1 to 6 alkyl. According to another embodiment of the present invention, said alkyl is substituted with OH, halogen, $CF_3$, phenoxy or aryl. According to a further embodiment of the present invention, said alkyl is substituted with aryl or phenoxy. According to yet a further embodiment of the present invention, said aryl is phenyl.

According to other aspects of the present invention, $R^{12}$ is C3 alkyl, C2 alkyl or C1 alkyl.

According to one aspect of the present invention, r is 0 or 1.

According to one aspect of the present invention, Q is $NR^6$ or a bond. According to one embodiment of the present invention, $R^6$ is hydrogen or C1 to 6 alkyl. According to another embodiment of the present invention, said alkyl is C1 to 3 alkyl.

According to one aspect of the present invention, Q is $NR^6C(O)$. According to one embodiment of the present invention, $R^6$ is hydrogen.

According to one aspect of the present invention, $R^{13}$ and $R^{14}$ are independently selected from hydrogen, OH, halogen, $CF_3$, CN, $NR^4R^5$, C1 to 6 allyl, phenoxy and C1 to 6 alkoxy and said phenoxy is optionally substituted with C1 to 6 alkyl, halogen or C1 to 6 alkoxy.

According to one embodiment of the present invention, $R^{13}$ and $R^{14}$ are hydrogen.

According to one aspect of the present invention Q is O.

According to one aspect of the present invention, L represents ethyl, methyl, —$CH_2CH(CH_3)OCH_2$—, —$CH_2CH(C_6H_5)$—, —$CH_2CH_2NHCH_2$—, —$CH_2CH_2N(CH_3)CH_2$—, —$CH_2CH(CH_3)NHCH_2$—, or —$CH_2CH(CH_3)NHC(O)$—.

According to one aspect of the present invention, $R^1$ represents a mono- or bicyclic heteroaromatic ring system containing one or more heteroatoms selected from N, O and S; wherein said mono- or bicyclic heteroaromatic ring system is optionally fused with one or two 5- or 6-membered saturated or partially saturated ring(s) containing one or more atoms selected from C, N, O and S, wherein said mono- or bicyclic heteroaromatic ring system alone or when fused with one or two 5- or 6-membered saturated or partially saturated ring(s) is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said C1 to 7 alkoxy or said phenoxy is optionally incorporating a carbonyl adjacent to the oxygen; and wherein said C1 to 7 alkyl is optionally substituted with hydroxy or C1 to 6 alkoxy; and wherein said C1 to 7 alkyl is optionally incorporating a carbonyl at any position in the C1 to 7 alkyl; and wherein said phenoxy is optionally substituted with C1 to 6 alkyl, halogen or C1 to 6 alkoxy.

According to one embodiment of the present invention, $R^1$ represents a mono- or bicyclic heteroaromatic ring system containing one or more heteroatoms selected from N, O and S; wherein said mono- or bicyclic heteroaromatic ring system is optionally fused with one 5- or 6-membered saturated or partially saturated ring containing one or more atoms selected from C, N, O and S, wherein said mono- or bicyclic heteroaromatic ring system alone or when fused with one or two 5- or 6-membered saturated or partially saturated ring(s) is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, CN, $C(O)NR^2R^3$, $NR^2C(O)R^3$, $C(O)R^3$, a 5- or 6-membered saturated ring containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to one embodiment of the present invention, said mono- or bicyclic heteroaromatic ring system containing one or more heteroatoms selected from N, O and S, optionally fused with one 5- or 6-membered saturated or partially saturated ring contains one or two nitrogen atoms.

According one embodiment of the present invention, said mono- or bicyclic heteroaromatic ring system containing one or more heteroatoms selected from N, O and S, optionally fused with one 5- or 6-membered saturated or partially saturated ring contains one oxygen atom.

According one embodiment of the present invention, said mono- or bicyclic heteroaromatic ring system containing one or more heteroatoms selected from N, O and S, optionally fused with one 5- or 6-membered saturated or partially saturated ring contains 3 nitrogen atoms.

According to one embodiment of the present invention, $R^1$ represents a bicyclic heteroaromatic ring system containing one or more heteroatoms selected from N, O and S; wherein said bicyclic heteroaromatic ring system is optionally substituted with one or more substituents independently selected from halogen, $CF_3$, $SO_{(n)}R^9$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to another embodiment of the present invention, said bicyclic heteroaromatic ring system is unsubstituted.

According to another embodiment of the present invention, said bicyclic heteroaromatic ring system is substituted with one or more substituents independently selected from halogen, $CF_3$, $SO_{(n)}R^9$, $(CH_2)_nR^3$, $NR^4R^5$, C1 to 7 allyl, C1 to 7 alkoxy, phenoxy, aryl, $C(O)R^3$, a 5- or 6-membered saturated containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to another embodiment of the present invention, said bicyclic heteroaromatic ring system is substituted with one or more substituents independently selected from halogen, $CF_3$, $SO_{(n)}R^9$, $(CH_2)_nR^3$, $NR^4R^5$, C1 to 7 alkyl, C1 to 7 alkoxy, phenoxy, aryl, $C(O)R^3$, a 5- or 6-membered saturated containing one or more atoms selected from C, N, O or S, and a 5- or 6-membered heteroaromatic ring containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to yet another embodiment of the present invention, said bicyclic heteroaromatic ring system is substituted with one or more substituents independently selected from C1 to 7 alkyl or halogen. According to a further embodiment of the present invention, said alkyl is C1 to 4 alkyl. According to a further embodiment of the present invention, said halogen is bromo, fluoro or chloro.

According to another embodiment of the present invention, said bicyclic heteroaromatic ring system is selected from indole, isoindole, benzimidazole, quinoline, naphthyridine and imidazo[1,2-a]pyridine.

According to one embodiment of the present invention, $R^1$ represents a mono heteroaromatic ring system containing one or more heteroatoms selected from N, O and S; wherein said mono heteroaromatic ring system is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring is containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to another embodiment of the present invention, said ring system is unsubstituted.

According to another embodiment of the present invention, said ring system is substituted with one or more substituents independently selected from halogen, $CF_3$, $SO_{(n)}R^9$, $(CH_2)_nR^3$, $NR^4R^5$, OH, C1 to 7 alkyl, C1 to 7 alkoxy, phenoxy, aryl, $C(O)R^3$, a 5- or 6-membered saturated or partially saturated ring containing one or more atoms selected from C, N, O or S, and a mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to a further embodiment of the present invention, said ring system is substituted with one or more substituents independently selected from halogen, $CF_3$, $SO_{(n)}R^9$, $(CH_2)_nR^3$, $NR^4R^5$, C1 to 7 alkyl, C1 to 7 alkoxy, phenoxy, $C(O)R^3$, a 5- or 6-membered saturated containing one or more atoms selected from C or S, and a mono- or bicyclic heteroaromatic ring system containing one or more heteroatoms selected from N; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to another embodiment of the present invention, said ring system is substituted with one or more substituents independently selected from halogen, $CF_3$, $SO_{(n)}R^9$, $(CH_2)_nR^3$, $NR^4R^5$, OH, C1 to 7 alkyl, C1 to 7 alkoxy, phenoxy, $C(O)R^3$, a 5- or 6-membered saturated or partially saturated ring containing one or more atoms selected from C, N, O or S, and a 5- or 6-membered heteroaromatic ring containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to yet another embodiment of the present invention, said ring system is substituted with one or more substituents independently selected from halogen, $CF_3$, $SO_{(n)}R^9$, $(CH_2)_nR^3$, $NR^4R^5$, C1 to 7 alkyl, C1 to 7 alkoxy, phenoxy, $C(O)R^3$, a 5- or 6-membered saturated containing one or more atoms selected from C or S, and a 5- or 6-membered heteroaromatic ring containing one or more heteroatoms selected from N; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to a further embodiment of the present invention, $R^4$ and $R^5$ are independently selected from hydrogen or C1 to 6 alkyl. According to yet a further embodiment of the present invention, said alkyl is C1 to 4 alkyl.

According to a further embodiment of the present invention, $R^9$ is aryl or phenoxy, said aryl or phenoxy is optionally substituted with C1 to 6 alkyl. According to yet a further embodiment of the present invention, said aryl is substituted with C1 to 4 allyl.

According to a further embodiment of the present invention, n is 2.

According to a further embodiment of the present invention, $R^3$ is aryl or phenoxy and said aryl or phenoxy is optionally substituted with C1 to 6 alkyl, halogen or C1 to 6 alkoxy.

According to a further embodiment of the present invention, said aryl is substituted with halogen, C1 to 4 alkyl or C1 to 4 alkoxy.

According to yet a further embodiment of the present invention, said aryl is phenyl.

According to a further embodiment of the present invention, said ring system is substituted with at least one C1 to 6 alkyl. According to yet a further embodiment of the present invention, said alkyl is C1 to 4 alkyl.

According to a further embodiment of the present invention, said ring system is substituted with at least one halogen. According to yet a further embodiment of the present invention, said halogen is fluoro, chloro or bromo.

According to another embodiment of the present invention, said ring system is selected from pyrazole, pyrazine, oxadiazole, pyridine, isoxazole, pyrimidine, pyrrole, imidazole, furazan and triazole.

According to another embodiment of the present invention, $R^1$ represents a monocyclic heteroaromatic ring system containing one or more heteroatoms selected from N, O and S; wherein said monocyclic heteroaromatic ring is fused with one 5- or 6-membered saturated or partially saturated ring containing one or more atoms selected from C, N, O and S, wherein said monocyclic heteroaromatic ring system when fused with said 5- or 6-membered saturated or partially saturated ring is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O or S, and mono- or bicyclic heteroaromatic ring system containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to another embodiment of the present invention, $R^1$ represents a monocyclic heteroaromatic ring system containing one or more heteroatoms selected from N, O and S; wherein said monocyclic heteroaromatic ring is fused with one 5- or 6-membered saturated or partially saturated ring containing one or more atoms selected from C, N, O and S, wherein said monocyclic heteroaromatic ring system when fused with said 5- or 6-membered saturated or partially saturated ring is optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O or S, and a 5- or 6-membered heteroaromatic ring containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy.

According to yet another embodiment of the present invention, said ring system is fused with a 5-membered partially saturated ring containing one or more atoms selected from C, N, O and S.

According to yet another embodiment of the present invention, said ring system when fused is unsubstituted.

According to yet another embodiment of the present invention, said ring system when fused is substituted with one or more substituents independently selected from halogen, $CF_3$, $SO_{(n)}R^9$, $(CH_2)_nR^3$, $NR^4R^5$, OH, C1 to 7 alkyl, C1 to 7 alkoxy, phenoxy, aryl, $C(O)R^3$, a 5- or 6-membered saturated ring containing one or more atoms selected from C, N, O or S, and a mono- or bicyclic heteroaromatic ring system containing one or more heteroatoms selected from N, S or O; and wherein said C1 to 7 alkoxy is optionally aryl; and wherein said phenoxy is optionally substituted with C1 to 6 alkyl, halogen or C1 to 6 alkoxy.

According to yet another embodiment of the present invention, said ring system when fused is substituted with one or more substituents independently selected from halogen, $CF_3$, $SO_{(n)}R^9$, $(CH_2)_nR^3$, $NR^4R^5$, OH, C1 to 7 alkyl, C1 to 7 alkoxy, phenoxy, $C(O)R^3$, a 5- or 6-membered saturated ring containing one or more atoms selected from C, N, O or S, and a 5- or 6-membered heteroaromatic ring containing one or more heteroatoms selected from N, S or O; and wherein said C1 to 7 alkoxy is optionally aryl; and wherein said phenoxy is optionally substituted with C1 to 6 alkyl, halogen or C1 to 6 alkoxy.

According to a further embodiment of the present invention, said ring system when fused is substituted with C1 to 7 alkyl. According to yet a further embodiment of the present invention, said alkyl is C1 to 4 alkyl.

According to a further embodiment of the present invention, said ring system when fused is substituted with at least one halogen. According to a further embodiment of the present invention, said halogen is fluoro or chloro.

According to one aspect of the present invention, $R^3$, $R^4$, $R^5$, $R^6$ and $R^9$ are independently selected from hydrogen, C1 to 6 alkyl, aryl and phenoxy; and said aryl or said phenoxy is optionally substituted with C1 to 6 alkyl, halogen or C1 to 6 alkoxy.

One aspect of the present invention relates to a compound according of formula (I), wherein
at least one of X and Y represents S, and the other represents O or S;
L represents $(R^{12})_p$-Q-$(CR^{13}R^{14})_r$;
wherein Q is O, $NR^6$ or $NR^6C(O)$;
wherein $R^{12}$ is C1 to 6 alkyl optionally substituted with aryl; and $R^{13}$ and $R^{14}$ are hydrogen;
wherein p is 1 and r is 0 or 1; and wherein $1 \leq p+r \leq 7$;
$R^1$ represents a mono- or bicyclic heteroaromatic ring system containing one or more heteroatoms selected from N, O and S; wherein said mono- or bicyclic heteroaromatic ring system is optionally fused with one 5- or 6-membered partially saturated ring containing one or more atoms selected from C, N, O and S, wherein said mono- or bicyclic heteroaromatic ring system alone or when fused with one 5- or 6-membered partially saturated ring is optionally substituted with one or more substituents independently selected from halogen, $CF_3$, $SO_{(n)}R^9$, $(CH_2)_nR^3$, $NR^4R^5$, C1 to 7 alkyl, C1 to 7 alkoxy, aryl, phenoxy, $C(O)R^3$, a 5- or 6-membered saturated ring containing one or more atoms selected from C, N, O or S, and a mono- or bicyclic heteroaromatic ring system containing is one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy;
at each occurrence, $R^3$, $R^4$, $R^5$, $R^6$ and $R^9$ are independently selected from hydrogen, C1 to 6 alkyl, aryl and phenoxy; and said aryl or said phenoxy is optionally substituted with C1 to 6 alkyl, halogen or C1 to 6 alkoxy;
n represents an integer 2.

One embodiment of the present invention relates to a compound according of formula (I), wherein
at least one of X and Y represents S, and the other represents O or S;
L represents $(R^{12})_p$-Q-$(CR^{13}R^{14})_r$;
wherein Q is O, $NR^6$ or $NR^6C(O)$;
wherein $R^{12}$ is C1 to 6 alkyl optionally substituted with aryl; and $R^{13}$ and $R^{14}$ are hydrogen;
wherein p is 1 and r is 0 or 1; and wherein $1 \leq p+r \leq 7$;
$R^1$ represents a mono- or bicyclic heteroaromatic ring system containing one or more heteroatoms selected from N, O and S; wherein said mono- or bicyclic heteroaromatic ring system is optionally fused with one 5- or 6-membered partially saturated ring containing one or more atoms selected from C, N, O and S, wherein said mono- or bicyclic heteroaromatic ring system alone or when fused with one 5- or 6-membered partially saturated ring is optionally substituted with one or more substituents independently selected from halogen, $CF_3$, $SO_{(n)}R^9$, $(CH_2)_nR^3$, $NR^4R^5$, C1 to 7 alkyl, C1 to 7 alkoxy, aryl, phenoxy, $C(O)R^3$, a 5- or 6-membered saturated ring containing one or more atoms selected from C, N, O or S, and a 5- or 6-membered heteroaromatic ring containing one or more heteroatoms selected from N, S or O; and wherein said C1 to 7 alkoxy is optionally substituted with C1 to 6 alkoxy or aryl; and wherein said phenoxy is optionally substituted with C1 to 6 alkyl, halogen or C1 to 6 alkoxy;

at each occurrence, $R^3$, $R^4$, $R^5$, $R^6$ and $R^9$ are independently selected from hydrogen, C1 to 6 alkyl, aryl and phenoxy; and said aryl or said phenoxy is optionally substituted with C1 to 6 alkyl, halogen or C1 to 6 alkoxy;

n represents an integer 2.

According to one embodiment of the present invention, X represents S and Y represents O.

According to one embodiment of the present invention, L represents ethyl, methyl, —CH$_2$CH(CH$_3$)OCH$_2$—, —CH$_2$CH(6H$_5$)—, —CH$_2$CH$_2$NHCH$_2$—, —CH$_2$CH$_2$N(CH$_3$)CH$_2$—, —CH$_2$CH(CH$_3$)NHCH$_2$—, or —CH$_2$CH(CH$_3$)NHC(O)—.

According to one embodiment of the present invention, $R^3$ is aryl, optionally substituted with C1 to 6 alkyl, halogen or C1 to 6 alkoxy. According to another embodiment of the present invention, said aryl is substituted with C1 to 6 alkyl, halogen or C1 to 6 alkoxy.

According to one embodiment of the present invention, $R^3$ is phenoxy optionally substituted with C1 to 6 alkyl, halogen or C1 to 6 alkoxy. According to another embodiment of the present invention, said phenoxy is substituted with C1 to 6 alkyl, halogen or C1 to 6 alkoxy According to one embodiment of the present invention, $R^4$, $R^5$ and $R^6$ are independently selected from hydrogen or C1 to 6 alkyl.

According to one embodiment of the present invention, $R^9$ is aryl or phenoxy and said phenoxy or aryl is optionally substituted with C1 to 6 alkyl, halogen or C1 to 6 alkoxy.

According to another embodiment of the present invention, said aryl is phenyl.

According to other embodiments of the present invention, said C1 to 7 alkyl is methyl, ethyl, C3 alkyl or C4 alkyl.

According to one embodiment of the present invention, said C1 to 7 alkoxy is C1 to 4 alkoxy.

According to one embodiment of the present invention, wherein at least one of said substituents is halogen.

According to one embodiment of the present invention, $R^1$ is unsubstituted.

According to one aspect of the present invention, $R^1$ is selected from indole, isoindole, benzimidazole, quinoline, naphthyridine, imidazo[1,2-a]pyridine, pyrazole, pyrazine, oxadiazole, pyridine, isoxazole, pyrimidine, pyrrole, imidazole, furazan and triazole.

According to the present invention, there is also provided a compound of Formula (I):

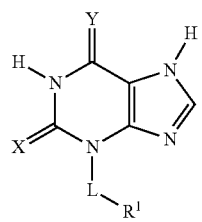

wherein at least one of X and Y represents S, and the other represents O or S;

L represents C1 to 7 alkylene, said alkylene optionally incorporating a heteroatom selected from O, S(O), and NR$^6$, said alkylene optionally incorporating one or two carbon-carbon double bonds, and said alkylene being optionally substituted by one or more substituents selected independently from OH, halogen, CN and NR$^4$R$^5$, C1 to 6 alkyl and C1 to 6 alkoxy, said alkoxy optionally incorporating a carbonyl adjacent to the oxygen;

$R^1$ represents a 5 or 6 membered heteroaromatic ring containing one or more heteroatoms selected from N, O or S and said 5 or 6 membered heteroaromatic ring may optionally be fused with a 5 or 6 membered saturated, partially saturated or unsaturated ring containing one or more atoms selected from C, N, O or S, and said ring system (said 5 or 6 membered heteroaromatic ring alone, or said 5 or 6 membered heteroaromatic ring fused with a 5 or 6 membered saturated, partially saturated or unsaturated ring) being optionally substituted by one or more substituents independently selected from halogen, CHF$_2$, CH$_2$F, CF$_3$ SO$_{(n)}$R$^9$, SO$_{(n)}$NR$^9$R$^{10}$, OH, C1 to 7 alkyl, C1 to 7 alkoxy, CN, CONR$^2$R$^3$, NR$^2$COR$^3$ and COR$^3$; said alkoxy being optionally further substituted by C1 to 6 alkoxy and said alkoxy optionally incorporating a carbonyl adjacent to the oxygen, and said alkyl being optionally further substituted by hydroxy or C1 to 6 alkoxy and said alkyl or alkoxy optionally incorporating a carbonyl adjacent to the oxygen or at any position in the alkyl;

at each occurrence, $R^2$, $R^3$, $R^4$, $R^5$, $R^6$, $R^9$ and $R^{10}$ independently represent hydrogen, C1 to 6 alkyl or C1 to 6 alkoxy said alkoxy optionally incorporating a carbonyl adjacent to the oxygen, said alkyl being optionally further substituted by halogen, C1 to 6 alkoxy, CHO, C2 to 6 alkanoyl, OH, CONR$^7$R$^8$ and NR$^7$COR$^8$;

or the groups NR$^2$R$^3$, NR$^4$R$^5$ and NR$^9$R$^{10}$ each independently represent a 5 to 7 membered saturated azacyclic ring optionally incorporating one additional heteroatom selected from O, S and NR$^{11}$, said ring being optionally further substituted by halogen, C1 to 6 alkoxy, CHO, C2 to 6 alkanoyl, OH, CONR$^7$R$^8$ and NR$^7$COR$^8$;

at each occurrence $R^7$, $R^8$ and $R^{11}$ independently represent hydrogen or C1 to 6 alkyl, or the group NR$^7$R$^8$ represents a 5 to 7 membered saturated azacyclic ring optionally incorporating one additional heteroatom selected from O, S and NR$^{11}$;

n represents an integer 0, 1 or 2;

with the proviso that $R^1$ representing thienyl or furyl is disclaimed;

as a pharmaceutically acceptable salt, solvate or solvate of a salt thereof.

In one aspect of the invention, there is provided a compound of Formula (I), wherein X represents S and Y represents O.

In another aspect of the invention, there is provided a compound of Formula (I), wherein L represents C1 to 7 alkylene.

In yet another aspect of the invention, there is provided a compound of Formula (I), wherein L represents C1 to 3 alkylene.

In yet another aspect of the invention, there is provided a compound of Formula (I), wherein L represents C1 alkylene (methylene).

In yet another aspect of the invention, there is provided a compound of Formula (I), wherein L represents C2 alkylene (ethylene).

In yet another aspect of the invention, there is provided a compound of Formula (I), wherein $R^1$ represents a 5 or 6 membered heteroaromatic ring containing one or more heteroatoms selected from N, O or S and said 5 or 6 membered heteroaromatic ring may optionally be fused with a 5 or 6 membered saturated, partially saturated or unsaturated ring containing one or more atoms selected from C, N, O or S, and said ring system (said 5 or 6 membered heteroaromatic ring alone, or said 5 or 6 membered heteroaromatic ring fused with a 5 or 6 membered saturated, partially saturated or unsaturated ring) being optionally substituted by one or more substituents independently selected from halogen, $CHF_2$, $CH_2F$, $CF_3$, $SO_{(n)}R^9$, $SO_{(n)}NR^9R^{10}$, OH, C1 to 7 alkyl, C1 to 7 alkoxy, CN, $CONR^2R^3$, $NR^2COR^3$ and $COR^3$; said alkoxy being optionally further substituted by C1 to 6 alkoxy.

In yet another aspect of the invention, there is provided a compound of Formula (I), wherein $R^1$ represents a 5 or 6 membered heteroaromatic ring containing one or more heteroatoms selected from N, O or S and said 5 or 6 membered heteroaromatic ring, fused with a 5 or 6 membered saturated, partially saturated or unsaturated ring containing one or more atoms selected from C, N, O or S, and said ring system (said 5 or 6 membered heteroaromatic ring fused with a 5 or 6 membered saturated, partially saturated or unsaturated ring) being optionally substituted by one or more substituents independently selected from halogen, $CHF_2$, $CH_2F$, $CF_3$, $SO_{(n)}R^9$, $SO_{(n)}NR^9R^{10}$, OH, C1 to 7 alkyl, C1 to 7 alkoxy, CN, $CONR^2R^3$, $NR^2COR^3$ and $COR^3$; said alkoxy being optionally further substituted by C1 to 6 alkoxy, and said alkyl being optionally further substituted by hydroxy or C1 to 6 alkoxy.

In yet another aspect of the invention, there is provided a compound of Formula (I), wherein said 5 or 6 membered heteroaromatic ring fused with a 5 or 6 membered saturated, partially saturated or unsaturated ring, is substituted with halogen.

In yet another aspect of the invention, there is provided a compound of Formula (I), wherein said halogen is selected from Cl and F.

In yet another aspect of the invention, there is provided a compound of Formula (I), wherein said 5 or 6 membered heteroaromatic ring fused with a 5 or 6 membered saturated, partially saturated or unsaturated ring, is unsubstituted.

In yet another aspect of the invention, there is provided a compound of Formula (I), wherein said 5 or 6 membered heteroaromatic ring fused with a 5 or 6 membered saturated, partially saturated or unsaturated ring, is selected from indolyl and benzimidazolyl.

In yet another aspect of the invention, there is provided a compound of Formula (I), wherein $R^1$ represents a five- or six-membered heteroaromatic ring containing 1 to 3 heteroatoms independently selected from O, N and S, said aromatic ring being optionally substituted by one or more substituents independently selected from halogen, $CHF_2$, $CH_2F$, $CF_3$, $SO_{(n)}R^9$, $SO_{(n)}NR^9R^{10}$, OH, C1 to 7 alkyl, C1 to 7 alkoxy, CN, $CONR^2R^3$, $NR^2COR^3$ and $COR^3$; said alkoxy being optionally further substituted by C1 to 6 alkoxy, and said alkyl being optionally further substituted by hydroxy or C1 to 6 alkoxy.

In yet another aspect of the invention, there is provided a compound of Formula (I), wherein $R^1$ represents a five- or six-membered heteroaromatic ring containing 1 to 3 heteroatoms independently selected from O, N and S, said aromatic ring being optionally substituted by one or more substituents independently selected from halogen, C1 to 6 alkyl and C1 to 6 alkoxy, said alkoxy being optionally further substituted by C1 to 6 alkoxy.

In yet another aspect of the invention, there is provided a compound of Formula (I), wherein $R^1$ represents a five- or six-membered heteroaromatic ring containing 1 or 2 nitrogen atoms, said aromatic ring being optionally substituted by one or more substituents independently selected from halogen, $CHF_2$, $CH_2F$, $CF_3$, $SO_{(n)}R^9$, $SO_{(n)}NR^9R^{10}$, OH, C1 to 7 alkyl, C1 to 7 alkoxy, CN, $CONR^2R^3$, $NR^2COR^3$ and $COR^3$; said alkoxy being optionally further substituted by C1 to 6 alkoxy.

In yet another aspect of the invention, there is provided a compound of Formula (I), wherein said five- or six-membered heteroaromatic ring containing 1 or 2 nitrogen atoms, is substituted by one or more substituents independently selected from halogen and C1 to 7 alkyl.

In yet another aspect of the invention, there is provided a compound of Formula (I), wherein said heteroaromatic ring is selected from pyridyl and imidazolyl.

In yet another aspect of the invention, there is provided a compound of Formula (I), wherein said heteroaromatic ring is imidazolyl, substituted with halogen and C1 to 7 alkyl.

The present invention also relates to a compound, said compound being selected from:

3-(pyridin-2-ylmethyl)-2-thioxo-1,2,3,7-tetrahydro-6H-purin-6-one;
3-(pyridin-3-ylmethyl)-2-thioxo-1,2,3,7-tetrahydro-6H-purin-6-one;
3-(pyridin-4-ylmethyl)-2-thioxo-1,2,3,7-tetrahydro-6H-purin-6-one;
3-{[3-ethoxy-4-(2-ethoxyethoxy)pyridin-2-yl]methyl}-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(2-butyl-4-chloro-1H-imidazol-5-yl)methyl]-2-thioxo-1,2,3,7-tetrahydro-6H-purin-6-one;
3-(1H-benzimidazol-2-ylmethyl)-2-thioxo-1,2,3,7-tetrahydro-6H-purin-6-one;
3-[1-(H-benzimidazol-2-yl)ethyl]-2-thioxo-1,2,3,7-tetrahydro-6H-purin-6-one;
3-[(5-chloro-1H-indol-3-yl)methyl]-2-thioxo-1,2,3,7-tetrahydro-6H-purin-6-one and 3-[(4-fluoro-1H-indol-3-yl)methyl]-2-thioxo-1,2,3,7-tetrahydro-6H-purin-6-one;

as a pharmaceutically acceptable salt, solvate or solvate of a salt thereof.

Further, the present invention also relates to a compound, said compound being selected from:

3-[2-(1H-Benzimidazol-2-yl)ethyl]-2-thioxo-1,2,3,7-tetrahydro-6H-purin-6-one;
3-(1H-Pyrazol-3-ylmethyl)-2-thioxo-1,2,3,7-tetrahydro-6H-purin-6-one;
3-[(5-Methylpyrazin-2-yl)methyl)-2-thioxo-1,2,3,7-tetrahydro-6H-purin-6-one;
3-[(3-Isopropylisoxazol-5-yl)methyl]-2-thioxo-1,2,3,7-tetrahydro-6H-purin-6-one;
3-[(4-Methyl-1,2,5-oxadiazol-3-yl)methyl]-2-thioxo-1,2,3,7-tetrahydro-6H-purin-6-one;
3-[(6-Butoxypyridin-2-yl)methyl]-2-thioxo-1,2,3,7-tetrahydro-6H-purin-6-one;
3-[(4-Butoxypyridin-2-yl)methyl]-2-thioxo-1,2,3,7-tetrahydro-6H-purin-6-one;
3-[(3-Butoxypyridin-2-yl)methyl]-2-thioxo-1,2,3,7-tetrahydro-6H-purin-6-one;
3-[2-(Pyridin-2-ylmethoxy)propyl]-2-thioxo-1,2,3,7-tetrahydro-6H-purin-6-one;
3-[(3,5-Dimethylisoxazol-4-yl)methyl]-2-thioxo-1,2,3,7-tetrahydro-6H-purin-6-one;
3-[(1-Methyl-1H-indol-2-yl)methyl]-2-thioxo-1,2,3,7-tetrahydro-6H-purin-6-one;
3-(2-Phenyl-2-pyridin-2-ylethyl)-2-thioxo-1,2,3,7-tetrahydro-6H-purin-6-one;
3-(Quinolin-4-ylmethyl)-2-thioxo-1,2,3,7-tetrahydro-6H-purin-6-one;
3-[(6-Phenoxypyridin-3-yl)methyl]-2-thioxo-1,2,3,7-tetrahydro-6H-purin-6-one;

3-{2-[(Quinolin-4-ylmethyl)amino]ethyl}-2-thioxo-1,2,3,7-tetrahydro-6H-purin-6-one;
3-(2-{[(1-Methyl-1H-indol-3-yl)methyl]amino}ethyl)-2-thioxo-1,2,3,7-tetrahydro-6H-purin-6-one;
3-{2-[Methyl(quinolin-4-ylmethyl)amino]ethyl}-2-thioxo-1,2,3,7-tetrahydro-6H-purin-6-one;
3-(2-Aminopropyl)-2-thioxo-1,2,3,7-tetrahydro-6H-purin-6-one trifluoroacetate;
3-{2-[(Pyridin-2-ylmethyl)amino]propyl}-2-thioxo-1,2,3,7-tetrahydro-6H-purin-6-one trifluoroacetate;
3-{2-[(Pyridin-3-ylmethyl)amino]propyl}-2-thioxo-1,2,3,7-tetrahydro-6H-purin-6-one;
3-{2-[(Pyridin-4-ylmethyl)amino]propyl}-2-thioxo-1,2,3,7-tetrahydro-6H-purin-6-one;
3-(2-{[(6-Chloropyridin-3-yl)methyl]amino}propyl)-2-thioxo-1,2,3,7-tetrahydro-6H-purin-6-one trifluoroacetate;
3-[2-({[6-(Trifluoromethyl)pyridin-3-yl]methyl}amino)propyl]-2-thioxo-1,2,3,7-tetrahydro-6H-purin-6-one trifluoroacetate;
3-(2-{[(4,6-Dichloropyrimidin-5-yl)methyl]amino}propyl)-2-thioxo-1,2,3,7-tetrahydro-6H-purin-6-one;
3-[2-({[2-(Dimethylamino)pyrimidin-5-yl]methyl}amino)propyl]-2-thioxo-1,2,3,7-tetrahydro-6H-purin-6-one;
3-{2-[(Quinolin-2-ylmethyl)amino]propyl}-2-thioxo-1,2,3,7-tetrahydro-6H-purin-6-one trifluoroacetate;
3-{2-[(Quinolin-3-ylmethyl)amino]propyl}-2-thioxo-1,2,3,7-tetrahydro-6H-purin-6-one;
3-(2-{[(1-tert-Butyl-3,5-dimethyl-1H-pyrazol-4-yl)methyl]amino}propyl)-2-thioxo-1,2,3,7-tetrahydro-6H-purin-6-one;
3-[2-({[1-(1,1-Dioxidotetrahydro-3-thienyl)-3,5-dimethyl-1H-pyrazol-4-yl]methyl}amino)propyl]-2-thioxo-1,2,3,7-tetrahydro-6H-purin-6-one;
3-{2-[(1H-Benzoimidazol-2-ylmethyl)amino]propyl}-2-thioxo-1,2,3,7-tetrahydro-6H-purin-6-one;
3-[2-({[1-(Phenylsulfonyl)-1H-pyrrol-2-yl]methyl}amino]propyl]-2-thioxo-1,2,3,7-tetrahydro-6H-purin-6-one trifluoroacetate;
3-{2-[({1-[(4-methylphenyl)sulfonyl]-1H-pyrrol-2-yl}methyl)amino]propyl}-2-thioxo-1,2,3,7-tetrahydro-6H-purin-6-one trifluoroacetate;
3-(2-{[(1-methyl-1H-pyrrol-2-yl)methyl]amino}propyl)-2-thioxo-1,2,3,7-tetrahydro-6H-purin-6-one;
3-[2-({[1-(4-sec-Butylphenyl)-1H-pyrrol-2-yl]methyl}amino)propyl)-2-thioxo-1,2,3,7-tetrahydro-6H-purin-6-one;
3-[2-({[1-(3-Methoxyphenyl)-1H-pyrrol-2-yl]methyl}amino)propyl]-2-thioxo-1,2,3,7-tetrahydro-6H-purin-6-one;
3-[2-({[2,5-Dimethyl-1-(1,3-thiazol-2-yl)-1H-pyrrol-3-yl]methyl}amino)propyl]-2-thioxo-1,2,3,7-tetrahydro-6H-purin-6-one;
3-[2-({[4-(3-Chlorobenzoyl)-1-methyl-1H-pyrrol-2-yl]methyl}amino)propyl]-2-thioxo-1,2,3,7-tetrahydro-6H-purin-6-one;
3-{2-[(1H-Imidazol-2-ylmethyl)amino]propyl}-2-thioxo-1,2,3,7-tetrahydro-6H-purin-6-one;
3-(2-{[(1-Methyl-1H-imidazol-2-yl)methyl]amino}propyl)-2-thioxo-1,2,3,7-tetrahydro-6H-purin-6-one;
3-(2-{[(4-Bromo-1-methyl-1H-imidazol-5-yl)methyl]amino}propyl)-2-thioxo-1,2,3,7-tetrahydro-6H-purin-6-one;
3-(2-{[(1-Methyl-1H-indol-3-yl)methyl]amino}propyl)-2-thioxo-1,2,3,7-tetrahydro-6H-purin-6-one;
2-Thioxo-3-{2-[(1H-1,2,3-triazol-5-ylmethyl)amino]propyl}-1,2,3,7-tetrahydro-6H-purin-6-one;
3-[2-({[1-(Benzyloxy)-1H-imidazol-2-yl]methyl}amino)propyl]-2-thioxo-1,2,3,7-tetrahydro-6H-purin-6-one;
3-(2-{[(6-Bromo-2-methylimidazo[1,2-a]pyridin-3-yl)methyl]amino}propyl)-2-thioxo-1,2,3,7-tetrahydro-6H-purin-6-one;
3-{2-[({1-[2-(2-Methoxyphenoxy)ethyl]-1H-pyrrol-2-yl}methyl)amino]propyl]-2-thioxo-1,2,3,7-tetrahydro-6H-purin-6-one;
N-[1-Methyl-2-(6-oxo-2-thioxo-1,2,6,7-tetrahydro-3H-purin-3-yl)ethyl]pyridine-2-carboxamide;
N-[1-Methyl-2-(6-oxo-2-thioxo-1,2,6,7-tetrahydro-3H-purin-3-yl)ethyl]nicotinamide;
N-[1-Methyl-2-(6-oxo-2-thioxo-1,2,6,7-tetrahydro-3H-purin-3-yl)-ethyl] isonicotinamide;
N-[1-methyl-2-(6-oxo-2-thioxo-1,2,6,7-tetrahydro-3H-purin-3-yl)ethyl]-1,8-naphthyridine-2-carboxamide;
N-[1-Methyl-2-(6-oxo-2-thioxo-1,2,6,7-tetrahydro-3H-purin-3-yl)ethyl]quinoline-2-carboxamide;
N-[1-Methyl-2-(6-oxo-2-thioxo-1,2,6,7-tetrahydro-3H-purin-3-yl)ethyl]pyrimidine-2-carboxamide; and
N-[1-Methyl-2-(6-oxo-2-thioxo-1,2,6,7-tetrahydro-3H-purin-3-yl)ethyl]-1H-imidazole-2-carboxamide trifluoroaceate;

or a pharmaceutically acceptable salt, solvate or solvate of a salt thereof.

The compounds of Formula (I) may exist in enantiomeric forms. Therefore, all enantiomers, diastereomers, racemates, tautomers and mixtures thereof are included within the scope of the invention. The various optical isomers may be isolated by separation of a racemic mixture of the compounds using conventional techniques, for example, fractional crystallisation, or HPLC. Alternatively, the various optical isomers may be prepared directly using optically active starting materials.

The present invention includes compounds of Formula (I), in the form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question. Thus, acid addition salts include inter alia those formed from hydrochloric acid or trifluoroacetic acid. Base addition salts include those in which the cation is inter alia sodium or potassium.

The resultant compound of Formula (I), or another salt thereof, can where necessary be converted into a pharmaceutically acceptable salt thereof; or converting the resultant compound of Formula (I) into a further compound of Formula (I); and where desired converting the resultant compound of Formula (I) into an optical isomer thereof.

The compounds of the invention and intermediates thereto may be isolated from their reaction mixtures and if necessary further purified by using standard techniques.

Intermediate compounds may also exist in enantiomeric forms and may be used as purified enantiomers, diastereomers, racemates or mixtures.

Intermediate compounds may also exist in tautomeric forms and may be used as purified tautomers or mixtures.

Unless otherwise indicated, the term "C1 to 6 alkylene" or "C1 to 6 alkyl" referred to herein denotes a straight or branched chain alkyl group having from 1 to 6 carbon atoms. Examples of such groups include methyl, ethyl, 1-propyl, 1-butyl, iso-butyl, tert-butyl, pentyl and hexyl. "C1 to 7 alkylene" or "C1 to 7 alkyl" are to be interpreted analogously.

Unless otherwise indicated, the term "C1 to 6 alkoxy" referred to herein denotes a straight or branched chain alkoxy group having from 1 to 6 carbon atoms. Examples of such groups include methoxy, ethoxy, 1-propoxy, 2-propoxy, tert-butoxy and pentoxy. The term "C1 to 7 alkoxy" is to be interpreted analogously.

Unless otherwise indicated, the term "C2 to 6 alkanoyl" referred to herein denotes a straight or branched chain alkyl group having from 2 to 6 carbon atoms incorporating a carbonyl group. Examples of such groups include acetyl, propionyl and pivaloyl.

Unless otherwise indicated, the term "halogen" referred to herein denotes fluoro, chloro, bromo and iodo.

As used herein, "a mono- or bicyclic heteroaromatic ring system containing one or more heteroatoms selected from N, O and S" refers to a ring system containing one or more heteroatoms, however not more than 4 heteroatoms, selected from nitrogen, oxygen or sulphur. Examples, but not limiting, of such ring systems are pyrrole, oxazole, isoxazole, thiazole, imidazole, pyrazole, triazole, oxadiazole, tetrazole, pyridine, pyrazine, pyrimidine and pyridazine, indole, isoindole, benzimidazole and quinoline, naphthyridine and imidazo[1,2-a]pyridine.

As used herein, the term "5- or 6-membered saturated or partially saturated ring(s) containing one or more atoms selected from C, N, O and S" refers to a ring containing 5 to 6 atoms of which 1 to 4 ring atoms are chosen from nitrogen, sulphur or oxygen, which may, unless otherwise specified, be carbon or nitrogen linked; and wherein, unless stated otherwise, a ring sulphur atom is optionally oxidised to form the S-oxide(s). Examples, but not limiting, of such rings are tetrahydrofuran, pyrrolidine, piperidine, tetrahydropyridine, morpholine, piperazine, thioazolidine, dihydrothiazolidine, pyrrolidinone and piperidinone and 1,1-dioxidotetrahydrothiophene.

Examples of a "5- or 6-membered heteroaromatic ring containing one or more heteroatoms selected from N, O or S" include, but is not limited to, pyrrole, oxazole, isoxazole, thiazole, imidazole, pyrazole, triazole, tetrazole, pyridine, pyrazine, pyrimidine and pyridazine.

Examples of a "5- or 6-membered saturated, partially saturated or unsaturated ring containing one or more atoms selected from C, N, O or S" include, but is not limited to, cyclopentane, cyclohexane, cyclohexene, cyclopentanone, tetrahydrofuran, pyrrolidine, piperidine, tetrahydropyridine, morpholine, piperazine, pyrrolidinone and piperidinone.

Examples of a "5- or 6-membered heteroaromatic ring containing one or more heteroatoms selected from N, O or S" when fused with a "5 or 6 membered saturated, partially saturated or unsaturated ring containing one or more atoms selected from C, N, O or S" include, but is not limited to, indole, isoindole, benzimidazole and quinoline Examples of a "a mono- or bicyclic heteroaromatic ring system containing one or more heteroatoms selected from nitrogen, oxygen and sulphur; wherein said mono- or bicyclic heteroaromatic ring system is fused with one or two 5- or 6-membered saturated or partially saturated ring(s) containing one or more atoms selected from carbon, nitrogen, oxygen and sulphur" include, but is not limited to, indole, isoindole, benzimidazole and quinoline, naphthyridine, imidazo[1,2-a]pyridine.

In the definition of L, wherein L is defined to represents $(R^{12})_p$-Q-$(CR^{13}R^{14})_r$, said $(R^{12})_p$ bonds to N as seen in formula (I) and said $(CR^{13}R^{14})_r$ bonds to $R^1$.

In the definition of L, wherein L is defined to represent "C1 to 7 alkylene; said alkylene optionally incorporating a heteroatom selected from O, $S(O)_n$ and $NR^6$; said alkylene optionally incorporating one or two carbon-carbon double bonds", is intended to embrace a saturated or unsaturated straight or branched chain arrangement of 1 to 7 carbon atoms having two free valencies and in which any two singly bonded carbon atoms are optionally separated by a saturated carbon atom bound to O, S or $NR^6$. The definition thus includes, for example, methylene, ethylene, propylene, hexylene, ethylethylene, —$CH_2$=$CH_2$—, —$CH_2CH$=$CH$—$CH_2$—, —$C(CH_3)$=$CH_2$—, —$CH_2$=$CH_2$—$CH_2O$—, —$CH_2O$—, —$CH_2CH_2O$—$CH_2$—, —$CH_2CH_2O$—$CH_2$—$CH_2$—, —$CH_2CH_2S$— and —$CH_2CH_2NR^6$.

Examples of a 5 to 7 membered saturated azacyclic ring optionally incorporating one additional heteroatom selected from O, S and $NR^{11}$ include pyrrolidine, piperidine, imindazolidine, pyrazolidine, piperazine, morpholine and thiomorpholine.

A further aspect of the present invention is the use of the novel compounds of Formula (I) as a medicament.

A further aspect of the present invention is the use of a compound of Formula (I), or a pharmaceutically acceptable salt thereof, in the manufacture of a medicament, for the treatment or prophylaxis of diseases or conditions in which inhibition of the enzyme MPO is beneficial.

A further aspect of the present invention provides the use of a compound of Formula (I), or a pharmaceutically acceptable salt thereof, in the manufacture of a medicament, for the treatment or prophylaxis of neuroinflammatory disorders, cardio- and cerebrovascular atherosclerotic disorders and peripheral artery disease, heart failure and respiratory disorders such as chronic obstructive pulmonary disease (COPD).

Another further aspect of the present invention provides the use of a compound of Formula (I), or a pharmaceutically acceptable salt thereof, in the manufacture of a medicament, for the treatment or prophylaxis of multiple sclerosis. Treatment may include slowing progression of disease.

Another further aspect of the present invention provides the use of a compound of Formula (I), or a pharmaceutically acceptable salt thereof, in the manufacture of a medicament, for the treatment or prophylaxis of Parkinson's disease. Treatment may include slowing progression of disease.

Another further aspect of the present invention provides the use of a compound of Formula (I) or a pharmaceutically acceptable salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

Another further aspect of the present invention provides the use of a compound of Formula (I) or a pharmaceutically acceptable salt thereof, in the manufacture of a medicament, for the treatment or prophylaxis of atherosclerosis by changing the composition of the plaques to reduce the risk of plaque rupture and atherothrombotic events.

Another further aspect of the present invention provides the use of a compound of Formula (I) or a pharmaceutically acceptable salt thereof, in the manufacture of a medicament, for the treatment or prophylaxis of respiratory disorders, such as chronic obstructive pulmonary disease. Treatment may include slowing progression of disease.

According to the present invention, there is also provided a method of treating, or reducing the risk of, diseases or conditions in which inhibition of the enzyme MPO is beneficial which comprises administering to a person suffering from or at risk of, said disease or condition, a therapeutically effective amount of a compound of Formula (I), or a pharmaceutically acceptable salt thereof.

Further, there is also provided a method of treating, or reducing the risk of, neuroinflammatory disorders, cardio- and cerebrovascular atherosclerotic disorders or peripheral artery disease, or heart failure or respiratory disorders, such as chronic obstructive pulmonary disease (COPD), in a person suffering from or at risk of, said disease or condition, wherein the method comprises administering to the person a therapeutically effective amount of a compound of Formula (I), or a pharmaceutically acceptable salt thereof.

Further, there is also provided a method of treating, or reducing the risk of, multiple sclerosis in a person suffering from or at risk of, said disease or condition, wherein the method comprises administering to the person a therapeutically effective amount of a compound of Formula (I), or a pharmaceutically acceptable salt thereof.

Further, there is also provided a method of treating, or reducing the risk of, Parkinson's disease in a person suffering from or at risk of, said disease or condition, wherein the method comprises administering to the person a therapeutically effective amount of a compound of Formula (I), or a pharmaceutically acceptable salt thereof.

There is also provided a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of a compound of Formula (I) or a pharmaceutically acceptable salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of Formula (I) or a pharmaceutically acceptable salt thereof.

In another aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of diseases or conditions in which inhibition of the enzyme MPO is beneficial.

In a further aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of neuroinflammatory disorders.

In a further aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of multiple sclerosis, cardio- and cerebrovascular atherosclerotic disorders and peripheral artery disease and heart failure and respiratory disorders, such as chronic obstructive pulmonary disease.

In another aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

The present invention further relates to therapies for the treatment of:

Neurodegenerative Disorder(s) including but not limited to Alzheimer's Disease (AD), Dementia, Cognitive Deficit in Schizophrenia (CDS), Mild Cognitive Impairment (MCI), Age-Associated Memory Impairment (AAMI), Age-Related Cognitive Decline (ARCD), Cognitive Impairement No Dementia (CIND), Multiple Sclerosis, Parkinson's Disease (PD), postencephalitic parkinsonism, Huntington's Disease, amyotrophic lateral sclerosis (ALS), motor neuron diseases (MND), Multiple System Atrophy (SA), Corticobasal Degeneration, Progressive Supranuclear Paresis, Guillain-Barré Syndrome (GBS), and Chronic Inflammatory Demyelinating Polyneuropathy (CIDP). Dementia includes, but is not limited to, Down syndrome, vascular dementia, dementia with Lewy bodies, HIV dementia, Frontotemporal dementia Parkinson's Type (FTDP), Pick's Disease, Niemann-Pick's Disease, traumatic brain injury (TBI), dementia pugilistica, Creutzfeld-Jacob Disease and prion diseases.

The present invention further relates to therapies for the treatment of:

Neuroinflammatory Disorder(s) including but not limited to Multiple Sclerosis (MS), Parkinson's disease, Multiple System Atrophy (MSA), Corticobasal Degeneration, Progressive Supranuclear Paresis, Guillain-Barré Syndrome (GBS), chronic inflammatory demyelinating polyneuropathy (CIDP). Multiple sclerosis (MS) includes Relapse Remitting Multiple Sclerosis (RRMS), Secondary Progressive Multiple Sclerosis (SPMS), and Primary Progressive Multiple Sclerosis (PPMS).

The present invention further relates to therapies for the treatment of:

Cognitive Disorder(s) including but not limited to
a) Dementia, including but not limited to Alzheimer's Disease (AD), Down syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND), Frontotemporal dementia Parkinson's Type (FTDP), progressive supranuclear palsy (PSP), Pick's Disease, Niemann-Pick's Disease, corticobasal degeneration, traumatic brain injury (TBI), dementia pugilistica, Creutzfeld-Jacob Disease and prion diseases;
b) Cognitive Deficit in Schizophrenia (CDS);
c) Mild Cognitive Impairment (MCI);
d) Age-Associated Memory Impairment (AAMI);
e) Age-Related Cognitive Decline (ARCD);
f) Cognitive Impairement No Dementia (CIND).

The present invention further relates to therapies for the treatment of:

Attention-Deficit and Disruptive Behavior Disorder(s) including but not limited to attention deficit disorder (ADD), attention deficit hyperactivity disorder (ADHD) and affective disorders.

The present invention also relates to the treatment of the diseases and conditions below which may be treated with the compounds of the present invention:

respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

The present invention further relates to combination therapies wherein a compound of Formula (I) or a pharmaceutically acceptable salt thereof, or a pharmaceutical composition or formulation comprising a compound of Formula (I) is administered concurrently or sequentially with therapy and/or an agent for the treatment of any one of cardio- and cerebrovascular atherosclerotic disorders and peripheral artery disease.

A compound of Formula (I) or a pharmaceutically acceptable salt thereof may be administered in association with compounds from one or more of the following groups:

1) anti-inflammatory agents, for example
   a) NSAIDs (e.g. acetylsalicylic acid, Ibuprofen, naproxen, flurbiprofen, diclofenac, indometacin);
   b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
   c) leukotriene receptor antagonists (e.g. CP195543, amelubant, LY293111, accolate, MK571);

2) anti-hypertensive agents, for example
   a) beta-blockers (e.g. metoprolol, atenolol, sotalol);
   b) angiotensin converting enzyme inhibitors (e.g. captopril, ramipril, quinapril, enalapril);
   c) calcium channel blockers (e.g. verapamil, diltiazem, felodipine, amlodipine);
   d) angiotensin II receptor antagonists (e.g. irbesartan, candesartan, telemisartan, losartan);

3) anti-coagulantia, for example
   a) thrombin inhibitors (e.g. ximelagatran), heparines, factor Xa inhibitors;
   b) platelet aggregation inhibitors (e.g. clopidrogrel, ticlopidine, prasugel, AZ4160);

4) modulators of lipid metabolism, for example
   a) insulin sensitizers such as PPAR agonists (e.g. pioglitazone, rosiglitazone, Galida, muraglitazaar, gefemrozil, fenofibrate);
   b) HMG-CoA reductase inhibitors, statins (e.g. simvastatin, pravastatin, atorvaststin, rosuvastatin, fluvastatin);
   c) cholesterol absorption inhibitors (e.g. ezetimibe);
   d) IBAT inhibitors (e.g. AZD-7806);
   e) LXR agonists (e.g. GW-683965A, T-0901317);
   f) FXR receptor modulators;
   g) phospholipase inhibitors;

5) anti-anginal agents, for example, nitrates and nitrites;
6) modulators of oxidative stress, for example, anti-oxidants (e.g. probucol, AG1067).

Methods of Preparation

According to the present invention, we further provide a process for the preparation of compounds of Formula (I), or a pharmaceutically acceptable salt, solvate, enantiomer, diastereomer or racemate thereof wherein $R^1$, L, X and Y are defined as in Formula (I), unless stated otherwise.

Throughout the following description of such processes it is to be understood that, where appropriate, suitable protecting groups will be added to, and subsequently removed from, is the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by one skilled in the art. The definitions of substituents and groups are as in Formula (I) except where defined differently. The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures. The terms "flash chromatography" or "flash column chromatography" shall mean preparative chromatography on silica using an organic solvent, or mixtures thereof, as mobile phase.

Preparation of End Products

1. A process for preparing a compound of Formula (I), wherein $R^1$ and L is defined as in Formula (I) and X is S and Y is O is shown in Scheme 1:

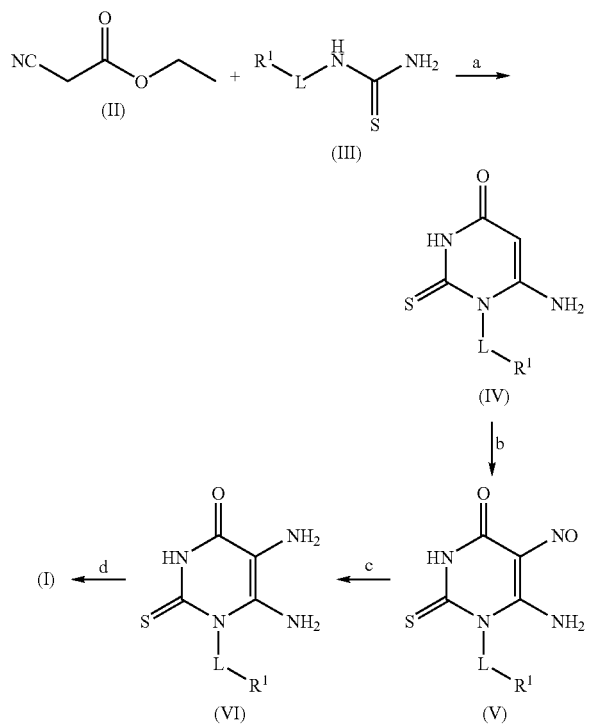

Compounds of formula (II), (III), (IV), (V) and (VI) are useful intermediates in the preparation of compound of Formula (I) (wherein $R^1$ and L are defined as in Formula (I)). Compounds of formula (II) to (VI) are either commercially available, or can be prepared from commercially available, or in the literature described compounds (Traube W., *J. Lieb. Ann.* 1904, 331, 64; Ouwerkerk et al. *Eur. J. Org. Chem.* 2002, 14, 2356).

a) Reaction of ethyl cyanoacetate (II) with a thiourea of formula (III) wherein $R^1$ and L are defined as in Formula (I). In the process, ethyl cyanoacetate (II) and an appropriate thiourea (III) are dissolved or suspended in a suitable alcohol, such as ethanol, and an alkoxide, such as sodium ethoxide, is added. The temperature is typically from 70° C. up to the reflux temperature of the reaction mixture.

b) Reaction of a thiouracil of formula (IV), wherein $R^1$ and L are defined as in Formula (I) with sodium nitrite in an acidic solution. In the process, the thiouracil of formula (IV) is suspended in a solvent, such as acetic acid, (10 to 100% in aqueous solution) or hydrochloric acid (1N aqueous solution), and stirred at a suitable temperature between 0° C. and 85° C. for 10 to 20 minutes before sodium nitrite, which is dissolved in water, is added.

c) Reduction of a nitroso compound of formula (V), wherein $R^1$ and L are defined as in Formula (I). In the process, the reduction of the nitroso compound (V) may be carried out with a suitable reducing agent, such as sodium dithionite, in a suitable solvent mixture, such as water, ammonia solution or sodium hydroxide (aq. 1N aqueous solution), at a temperature range between room temperature and 75° C. for 30 minutes up to 24 hours. Alternatively the sodium dithionite could be added directly to the conditions used in step b.

d) The reaction of a diamine of formula (VI), wherein $R^1$ and L are defined as in Formula (I) with i) formic acid, ii) formamidine acetate or with iii) trialkylorthoester is described below:

(i) the diamine of formula (VI) is treated with formic acid (98%), at a suitable temperature between ambient temperature and the reflux temperature of the reaction mixture. The process is continued for a suitable period of time, typically for between 20 to 30 minutes. After the removal of the formic acid, treatment with a suitable aqueous base, for example, with 10% aqueous sodium hydroxide solution, then yields the compound of Formula (I). The treatment with base is carried out for a suitable time at a suitable temperature, for example for about 30 to 90 minutes at a temperature between ambient temperature and the reflux temperature of the reaction mixture. Alternatively the reaction can be performed in a solvent such as water to which formic acid and sulphuric acid is added. The reaction is then heated under reflux overnight which after neutralization gives the compound of Formula (I).

(ii) the diamine of formula (VI) is treated with formamidine acetate in a solvent such as dimethyl sulfoxide at a suitable temperature, for example 70° C., until the reaction is complete, typically for 1-3 h.

(iii) the diamine of formula (VI) is treated at a suitable temperature with an excess of an appropriate ortho ester such as triethylorthoformate and tripropylorthoformate, optionally in the presence of a suitable solvent such as an alcohol, until reaction is complete. The temperature is typically up to the reflux temperature of the reaction mixture, and reaction times are generally from 30 minutes to overnight.

Other methods for the conversion of a diamine of formula (VI) into a compound of Formula (I) are described in the literature and will be readily known to the person skilled in the art.

2. A process for preparing a compound of Formula (I), wherein $R^1$ and L are defined as in Formula (I) and X is S and Y is O is shown in Scheme 2 (Suzuki et al. *Chem. Pharm. Bull.* 2002, 50, 1163):

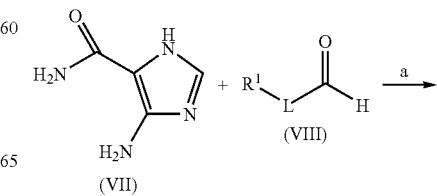

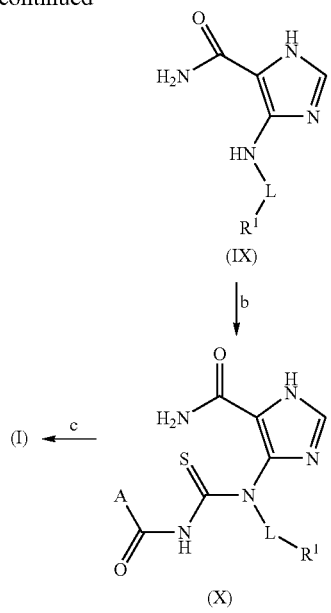

Compounds of formula (VII), (VIII), (IX) and (X) are useful intermediates in the preparation of compounds of Formula (I) wherein $R^1$ and L are defined as in Formula (I). Compounds of formula (VII) to (X) are either commercially available, or can be prepared from commercially available, or in the literature described compounds.

a) Reaction of 5-aminoimidazole-4-carboxamide (VII) with an appropriate aldehyde of formula (VIII), wherein $R^1$ and L are defined as in Formula (I), and sodium cyanoborohydride, sodium acetoxyborohydride or sodium borohydride in a suitable solvent, such as methanol, optionally with the addition of acetic acid, at room temperature or with heating up to 50° C. gave intermediate (IX). Alternatively the formed imine is isolated and reduced by catalytic hydrogenation at ambient temperature with a catalyst such as platinum oxide in a suitable solvent, such as methanol, to produce intermediate (IX).

b) Reaction of intermediate (IX), wherein $R^1$ and L are defined as in Formula (I), with an isothiocyanate such as benzoylisothiocyanate or ethoxycarbonyl isothiocyanate in a solvent such as dichloromethane at room temperature or with heating up to reflux temperature gave intermediate (X).

c) Reaction of intermediate (X), wherein $R^1$ and L are defined as in Formula (I), with a base such as sodium hydroxide or ammonia (7N in methanol) at a temperature between 80° C. and the reflux temperature of the solvent then yields the compound of Formula (I).

3. A process for preparing a compound of Formula (I), wherein $R^1$ and L are defined as below and X is S and Y is O is shown in Scheme 3:

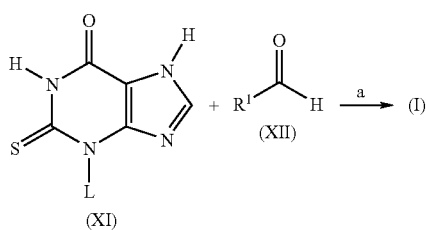

Compounds of formula (XI) and (XII) are useful intermediates in the preparation of compounds of Formula (I), wherein $R^1$ is defined as in Formula (I), and L represents $(R^{12})_p$-Q-$(CR^{13}R^{14})_r$, wherein Q is $NR^6$ and $R^6$, $R^{12}$, $R^{13}$, $R^{14}$, p and r are defined as in Formula (I). Compounds of formula (XI) to (XII) are either commercially available, or can be prepared from commercially available, or in the literature described compounds.

a) Reaction of (XI) with an appropriate aldehyde of formula (XII), wherein $R^1$ and L are defined as above, acetic acid and sodium cyanoborohydride or sodium acetoxyborohydride in a suitable solvent such as methanol, at room temperature or with heating up to 50° C. gave the compound of Formula (I).

4. A process for preparing a compound of Formula (I), wherein $R^1$ and L are defined as below and X is S and Y is O is shown in Scheme 4:

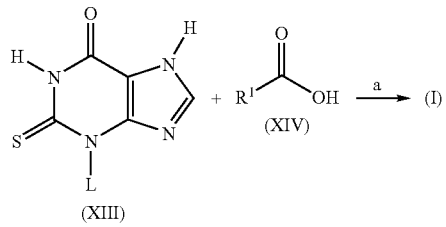

Compounds of formula (XIII) and (XIV) are useful intermediates in the preparation of compounds of Formula (I), wherein $R^1$ is defined as in Formula (I), and L represents $(R^{12})_p$-Q-$(CR^{13}R^{14})_r$, wherein Q is $NR^6$ and $R^6$, $R^{12}$, $R^{13}$, $R^{14}$, p and r are defined as in Formula (I). Compounds of formula (XIII) to (XIV) are either available, or can be prepared from commercially available, or in the literature described compounds.

a) Reaction of (XIII) with an appropriate carboxylic acid of formula (XIV), wherein $R^1$ and L are defined above, O-benzotriazol-1-yl-N,N,N,N-tetramethyluronium tetrafluoroborate and a suitable base such as diisopropylethylamine in a suitable solvent such as dimethylformamide at room temperature gave the compound of Formula (I).

The invention is illustrated, but in no way limited, by the following examples:
General Methods All solvents used were commercially available and were either anhydrous or of analytical grade. Reactions were typically run under an inert atmosphere of nitrogen or argon.

$^1$H and $^{13}$C NMR spectra were recorded at 400 MHz for proton and 100 MHz for carbon-13 either on a VARIAN® MERCURY® Plus 400 NMR Spectrometer equipped with a VARIAN® 400 ATB PFG probe, or a BRUKER® av400 NMR Spectrometer equipped with a 3 mm flow injection SEI$^1$H/D-$^{13}$C probe head with Z-gradients using a BEST 215 liquid handler for sample injection, or a BRUKER® DPX400 NMR spectrometer equipped with a 4-nucleus probe head equipped with Z-gradients. Alternatively, spectra were recorded at 600 MHz for proton (150 MHz) and carbon-13 (60 MHz) with a 5 mm TXI probehead with Z-gradients. All deuterated solvents contained typically 0.03% to 0.05% v/v tetramethylsilane, which was used as the reference signal (set at δ 0.00 for both $^1$H and $^{13}$C). When samples were run without tetramethylsilane the following reference signals were used: the middle line of DMSO-$d_6$ δ 2.50 ($^1$H), δ 39.51 ($^{13}$C); the middle line of $CD_3OD$ δ 3.31 ($^1$H) or δ 49.15 ($^{13}$C);

acetone-$d_6$ 2.04 ($^1$H), 206.5 ($^{13}$C); and CDCl$_3$ δ 7.26 ($^1$H), the middle line of CDCl$_3$ δ 77.16 ($^{13}$C) (unless otherwise indicated).

Mass spectra were recorded on a WATERS® MS consisting of an Alliance 2795 (LC) and WATERS® MICROMASS® ZQ™ detector at 120° C. The mass spectrometer was equipped with an electrospray ion source (ES) operated in a positive or negative ion mode. The mass spectrometer was scanned between m/z 100-1000 with a scan time of 0.3 s. Alternatively, mass spectra were recorded on a WATERS® LCMS consisting of an ALLIANCE® 2795 (LC), WATERS® PDA 2996, and ELS detector (SEDEX® 75) and a ZMD single quadrupole mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. The Diode Array Detector was scanned from 200-400 nm. The temperature of the ELS detector was adjusted to 40° C. and the pressure was set to 1.9 bar. For LC separation a linear gradient was applied starting at 100% A (10 mM ammonium acetate in 5% acetonitrile) and ending at 100% B (acetonitrile) after four minutes. The column used was a X-TERRA® MS C8, 3.0×50; 3.5 μm (WATERS®) run at 1.0 mL/min.

Alternatively, mass spectra were performed on a GC-MS (GC 6890, 5973N MSD) supplied by AGILENT® Technologies. The column used was a VF-5 MS, ID 0.25 mm×30 m, 0.25 μm (VARIAN® Inc.). A linear temperature gradient was applied starting at 40° C. (hold 1 min) and ending at 300° C. (hold 1 min), 25° C./min. The MS was equipped with a CI ion source and the reactant gas was methane. The MS was scanned between m/z 50-500 and the scan speed was set to 3.25 scan/s. The MS was equipped with an EI ion source. The MS was scanned between m/z 50-500 and the scan speed was set to 3.25 scan/s. The electron voltage was set to 70 eV.

Elemental Analysis for C, H and N composition was performed using a COSTECH® Instrument Elemental Combustion System ECS4010 with a helium flow of 100 mL/min (14 psi), oxygen 20 mL/min (10 psi), air 25 psi and purge of 50 mL/min. The reported analyses are an average of two runs.

HPLC analyses were performed on a WATERS® 600 Controller system with a WATERS® 717 Plus Autosampler and a WATERS® 2996 Photodiiode Array Detector. The column used was an ACE™ C$_{18}$, 5 μm, 4.60×150 mm A linear gradient was applied, starting at 95% A (0.1% H$_3$PO$_4$ in water) and ending at 55% B (MeCN) in 20 min run. The column was at ambient temperature with the flow rate of 1.0 mL/min. The Diode Array Detector was scanned from 200-400 nm. Alternatively, HPLC analyses were performed on an Agilent HP1100 system consisting of G1379A Micro Vacuum Degasser, G1312A Binary Pump, G1367A Well plate auto-sampler, G1316A Thermostated Column Compartment and G1315B Diode Array Detector. Column: X-TERRA® MS, WATERS®, 3.0×100 mm, 3.5 μm. The column temperature was set to 40° C. and the flow rate to 1.0 mL/min. The Diode Array Detector was scanned from 210-300 nm, step and peak width were set to 2 nm and 0.05 min, respectively. A linear gradient was applied, starting at 100% A (10 mM ammonium acetate in 5% acetonitrile) and ending at 100% B (MeCN), in 6 min.

Microwave heating was performed either on a CEM DISCOVER® LabMate™, or on a BIOTAGE® Initiator™ System at the indicated temperature in the recommended microwave tubes. Alternatively, microwave heating was performed on a Smith Synthesizer™ Single-mode microwave cavity producing continuous irradiation at 2450 MHz.

A typical workup procedure after a reaction consisted of extraction of the product with a solvent such as ethyl acetate, washing with water followed by drying of the organic phase over anhydrous magnesium sulfate or sodium sulfate, filtration and concentration of the solution in vacuo.

Thin layer chromatography (TLC) was performed on Alugram® (Silica gel 60 F$_{254}$) from Macherey-Nagel or on MERCK® TLC-plates (Silica gel 60 F$_{254}$) and UV was typically used to visualize the spots. Additional visualization methods were also employed in some cases. In these cases the TLC plate was developed with iodine (generated by mixing approximately 1 g of I$_2$ to 10 g silica gel), vanillin (generated by dissolving about 1 g vanillin in 100 mL 10% H$_2$SO$_4$), ninhydrin (available commercially from ALDRICH®), or Magic Stain (generated by thoroughly mixing 25 g (NH$_4$)$_6$Mo$_7$O$_{24}$.4H$_2$O, 5 g (NH$_4$)$_2$Ce(IV)(NO$_3$)$_6$, 450 mL H$_2$O and 50 mL concentrated H$_2$SO$_4$) to visualize the compound. Typical solvents used were mixtures of chloroform/methanol, dichloromethane/methanol, ethyl acetate/methanol, hexanes/ethyl acetate and heptane/ethyl acetate.

Flash chromatography was preformed using 40-63 μm (230-400 mesh) silica gel from SILICYCLE® following analogous techniques to those disclosed in Still, W. C.; Kahn, M.; and Mitra, M. *J. Org. Chem.*, 1978, 43, 2923-2925. Alternatively, flash chromatography was preformed on a Combi Flash® Companion™ using RediSep™ normal-phase flash columns. Typical solvents used were mixtures of chloroform/methanol, dichloromethane/methanol, ethyl acetate/methanol, hexanes/ethyl acetate and heptane/ethyl acetate.

Preparative chromatography was performed on either a WATERS® Prep LC 4000 System using a WATERS® 2487 Diode Array or on a WATERS® LC Module 1 plus. The column used was either a WATERS® X-TERRA® Prep C$_{18}$, 5 μm, 30×100 mm or a PHENOMENEX® LUNA® C$_{18}$, 5 μm, 21.6×250 mm Narrow gradients with acetonitrile/water, with the water containing either 0.1% trifluoroacetic acid or 10 mM ammonium acetate, were used to elute the compound at a flow rate of 20 mL/min and a total run time between 20-30 min. Alternatively, preparative chromatography was run on a WATERS® autopurification HPLC with a diode array detector. The column used was either a X-TERRA® MS C$_8$, 10 μm, 19×300 mm, or an Atlantis ATLANTIS® C$_{18}$, 5 μm, 19×100 mm Narrow gradients with acetonitrile/(95:5 0.1 M ammonium acetate:acetonitrile) were used at a flow rate of 20 mL/min. Gradient with acetonitrile/0.1 M ammonium acetate in 5% acetonitrile in MILLI-Q® Water, run from 0 to 35-50% acetonitrile, in 15 min. Flow rate: 15 ml/min. Alternatively, purification was achieved on a semi preparative SHIMADZU® LC-8A HPLC with a SHIMADZU® SPD-10A UV-VIS-detector equipped with a WATERS® Symmetry® column (C$_{18}$, 5 μm, 19 mm×100 mm). Narrow gradients with acetonitrile/0.1% trifluoroacetic acid in MILLI-Q® Water were used at a flow rate of 10 ml/min.

The following abbreviations have been used:
aq. aqueous;
Boc$_2$O di-tert-butyl dicarbonate;
m-CPBA 3-chloroperoxybenzoic acid;
DCM dichloromethane
DEAD diethyl azodicarboxylate
DIPEA N,N-diisopropylethylamine;
DMF N,N-dimethylformamide;
DMSO dimethylsulfoxide;
EtOH ethanol;
equiv. equivalent;
HOAc acetic acid;
MeOH methanol;
NaCNBH$_3$ sodium cyanoborohydride;

NaOH sodium hydroxide
o.n. over night;
r.t. room temperature;
TEMPO 2,2,6,6-tetramethyl-1-piperidinyloxy radical
THF tetrahydrofuran;
TFA trifluoroacetic acid;

Starting materials used were either available from commercial sources or prepared according to literature procedures and had experimental data in accordance with those reported. The following examples of starting material were prepared according to literature procedure:
2-(1H-Benzimidazol-2-yl)ethylamine dihydrochloride: Nicolaou, K. C.; Trujillo, J. I.; Jandeleit, B.; Chibale, K.; Rosenfeld, M.; Diefenbach, B.; Cheresh, D. A.; Goodman, S. L. *Bioorg. Med. Chem.*, 1998, 6, 1185-1208.
1,1-Dimethoxypropan-2-ol: Hunter, R.; Michael, J. P.; and Tomlinson, G. D. *Tetrahedron*, 1994, 50, 871-888.
Phenyl(pyridin-2-yl)acetaldehyde: Jpn. Kokai Tokkyo Koho (1982), 3 pp.; JP57072963

EXAMPLES

Below follows a number of non-limiting examples of compounds of the present invention.

Example 1

3-(pyridin-2-ylmethyl)-2-thioxo-1,2,3,7-tetrahydro-6H-purin-6-one (a) N-(Pyridin-2-ylmethyl)thiourea 2-(Aminomethyl)pyridine (2.0 g, 18.5 mmol) was added dropwise to a stirred solution of benzoyl isothiocyanate (3.3 g, 20.2 mmol) in $CH_2Cl_2$ (30 mL) at 0° C. The mixture was stirred at 0° C. for 4 h. The solvent was evaporated in vacuo and 1M sulfuric acid (40 mL) was added. The reaction mixture was stirred at rt for 19 h. The mixture was neutralized with saturated sodium carbonate (aq.). The oil that formed in the solution during neutralization was removed with a spatula. The solid was collected, washed and dried. The solid was then dissolved in sodium hydroxide (10% aq., 15 mL) and MeOH (5 mL) and the solution was stirred at r.t. for 20 h. The reaction mixture was neutralized with 2M sulfuric acid and the aqueous solution was extracted with ethyl acetate (2×50 mL). The organic phase was treated with activated charcoal, filtered, dried ($Na_2SO_4$) and evaporated. The residue was suspended in diethyl ether, filtered, washed with diethyl ether and dried, giving the title compound (1.35 g, 44%) as a solid. The crude product was used in the next step without further purification.
$^1$H NMR (DMSO-$d_6$) δ ppm 8.52-8.51 (1H), 8.09-8.07 (1H), 7.79-7.75 (1H), 7.43-7.22 (4H), 4.71 (2H); MS (ESI) m/z 168 (M+1).

(b) 6-Amino-1-(pyridin-2-ylmethyl)-2-thioxo-2,3-dihydro-1H-pyrimidin-4-one

N-(Pyridin-2-ylmethyl)thiourea (1.35 g, 8.09 mmol, obtained from Example 1(a)) and ethyl cyanoacetate (1.1 g, 9.71 mmol) was added to sodium ethoxide (freshly made from sodium 0.20 g, 8.9 mmol in ethanol (16 mL)). The reaction mixture was stirred under reflux at 90° C. for 16 h. The mixture was then diluted with water (20 mL) and neutralized with 2M sulfuric acid. The precipitated solid was collected by filtration, washed with water and dried, giving the title compound (1.8 g, 96%) as a solid. The crude product was used in the next step without further purification.
$^1$H NMR (DMSO-$d_6$) δ ppm 11.93 (1H), 8.51-8.50 (1H), 7.81-7.77 (1H), 7.31-7.28 (2H), 7.00 (2H), 5.72 (2H) 4.92 (1H); MS (ESI) m/z 235 (M+1).

(c) 5,6-Diamino-1-(pyridin-2-ylmethyl)-2-thioxo-2,3-dihydro-1H-pyrimidin-4-one

6-Amino-1-(pyridin-2-ylmethyl)-2-thioxo-2,3-dihydro-1H-pyrimidin-4-one (0.60 g, 2.56 mmol, obtained from Example 1(b)) was dissolved in acetic acid (90% aq., 10 mL) and was heated at 75° C. for 5 minutes. Sodium nitrite (0.20 g, 2.95 mmol) was added and heating was continued for another 30 minutes. The solvent was removed in vacuo and the residue was suspended in water (6 mL), and ammonia (32% aq., 6 mL) was added. The reaction mixture was heated at 75° C. and sodium dithionite (1.1 g, 6.4 mmol) was added and the resulting mixture was continued stirring at 75° C. for 5 minutes, and then stirred at r.t. for 30 minutes. After adjusting the solution to neutral pH with 2M sulfuric acid the precipitated solid was collected by filtration, washed with a small amount of water and dried, giving the title compound (0.331 g, 52%) as a solid. The crude product was used in the next step without further purification.
$^1$H NMR (DMSO-$d_6$) δ ppm 11.90 (1H), 8.54-8.49 (1H), 7.83-7.76 (1H), 7.38-7.28 (2H), 6.22 (2H), 5.79 (2H), 3.49 (2H); MS (ESI) m/z 250 (M+1).

(d) 3-(pyridin-2-ylmethyl)-2-thioxo-1,2,3,7-tetrahydro-6H-purin-6-one 5,6-Diamino-1-(pyridin-2-ylmethyl)-2-thioxo-2,3-dihydro-1H-pyrimidin-4-one (0.33 g, 1.3 mmol, obtained from Example 1(c)) in formic acid was heated at 70° C. for 30 minutes. The excess of formic acid was evaporated in vacuo. Sodium hydroxide (10% aq., 2 mL) was added to the residue and the reaction mixture was heated at 70° C. for 1 h. The mixture was then diluted with water (20 mL) and neutralized using 2M sulfuric acid. The precipitated solid was collected by filtration, washed with water and dried. The crude product was purified by preparative HPLC, giving the title compound (0.068 g, 20%) as a solid.
$^1$H NMR (DMSO-$d_6$) δ ppm 13.86 (1H), 12.55 (1H), 8.45-8.43 (1H), 8.09 (1H), 7.73-7.69 (1H), 7.25-7.24 (1H), 7.17 (1H), 5.79 (2H); $^{13}$C NMR (DMSO-$d_6$) δ ppm 174.3, 155.0, 152.7, 149.7, 148.9, 141.4, 136.6, 122.1, 120.8, 110.6, 51.6; MS (ESI) m/z 260 (M+1).

Example 2

3-(pyridin-3-ylmethyl)-2-thioxo-1,2,3,7-tetrahydro-6H-purin-6-one (a) 6-Amino-1-(pyridin-3-ylmethyl)-2-thioxo-2,3-dihydro-1H-pyrimidin-4-one The title compound was prepared in accordance with the general method described in Example 1(b) using N-(pyridin-3-ylmethyl)thiourea (Beaudegnies, R., Wendeborn, S., *Heterocycles*, 2003, 11, 2417-2424) (1.19 g, 7.12 mmol) and ethyl cyanoacetate (0.97 g, 8.54 mmol), giving the title compound (1.38 g, 83%) as a solid.
$^1$H NMR (DMSO-$d_6$) δ ppm 12.02 (1H), 8.48-8.46 (2H), 7.56-7.54 (1H), 7.38-7.35 (1H), 6.99 (2H), 5.72 (2H), 4.91 (1H); MS (ESI) m/z 235 (M+1).

(b) 5,6-Diamino-1-(pyridin-3-ylmethyl)-2-thioxo-2,3-dihydro-1H-pyrimidin-4-one The title compound was prepared in accordance with the general method described in Example 1(c) using 6-amino-1-(pyridin-3-ylmethyl)-2-thioxo-2,3-dihydro-1H-pyrimidin-4-one (0.50 g, 2.27 mmol, obtained from Example 2(a)), sodium nitrite (0.17 g, 2.50 mmol) and sodium dithionite (0.99 g, 5.68 mmol), with the exception that the reaction time was 1 h at r.t. after the addition of sodium dithionite. The crude title compound was obtained as a solid (0.376 g, 66%).

$^1$H NMR (DMSO-$d_6$) δ ppm: 10.31 1H), 8.47 (1H), 8.46 (1H), 7.57-7.54 (1H), 7.37-7.34 (1H), 6.18 (2H), 5.80 (2H), 3.50 (2H); MS (ESI) m/z 250 (M+1).

(c) 3-(pyridin-3-ylmethyl)-2-thioxo-1,2,3,7-tetrahydro-6H-purin-6-one

The title compound was prepared in accordance with the general method described in Example 1(d) using 5,6-diamino-1-(pyridin-3-ylmethyl)-2-thioxo-2,3-dihydro-1H-pyrimidin-4-one (0.38 g, 1.5 mmol, obtained from Example 2(b)), giving the title compound (0.072 g, 19%) as a solid.

$^1$H NMR (DMSO-$d_6$) δ ppm 13.90 (1H), 12.57 (1H), 8.64-8.63 (1H), 8.47-8.45 (1H), 8.17 (1H), 7.78-7.76 (1H), 7.34-7.31 (1H), 5.74 (2H); $^{13}$C NMR (DMSO-$d_6$) δ ppm 174.0, 152.5, 149.2, 149.1, 148.5, 141.4, 135.4, 131.7, 123.4, 110.9, 48.0; MS (ESI) m/z 260 (M+1).

Example 3

3-(pyridin-4-ylmethyl)-2-thioxo-1,2,3,7-tetrahydro-6H-purin-6-one

(a) 6-Amino-1-(pyridin-4-ylmethyl)-2-thioxo-2,3-dihydro-1H-pyrimidin-4-one

The title compound was prepared in accordance with the general method described in Example 11(b), using N-(pyridin-4-ylmethyl)thiourea (1.0 g, 5.98 mmol) and ethyl cyanoacetate (0.64 mL, 5.98), with the exception that a 4 h reaction time was used, and the solution was neutralized with acetic acid. The crude title compound was obtained (1.07 g, 76%) as a solid.

$^1$H NMR (DMSO-$d_6$) δ ppm 12.05 (1H), 8.51 (2H), 7.13 (2H), 6.96 (2H), 5.78 (2H), 4.92 (1H); MS (ESI) m/z 235 (M+1).

(b) 5,6-Diamino-1-(pyridin-3-ylmethyl)-2-thioxo-2,3-dihydro-1H-pyrimidin-4-one The title compound was prepared in accordance with the general method described in Example 1(c), using 6-amino-1-(pyridin-4-ylmethyl)-2-thioxo-2,3-dihydro-1H-pyrimidin-4-one (0.10 g, 0.43 mmol, obtained from Example 3(a)), sodium nitrite (0.034 g, 0.50 mmol) and sodium dithionite (0.20 g, 1.14 mmol), with the exception that 1.5 h of reaction time at r.t. was used after addition of sodium dithionite. The crude title compound was obtained (0.074 g, 70%) as a solid.

$^1$H NMR (DMSO-$d_6$) δ ppm 10.49 (1H), 8.51-8.50 (2H), 7.13 (2H), 6.13 (2H), 5.58 (2H), 3.49 (2H); MS (ESI) m/z 250 (M+1).

(c) 3-(pyridin-4-ylmethyl)-2-thioxo-1,2,3,7-tetrahydro-6H-purin-6-one

The title compound was prepared in accordance with the general method described in Example 1(d), using 5,6-diamino-1-(pyridin-4-ylmethyl)-2-thioxo-2,3-dihydro-1H-pyrimidin-4-one (0.25 g, 1.0 mmol, obtained from Example 3(b)), with the exception that 20 minutes of reaction time in formic acid was used, followed by a reaction time of 45 minutes in sodium hydroxide (10% aq.). The title compound was obtained (0.033, 13%) as a solid.

$^1$H NMR (DMSO-$d_6$) δ ppm 13.92 (1H), 12.62 (1H), 8.48-8.47 (2H), 8.13 (1H), 7.24 (2H), 5.72 (2H); $^{13}$C NMR (DMSO-$d_6$) δ ppm 174.2, 152.6, 159.5, 149.0, 145.0, 141.5, 122.0, 110.1, 49.4; MS (ESI) m/z 260 (M+1).

Example 4

3-{[3-ethoxy-4-(2-ethoxyethoxy)pyridin-2-yl]methyl}-2-thioxo-1,2,3,7-tetrahydro-6H-purin-6-one

(a) 3-Ethoxy-2-methyl-4H-pyran-4-one

3-Hydroxy-2-methyl-4-pyrone (10 g, 79.4 mmol) was dissolved in methanol (10 mL) and sodium hydroxide (3.49 g, 87.3 mmol) in water (8 mL) was added, followed by ethyl iodide (6.97 mL, 87.3 mmol). The reaction mixture was stirred under reflux overnight. The reaction mixture was then partitioned between water (50 mL) and $CH_2Cl_2$ (100 mL). The organic phase was washed with sodium hydroxide (5%, aq.), water, dried ($MgSO_4$) and evaporated to give the title product (8.7 g, 71%) as a solid. The crude product was used in the next step without further purification.

$^1$H NMR ($CDCl_3$) δ ppm 7.60 (1H), 6.33 (1H), 4.12 (2H), 2.31 (3H), 1.31 (3H); MS (ESI) m/z 155 (M+1).

(b) 3-Ethoxy-2-methylpyridin-4(1H)-one

Ammonia (28% aq. 20 mL) was added to a solution of 3-ethoxy-2-methyl-4H-pyran-4-one (8.5 g, 55 mmol, obtained from Example 4(a)) in ethanol (20 mL) and the mixture was stirred under reflux for 24 h. The reaction mixture was cooled to r.t. and the solution was evaporated in vacuo. The pH was adjusted to pH 1 with 2M HCl, and the aqueous phase was extracted with ethyl acetate. The pH of the water phase was then adjusted to pH 10 with 2M sodium hydroxide. The aqueous phase was extracted with ethyl acetate (3×100 mL) and then saturated with NaCl (s) and extracted with $CHCl_3$. The organic phase was dried ($Na_2SO_4$) and evaporated to give the title product (8.0 g, 95%). The crude product was used in the next step without further purification.

$^1$H NMR ($CDCl_3$) δ ppm 7.88 (1M), 6.47 (1H), 3.89 (2H), 2.42 (3H), 1.40 (3H); MS (ESI) m/z 153 (M+).

(c) 3-Ethoxy-4-(2-ethoxyethoxy)-2-methylpyridine

Triphenylphosphine (2.93 g, 11.2 mmol) was added to a stirred solution of 3-ethoxy-2-methylpyridin-4(1H)-one (1.42 g, 9.3 mmol, obtained from Example 4(b)) in THF (15 mL). 2-Ethoxy ethanol (2.93 g, 11.2 mmol) was added dropwise, followed by dropwise addition of DEAD (1.76 mL, 11.2 mmol). The reaction mixture was then stirred under reflux overnight. The solvent was evaporated in vacuo and the residue was dissolved in water (15 mL). The aqueous solution was adjusted to pH 1 with 2M hydrochloric acid, then extracted with ethyl acetate (3×20 mL). The combined organic phases were dried ($MgSO_4$) and concentrated, and the crude product was purified by flash chromatography ($CHCl_3$/MeOH; 9:1), giving the title compound (0.92 g, 44%).

¹H NMR (CDCl₃) δ ppm 8.09 (1H), 6.69 (1H), 4.23-4.15 (4H), 3.83-3.81 (2H), 3.59 (2H), 2.47 (3H), 1.37 (3H), 1.22 (3H); MS (ESI) m/z 226 (M+1).

(d) 3-Ethoxy-4-(2-ethoxyethoxy)pyridine-2-carbaldehyde

3-Ethoxy-4-(2-ethoxyethoxy)-2-methylpyridine (0.92 g, 4.09 mmol, obtained from Example 4(c)) dissolved in CH₂Cl₂ (5 mL) was added dropwise to m-CPBA (1.33 g, 4.50 mmol) in CH₂Cl₂ (5 mL) at 0° C. The reaction mixture was stirred at r.t. for 16 h. CH₂Cl₂ (10 mL) was then added and the organic phase was washed with sodium carbonate (5% aq., 2×20 mL), dried (MgSO₄) and evaporated in vacuo. The residue was dissolved in acetic anhydride (20 mL) and stirred at 130° C. for 1 h. The solvent was evaporated in vacuo and water (40 mL) was added to the residue. The pH was adjusted to pH 8 with 2M sodium hydroxide. The aqueous phase was extracted with CH₂Cl₂, dried (MgSO₄) and evaporated. The residue was dissolved in ethanol (5 mL) and 2M sodium hydroxide (8 mL) was added. The mixture was stirred under reflux for 2 h. The solvent was evaporated and the residue partitioned between water and CH₂Cl₂. The organic phase was dried (MgSO₄) and concentrated and the residue was dissolved in CH₂Cl₂ (10 mL) and manganese oxide (1.57 g, 18.06 mmol) was added. The mixture was then stirred under reflux under a nitrogen atmosphere overnight. The reaction mixture was filtrated through celite and concentrated, and the crude product was purified by flash chromatography (heptane/ethyl acetate; 1:1), giving the title compound (0.22 g, 22%).

¹H NMR (CDCl₃) δ ppm 10.37 (1H), 8.36 (1H), 6.99 (1H), 4.26-4.21 (4H), 3.84-3.82 (2H), 3.58 (2H), 1.40 (3H), 1.20 (3H); MS (ESI) m/z 240 (M+1).

(e) 4-({[3-Ethoxy-4-(2-ethoxyethoxy)pyridin-2-yl]methyl}amino)-1H-imidazole-5-carboxamide NaCNBH₃ (0.046 g, 0.73 mmol) was added in portions to a stirred solution of 5-amino-4-imidazolecarboxamide hydrochloride (0.150 g, 0.92 mmol) and 3-ethoxy-4-(2-ethoxyethoxy)pyridine-2-carbaldehyde (0.220 g, 0.92 mmol, obtained from Example 4(d)) in MeOH (1.5 mL) at r.t. over 10 minutes. The reaction mixture was stirred at r.t. for 2 days. The mixture was filtrated and the filtrate was evaporated in vacuo to give a crude of the title compound in quantitative yield. MS (ESI) m/z 364 (M+1).

(f) 3-{[3-ethoxy-4-(2-ethoxyethoxy)pyridin-2-yl]methyl}-2-thioxo-1,2,3,7-tetrahydro-6H-purin-16-one Ethoxycarbonyl isothiocyanate (0.12 mL, 1.10 mmol) was added to a stirred suspension of 4-({[3-ethoxy-4-(2-ethoxyethoxy)pyridin-2-yl]methyl}amino)-1H-imidazole-5-carboxamide (0.330 g, 0.92 mmol, obtained from Example 4(f)) in CH₂Cl₂ at r.t. The mixture was stirred at r.t. overnight, then the solvent was evaporated in vacuo. 1M sodium hydroxide (5 mL) was added to the residue and the mixture was stirred under reflux for 3 h. After neutralizing with 2M HCl, the precipitated solid was collected by filtration and purified by preparative HPLC, giving the title compound (0.040 g, 11%) as a solid.

¹H NMR (DMSO-d₆) δ ppm 13.79 (1H), 12.45 (1H), 8.07 (1H), 7.90 (1H), 6.98 (1H), 5.81 (2H), 4.22-4.16 (4H), 3.75-3.73 (2H), 3.52 (2H), 1.36 (3H), 1.13 (3H); MS (ESI) m/z 392

Example 5

3-[(5-Fluoro-1H-indol-2-yl)methyl]-2-thioxo-1,2,3,7-tetrahydro-6H-purin-6-one (a) 4-[2-(5-Fluoro-1H-indol-2-yl)hydrazino]-1H-imidazole-5-carboxamide A reaction mixture of 4-amino-5-imidazolecarboxamide hydrochloride (0.48 g, 2.94 mmol), 5-fluoro-1H-indole-2-carbaldehyde (0.40 g, 2.45 mmol), and NaCNBH₃ (0.15 g, 2.45 mmol) in methanol (3 mL) was stirred at r.t. for 1 h. Additional 5-fluoro-1H-indole-2-carbaldehyde (0.42 equiv.) was added and after stirring at r.t. for 1 h the mixture was concentrated in vacuo. The residue was dissolved in ethyl acetate and washed with water. The aqueous phase was extracted twice with ethyl acetate. The combined organic layers were dried (MgSO₄) and concentrated. The crude product was purified by flash column chromatography (CH₂Cl₂/methanol gradient; 0 to 20% methanol), obtaining 0.75 g (70%) of the title compound. MS (ESI) m/z 272 (M−1).

(b) 3-[(5-Fluoro-1H-indol-2-yl)methyl]-2-thioxo-1,2,3,7-tetrahydro-6H-purin-6-one 4-[2-(5-fluoro-1H-indol-2-yl)hydrazino]-1H-imidazole-5-carboxamide (0.46 g, 1.68 mmol, obtained from Example 5(a)) was dissolved in CH₂Cl₂ (2 mL) and methanol (2 mL). Benzoylisothiocyanate (0.30 g, 1.85 mmol) was added and the mixture was stirred at r.t. for 1 h. The mixture was then concentrated in vacuo followed by addition of ammonia (7 N in methanol, 3 mL) and heating at 80° C. for 1 h. The mixture was then concentrated and purified by preparative HPLC, obtaining the title compound (0.045 g, 8.5%) as a solid.

¹H NMR (DMSO-d₆) δ ppm 13.90 (1H), 12.59 (1H), 11.03 (1H), 8.17 (1H), 7.41-7.25 (1H), 7.16 (1H), 6.94-6.76 (1H), 6.29-6.18 (1H), 5.83 (2H); ¹³C NMR (DMSO-d₆) δ ppm 174.30, 158.43, 156.13, 153.05, 149.67, 141.96, 136.19, 132.85, 128.30, 112.66, 112.56, 111.38, 109.38, 109.12, 104.65, 104.43, 100.56, 45.12; MS (ESI) m/z 314 (M−1).

Example 6

3-[(5-Fluoro-1H-indol-3-yl)methyl]-2-thioxo-1,2,3,7-tetrahydro-6H-purin-6-one (a) tert-Butyl 5-fluoro-3-formyl-1H-indole-1-carboxylate A reaction mixture of 5-fluoro-1H-indole-3-carbaldehyde (1.00 g, 6.13 mmol), di-tert-butyl dicarbonate (3.34 g, 15.30 mmol), and Na₂CO₃ (6.50 g, 61.3 mmol) in THF (20 mL) was stirred at r.t. overnight. The mixture was concentrated in vacuo and the residue was dissolved in ethyl acetate and washed with water. The aqueous phase was extracted with ethyl acetate. The combined organic layers were dried (MgSO₄) and concentrated. The crude product was purified by flash column chromatography (heptane/ethyl acetate 1:0 to 1:1), obtaining 0.85 g (53%) of the title compound as a white solid.

¹H NMR (DMSO-d₆) δ ppm 10.07 (1H), 8.74 (1H), 8.21-8.06 (1H), 7.84 (1H), 7.41-7.22 (1H), 1.66 (9H).

(b) tert-Butyl 3-([{5-(aminocarbonyl)-1H-imidazol-4-yl]amino}methyl)-5-fluoro-1H-indole-1-carboxylate A reaction mixture of 4-amino-5-imidazolecarboxamide hydrochloride (0.20 g, 1.23 mmol), tert-butyl 5-fluoro-3- formyl-1H-indole-1-carboxylate (0.39 g, 1.48 mmol, obtained from Example 6(a)), and NaCNBH$_3$ (0.078 g, 1.23 mmol) in methanol (3 mL) was stirred at r.t. for 1 h. Additional 5-fluoro-3-formyl-indole-1-carbonylic acid tert-butyl ester (0.31 equiv.) was added and after stirring at r.t. for 1 h the mixture was concentrated in vacuo. The residue was dissolved in ethyl acetate and washed with water. The aqueous phase was extracted twice with ethyl acetate. The combined organic layers were dried (MgSO$_4$) and concentrated. The crude product was purified by flash column chromatography (heptane/ethyl acetate (1:0 to 0:1) then CH$_2$Cl$_2$), obtaining 0.32 g (70%) of the title compound. MS (ESI) m/z 374 (M+1).

(c) tert-Butyl 5-fluoro-3-[(4-oxo-2-thioxo-2,3,4,5-tetrahydro-1H-pyrrolo[3,2-d]pyrimidin-1-yl)methyl]-1H-indole-1-carboxylate tert-Butyl 3-({[5-(aminocarbonyl)-1H-imidazol-4-yl]amino}methyl)-5-fluoro-1H-indole-1-carboxylate (0.15 g, 0.32 mmol, obtained from Example 6(b)) was dissolved in CH$_2$Cl$_2$. Benzoylisothiocyanate (0.06 g, 0.35 mmol) was added and the mixture was stirred at r.t. for 7 h. The mixture was concentrated in vacuo. Ammonia (7 N in methanol, 3 mL) was added and the mixture was heated at 80° C. for 1 h. The mixture was concentrated and the residue was dissolved in ethyl acetate and washed with water. The organic layer were dried (MgSO$_4$) and concentrated in vacuo. The crude product-mixture was used in the next step without further purification. MS (ESI) m/z 414 (M−1).

(d) 3-[(5-fluoro-1H-indol-2-yl)methyl]-2-thioxo-1,2,3,7-tetrahydro-6H-purin-6-one tert-Butyl 5-fluoro-3-[(4-oxo-2-thioxo-2,3,4,5-tetrahydro-H-pyrrolo[3,2-d]pyrimidin-1-yl)methyl]-1H-indole-1-carboxylate (max 0.32 mmol, obtained from Example 6(c)) was dissolved in CH$_2$Cl$_2$ and trifluoroacetic acid (0.50 mL) was added and the mixture was stirred at r.t. for 4 h. The residue was dissolved in ethyl acetate and washed with NaHCO$_3$ (aq). The aqueous phase was purified by preparative HPLC, obtaining the title compound (0.007 g, 7.0%) as a solid.
$^1$H NMR (DMSO-d$_6$) δ ppm 13.86 (1H), 12.42 (1H), 11.16 (1H), 8.23 (1H), 7.83-7.69 (1H), 7.66-7.58 (1H), 7.40-7.26 (1H), 7.01-6.78 (1H), 5.81 (2H); $^{13}$C NMR (DMSO-d$_6$) δ ppm 174.36, 153.07, 149.82, 146.98, 141.72, 124.40, 118.56, 111.12, 42.14, 30.34, 27.80, 22.04, 14.01; MS (ESI) m/z 314 (M−1).

Example 7

3-[(2-butyl-4-chloro-1H-imidazol-5-yl)methyl]-2-thioxo-1,2,3,7-tetrahydro-6H-purin-6-one (a) 4-{[(2-Butyl-4-chloro-1H-imidazol-5-yl)methyl]amino}-1H-imidazole-5-carboxamide A reaction mixture of 4-amino-5-imidazolecarboxamide (0.50 g, 3.96 mmol), 2-butyl-5-chloro-1H-imidazole-4-carbaldehyde (0.89 g, 4.76 mmol), and NaCNBH$_3$ (0.25 g, 3.96 mmol) in methanol (5 mL) was stirred at r.t. over night. Acetic acid (0.24 g, 3.96 mmol) was added and the mixture was heated at 50° C. for 5 h. The mixture was concentrated in vacuo and dissolved in ethyl acetate and washed with water. The aqueous phase was extracted twice with ethyl acetate. The combined organic layers were dried (MgSO$_4$) and concentrated. The crude product was purified by flash column chromatography (CH$_2$Cl$_2$/methanol gradient; 0 to 20% methanol), obtaining 0.30 g (26%) of the title compound.
$^1$H NMR (400 MHz, DMSO-d$_6$) δ ppm 12.04 (2H), 7.48 (1H), 6.81 (2H), 6.10 (1H), 4.29 (2H), 2.69-2.35 (2H), 1.70-1.43 (2H), 1.43-1.12 (2H), 0.87 (3H); MS (ESI) m/z 297 (M+1).

(b) 4-{[(benzoylamino)carbonothioyl][(2-butyl-4-chloro-1H-imidazol-5-yl)methlyl]amino}-1H-imidazole-5-carboxamide 4-{[(2-Butyl-4-chloro-1H-imidazol-5-yl)methyl]amino}-1H-imidazole-5-carboxamide (0.30 g, 1.01 mmol, obtained from Example 7(a)) was dissolved in CH$_2$Cl$_2$ (5 mL) and methanol (2 mL). Benzoylisothiocyanate (0.18 g, 1.11 mmol) was added and the mixture was stirred at r.t. for 4 h. The mixture was then concentrated in vacuo and dissolved in ethyl acetate and washed with water. The aqueous phase was extracted twice with ethyl acetate and the combined organic layers were dried (MgSO$_4$) and concentrated. The crude product was purified by flash column chromatography (CH$_2$Cl$_2$/methanol gradient; 0 to 20% methanol), obtaining 0.175 g (38%) of the title compound. MS (ESI) m/z 460 (M+1).

(c) 3-[(2-butyl-4-chloro-1H-imidazol-5-yl)methyl]-2-thioxo-1,2,3,7-tetrahydro-6H-purin-6-one 4-{[(Benzoylamino)carbonothioyl][(2-butyl-4-chloro-1H-imidazol-5-yl)methyl]amino}-1H-imidazole-5-carboxamide (0.17 g, 0.37 mmol, obtained from Example 7(b)) was dissolved in ammonia (7 N in methanol, 3 mL) and the mixture was heated at 80° C. for 1 h. The mixture was concentrated and purified by preparative HPLC, obtaining the title compound (0.017 g, 14%) as a solid.
$^1$H NMR (DMSO-d$_6$) δ ppm 13.85 (1H), 12.51 (1H), 11.61 (1H), 8.14 (1H), 5.59 (2H), 2.59-2.37 (2H), 1.64-1.40 (2H), 1.36-1.16 (2H), 0.85 (3H); MS (ESI) m/z 339 (M+1).

Example 8

3-(1H-benzimidazol-2-ylmethyl)-2-thioxo-1,2,3,7-tetrahydro-6H-purin-6-one (a) N-(1H-benzimidazol-2-ylmethyl)thiourea To a suspension of 2-(Aminomethyl)benzimidazole dihydrochloride (0.66 g, 3.0 mmol) in dichloromethane (10 mL) was added DIPEA (1.05 mL, 6.0 mmol). The reaction mixture was stirred for 5 minutes and then benzoyl isothiocyante (0.44 mL, 3.3 mmol) was added dropwise. The resulting mixture was stirred for 1 h and then evaporated in vacuo. Ammonia (saturated, in MeOH, 15 mL) was added to the residue. After 4 h the reaction mixture was evaporated. Addition of CH$_2$Cl$_2$ to the residue afforded a solid, which was collected by filtration, washed with dichloromethane and dried to give the title compound (0.38 g, 62%). $^1$H NMR (DMSO-d$_6$) δ ppm 12.32 (1H), 8.17 (1H), 7.52-7.19 (4H), 4.83 (2H); MS (ESI) m/z 205 (M−1).

(b) 6-amino-1-(1H-benzimidazol-2-ylmethyl)-2-thioxo-2,3-dihydropyrimidin-4(1H)-one To a solution of N-(1H-benzimidazol-2-ylmethyl)thiourea (0.85 g, 4.1 mmol, obtained from Example 8(a)) in EtOH (10 mL) was added, dropwise, in portions during 7 h, sodium ethoxide (1M, 16.6 mL, 16.6 mmol) and a solution of ethyl cyanoacetate (1.76 mL, 16.6 mmol) in EtOH (10 mL) while the reaction was stirred at 80° C. After cooling to r.t. water (200 mL) was added followed by 2M sulphuric acid, the mixture was concentrated until precipitation occurred. The formed solid was collected by filtration, washed with water and dried to give the title compound (0.34 g, 30%) as a solid.

$^1$H NMR (DMSO-$d_6$) δ ppm 12.42 (1H), 12.00 (1H), 7.55-7.46 (2H), 7.16-7.06 (2H), 5.83 (2H), 4.97 (1H); MS (ESI) m/z 274 (M+1).

(c) 5,6-diamino-1-(1H-benzimidazol-2-ylmethyl)-2-thioxo-2,3-dihydropyrimidin-4(1H)-one To a suspension of 6-amino-1-(1H-benzimidazol-2-ylmethyl)-2-thioxo-2,3-dihydropyrimidin-4(1H)-one (0.28 g, 1.0 mmol, obtained from Example 8(b)) in acetic acid (3 mL) was added, dropwise, a solution of sodium nitrite (0.080 g, 1.1 mmol) in $H_2O$ (0.5 mL). The reaction mixture was then stirred for an additional 40 minutes before sodium dithionite (0.36 g, 2.08 g) was added. The resulting mixture was stirred 15 minutes and then evaporated in vacuo. Water (50 mL) was added and the formed solid was collected by filtration, washed with water and dried which gave the title compound (0.19 g, 63%).

$^1$H NMR (DMSO-$d_6$) δ ppm 12.42 (1H), 12.28 (1H), 7.54-7.49 (2H), 7.17 (2H), 6.27 (2H), 5.91 (2H), 3.59 (2H); MS (ESI) m/z 289 (M+1).

(d) 3-(1H-benzimidazol-2-ylmethyl)-2-thioxo-1,2,3,7-tetrahydro-6H-purin-6-one

To a solution of 5,6-diamino-1-(1H-benzimidazol-2-ylmethyl)-2-thioxo-2,3-dihydropyrimidin-4(1H)-one (0.19 g, 0.65 mmol, obtained from Example 8(c)) in DMSO (2 mL) was added formamidine acetate (0.10 g, 0.98 mmol). The reaction mixture was heated to 70° C. for 2 h. Purification of the crude product using preparative HPLC gave the title compound (0.029 g, 15%) as a solid.

$^1$H NMR (DMSO-$d_6$) δ ppm 13.91 (1H), 12.65 (1H), 12.30 (1H), 8.14 (1H), 7.52-7.39 (2H), 7.17-7.12 (2H), 5.91 (2H); $^{13}$C NMR (DMSO-$d_6$) δ ppm 175.3, 153.8, 150.4, 150.3, 144.0, 142.2, 135.0, 122.7, 122.0, 119.2, 112.0, 111.7, 46.5; MS (ESI) m/z 299 (+1).

Example 9

3-[1-(1H-benzimidazol-2-yl)ethyl]-2-thioxo-1,2,3,7-tetrahydro-6H-purin-6-one (a) N-[1-(1H-benzimidazol-2-yl)ethyl]thiourea To a suspension of 1-(1H-Benzoimidazol-2-yl)-ethylamine dihydrochloride (0.50 g, 2.1 mmol) in $CH_2Cl_2$ (10 mL) was added DIPEA (0.74 mL, 4.3 mmol). After 5 minutes benzoyl isothiocyanate (0.32 mL, 2.4 mmol) was added and the reaction mixture was stirred for 2.5 h, followed by evaporation in vacuo. Ammonia (7M in MeOH, 20 mL) was then added and the reaction was stirred another 2.5 h. The excess ammonia was removed in vacuo and $CH_2Cl_2$ (10 mL) was added, the solid was collected by filtration giving the title compound (0.33 g, 70%). MS (ESI) m/z 221 (M+1).

(b) 6-amino-1-[1-(1H-benzoimidazol-2-yl)ethyl]-2-thioxo-2,3-dihydropyrimidin-4(1H)-one To a suspension of N-[1-(1H-benzimidazol-2-yl)ethyl]thiourea (0.33 g, 1.5 mmol, obtained from Example 9(a)) in EtOH (2 mL) was added, dropwise, sodium ethoxide (21% w/w, 1.67 mL, 4.5 mmol) and a solution of ethyl cyanoacetate (0.48 mL, 4.47 mmol) in EtOH (1 mL), while heating the reaction to 80° C. during 1 h 20 minutes. The reaction was kept at 80° C. for an additional 2 h 40 minutes. After cooling to r.t., water (50 mL) and 2M sulphuric acid was added. The formed solid was collected by filtration, washed with $H_2O$ and dried to give the title compound (0.21 g, 50%).

$^1$H NMR (DMSO-$d_6$) δ ppm 11.95 (1H), 7.74 (1H), 7.45 (1H), 7.29 (1H), 7.03 (2H), 6.39 (2H), 4.70 (1H), 1.74 (3H); MS (ESI) m/z 288 (M+1).

(c) 5,6-diamino-1-[1-(1H-benzimidazol-2-yl)ethyl]-2-thioxo-2,3-dihydropyrimidin-4(1H)-one To 6-amino-1-[1-(1H-benzimidazol-2-yl)ethyl]-2-thioxo-2,3-dihydropyrimidin-4(1H)-one (0.21 g, 0.74 mmol, obtained from Example 9(d)) in acetic acid (2 mL) was added, dropwise, a solution of sodium nitrite (0.056 g, 0.81 mmol) in $H_2O$ (0.5 mL). After 50 minutes sodium dithionite (0.26 g, 1.5 mmol) was added and the reaction was stirred 20 minutes, followed by evaporation of acetic acid in vacuo and addition of water (25 mL). The precipitated solid was collected by filtration, washed with $H_2O$ and dried giving the title compound, which was used in the next step without further purification.

MS (ESI) m/z 303 (M+1).

(d) 3-[1-(1H-benzimidazol-2-yl)ethyl]-2-thioxo-1,2,3,7-tetrahydro-6H-purin-6-one To 5,6-diamino-1-[1-(1H-benzimidazol-2-yl)ethyl]-2-thioxo-2,3-dihydropyrimidin-4(1H)-one (obtained from Example 9(c)) in DMSO (2 mL) was added formamidine acetate (0.058 g, 0.56 mmol) and the reaction was heated to 80° C. for 2 h and 10 min. Purification of the crude product using preparative HPLC gave the title compound (0.025 g, 11%) as a solid.

$^1$H NMR (DMSO-$d_6$) δ ppm 13.77 (1H), 12.70 (1H), 12.17 (1H), 7.92 (1H), 7.55 (1H), 7.43-7.28 (2H), 7.12 (2H), 2.03 (3H); $^{13}$C NMR (DMSO-$d_6$) δ ppm 175.1, 153.3, 153.0, 148.6, 143.5, 141.2, 135.0, 122.1, 121.3, 118.8, 112.4, 111.4, 54.2, 15.7; MS (ESI) m/z 313 (M+1).

Example 10

3-[(5-chloro-1H-indol-3-yl)methyl]-2-thioxo-1,2,3,7-tetrahydro-6H-purin-6-one (a) tert-butyl 5-chloro-3-formyl-1H-indole-1-carboxylate A mixture of 5-chloro-1H-indole-3-carbaldehyde (WO 00/12510) (1.08 g, 6.0 mmol), potassium carbonate (4.15 g, 30.0 mmol) and $Boc_2O$ (3.27 g, 15.0 mmol) in THF (25 ml) was stirred for 19 h and then evaporated in vacuo. The residue was partitioned between water (25 ml) and chloroform (3×25 ml) and the organic phase was dried over $MgSO_4$, evaporated and purified by flash chromatography using heptane:ethyl acetate 3:1 giving the title compound (1.65 g, 98%) as a solid.

$^1$H NMR (DMSO-$d_6$) δ ppm 10.08 (1H), 8.73 (1H), 8.12 (2H), 7.50 (1H), 1.68 (9H).

(b) tert-butyl 3-({[5-(aminocarbonyl)-1H-imidazol-4-yl]amino}methyl)-5-chloro-1H-indole-1-carboxylate A mixture of tert-butyl 5-chloro-3-formyl-1H-indole-1-carboxylate (0.84 g, 3.0 mmol, obtained from Example 10(a)), 1H-imidazole-5-carboxamide dihydrochloride (0.49 g, 3.0 mmol) and sodium cyanoborohydride (0.45 g, 7.2 mmol) in MeOH (5 mL) was stirred at r.t for 19 h. The reaction mixture was partitioned between $H_2O$ (25 mL) and $CHCl_3$ (3×25 mL), the combined organic phases were dried over $MgSO_4$ and evaporated. Purification by flash chromatography on silica using a gradient of methanol (2-8%) in chloroform gave the title compound (0.30 g, 26%). MS (ESI) m/z 390 (M+1).

(c) tert-butyl 5-chloro-3-[(6-oxo-2-thioxo-1,2,6,7-tetrahydro-3H-purin-3-yl)methyl]-1H-indole-1-carboxylate A solution of tert-butyl 3-({[5-(aminocarbonyl)-1H-imidazol-4-yl]amino}methyl)-5-chloro-1H-indole-1-carboxylate (0.30 g, 0.78 mmol, obtained from Example 10(b)) and benzoyl isothiocyanate (0.13 mL, 0.94 mmol) in $CH_2Cl_2$ (5 mL) was stirred for 2 h and then evaporated. Ammonia (7 M in MeOH, 3 mL) was added to the residue and the mixture was heated to 80° C. for 2 h and then evaporated. Purification by flash chromatography using MeOH (2%) in $CHCl_3$ gave the title compound (0.15 g, 50%). $^1H_1NMR$ (DMSO-$d_6$) δ ppm 13.92 (1H), 12.57 (1H), 8.23 (1H), 8.12 (1H), 7.99 (1H), 7.81 (1H), 7.37 (1H), 5.81 (2H), 1.61 (9H); MS (ESI) m/z 430 (M−1).

(d) 3-[(5-chloro-1H-indol-3-yl)methyl]-2-thioxo-1,2,3,7-tetrahydro-6H-purin-6-one A solution of tert-butyl 5-chloro-3-[(6-oxo-2-thioxo-1,2,6,7-tetrahydro-3H-purin-3-yl)methyl]-1H-indole-1-carboxylate (0.043 g, 0.10 mmol, obtained from Example 10(c)) in $CH_2Cl_2$:TFA 4:1 (2 mL) was stirred for 3.5 h and then evaporated. Purification of the crude product by preparative HPLC gave the title compound (0.022 g, 68%) as a solid.
$^1H$ NMR (DMSO-$d_6$) δ ppm 13.87 (1H), 12.46 (1H), 11.26 (1H), 8.24 (1H), 8.06 (1H), 7.61 (1H), 7.36 (1H), 7.06 (1H), 5.83 (2H); $^{13}C$ NMR (DMSO-$d_6$) δ ppm 173.8, 152.9, 149.7, 141.8, 134.5, 128.7, 128.0, 123.8, 121.4, 119.3, 113.4, 111.2, 109.4, 43.2; MS (ESI) m/z 330 (M−1).

Example 11

3-[(4-fluoro-1H-indol-3-yl)methyl]-2-thioxo-1,2,3,7-tetrahydro-6H-purin-6-one (a) tert-butyl 4-fluoro-3-formyl-1H-indole-1-carboxylate A mixture of 4-fluoro-1H-indole-3-carbaldehyde (WO 03/088897) (0.53 g, 3.22 mmol), potassium carbonate (2.22 g, 16.1 mmol) and $Boc_2O$ (1.76 g, 8.1 mmol) in THF (15 mL) was stirred o.n. and then evaporated in vacuo. The residue was partitioned between $H_2O$ (25 ml) and $CHCl_3$ (3×25 ml) and the organic phase was dried over $MgSO_4$, evaporated and purified by flash chromatography using $CHCl_3$ giving the title compound as a solid, which was used in the next step.
$^1H$ NMR (DMSO-$d_6$) δ ppm 10.10 (1H), 8.58 (1H), 8.01 (1H), 7.48 (1H), 7.22 (1H), 1.68 (9H); MS (ESI) m/z 264 (M+1).

(b) tert-butyl 3-({[5-(aminocarbonyl)-1H-imidazol-4-yl]amino}methyl)-4-fluoro-1H-indole-1-carboxylate A mixture of tert-butyl 4-fluoro-3-formyl-1H-indole-1-carboxylate (1.10 g, 3.0 mmol, obtained from Example 11(a)), 1H-imidazole-5-carboxamide dihydrochloride (0.49 g, 3.0 mmol) and sodium cyanoborohydride (0.38 g, 6.0 mmol) in MeOH (10 mL) was stirred o.n. The reaction mixture was partitioned between $H_2O$ (25 mL) and $CHCl_3$ (3×25 mL), the combined organic phase was dried over $MgSO_4$ and evaporated. Purification by flash chromatography using a gradient of MeOH (5-10%) in $CHCl_3$ gave the title compound (0.17 g, 15%). MS (ESI) m/z 374 (M+1).

(c) tert-butyl 4-fluoro-3-[(6-oxo-2-thioxo-1,2,6,7-tetrahydro-3H-purin-3-yl)methyl]-1H-indole-1-carboxylate A solution of tert-butyl 3-({[5-(aminocarbonyl)-1H-imidazol-4-yl]amino}methyl)-4-fluoro-1H-indole-1-carboxylate (0.17 g, 0.45 mmol, obtained from Example 11(b)) and benzoyl isothiocyanate (0.073 mL, 0.54 mmol) in $CH_2Cl_2$ (5 mL) was stirred for 3 h 20 minutes and then evaporated. Ammonia (7 M in MeOH, 4 mL) was added to the residue and the mixture was heated to 80° C. for 2 h and then evaporated. Purification by flash chromatography using MeOH (2%) in $CHCl_3$ gave the title compound (0.089 g, 48%).
$^1H$ NMR (DMSO-$d_6$) δ ppm 14.06 (1H), 12.75 (1H), 8.29 (1H), 8.00 (1H), 7.71-7.26 (3H), 6.07 (2H), 1.74 (9H); MS (ESI) m/z 416 (M+1).

(d) 3-[(4-fluoro-1H-indol-3-yl)methyl]-2-thioxo-1,2,3,7-tetrahydro-6H-purin-6-one A solution of tert-butyl 4-fluoro-3-[(6-oxo-2-thioxo-1,2,6,7-tetrahydro-3H-purin-3-yl)methyl]-1H-indole-1-carboxylate (0.089 g, 0.21 mmol, obtained from Example 11(c)) in $CH_2Cl_2$:TFA 4:1 (1 mL) was stirred for 1 h 40 minutes and then evaporated. The crude product was purified by preparative HPLC, giving the title compound (0.028 g, 42%) as a solid.
$^1H$ NMR (DMSO-$d_6$) δ ppm 13.80 (1H), 12.49 (1H), 11.21 (1H), 8.10 (1H), 7.19 (1H), 7.06 (1H), 6.95 (1H), 6.78 (1H), 5.96 (2H); MS (ESI) m/z 316 (M+1).

Example 12

3-[2-(1H-Benzimidazol-2-yl)ethyl]-2-thioxo-1,2,3,7-tetrahydro-6H-purin-6-one (a) 1-[2-(1H-Benzimidazol-2-yl)ethyl]thiourea {2-(1H-Benzimidazol-2-yl)ethylamine was made as the dihydrochloride salt according to a procedure described by Nicolaou et al. *Bioorg. Med. Chem.*, 1998, 6, 1185-1208 and pretreated with DIPEA (2.07 mL, 11.86 mmol) for 5 minutes.} To a suspension of 2-(1H-benzimidazol-2-yl)ethylamine (1.39 g, 5.93 mmol) in dichloromethane (20 mL) was added benzoyl isothiocyanate (0.88 mL, 6.52 mmol). After 1 h, the reaction mixture was concentrated in vacuo. Ammonia in methanol (7N, 30 mL) was then added and the reaction stirred another 4 h. The excess ammonia and methanol were removed in vacuo and dichloromethane (15 mL) was added. The solid was removed by filtration and the filtrate concentrated in vacuo and purified by flash chromatography (methanol/dichloromethane, 5% then 10%) to give the title compound as a solid (1.12 g, 86% yield).
$^1H$ NMR (DMSO-$d_6$) δ ppm 12.28 (1H), 7.85-7.62 (2H), 7.49 (2H), 7.15-7.10 (2H), 7.05 (1H), 3.86 (2H), 3.04 (2H); MS (ESI) m/z 221 (M+1).

(b) 6-Amino-1-[2-(1H-benzimidazol-2-yl)ethyl]-2-thioxo-2,3-dihydropyrimidin-4(1H)-one To a suspension of 1-[2-(1H-benzimidazol-2-yl)ethyl]thiourea (0.44 g, 2.0 mmol, obtained from Example 12(a)) in absolute ethanol (5 mL) at 80° C. were added, over 2 h, a solution of sodium ethoxide (21% w/v, 2.2 mL, 6.0 mmol) and a solution of ethyl cyanoacetate (0.64 mL, 6.0 mmol) in absolute ethanol (1.3 mL). The reaction was kept at 80° C. for an additional 3 h. After cooling to r.t., water (75 mL) was added and the pH adjusted to ~7 using concentrated sulfuric acid. The solid that formed was collected by filtration, washed with water and dried in vacuo to give the title compound (0.55 g, 96% yield).
$^1$H NMR (DMSO-$d_6$) δ ppm 11.90 (1H), 7.65-7.59 (2H), 7.32-7.26 (2H), 7.19 (2H), 4.89 (1H), 4.97-4.62 (2H), 3.33 (2H); MS (ESI) m/z 288 (M+1).

(c) 5,6-Diamino-1-[2-(1H-benzimidazol-2-yl)ethyl]-2-thioxo-2,3-dihydropyrimidin-4(1H)-one To 6-amino-1-[2-(1H-benzimidazol-2-yl)ethyl]-2-thioxo-2,3-dihydropyrimidin-4(1H)-one (0.55 g, 1.9 mmol, obtained from Example 12(b)) in acetic acid (5 mL) was added, dropwise, a solution of sodium nitrite (0.15 g, 2.1 mmol) in water (1.3 mL). After 50 min, sodium dithionite (0.67 g, 3.8 mmol) was added and the reaction stirred for 20 min, followed by evaporation of acetic acid in vacuo and addition of water (50 mL). The precipitated solid was collected by filtration, washed with water and dried in vacuo, providing the title compound (0.29 g, 50% yield). This material was used in the next step without further purification. MS (ESI)-m/z 303 (M+1).

(d) 3-[2-(1H-Benzimidazol-2-yl)ethyl]-2-thioxo-1,2,3,7-tetrahydro-6H-purin-6-one To 5,6-diamino-1-[2-(1H-benzimidazol-2-yl)ethyl]-2-thioxo-2,3-dihydropyrimidin-4(1H)-one (0.29 g, 0.96 mmol, obtained from Example 12(c)) in DMSO (2 mL) was added formamidine acetate (0.15 g, 1.4 mmol) and the reaction was heated to 80° C. for 2 h. Purification of the crude product using preparative HPLC gave the title compound (0.035 g, 12% yield).
$^1$H NMR (DMSO-$d_6$) δ ppm 13.82 (1H), 12.55 (1H), 7.95 (1H), 7.73-7.71 (2H), 7.49-7.47 (2H), 4.96 (2H), 3.59 (2H); MS (ESI) m/z 313 (M+1).

Example 13

3-(1H-Pyrazol-3-ylmethyl)-2-thioxo-1,2,3,7-tetrahydro-6H-purin-6-one (a) 1-(1H-Pyrazol-3-ylmethyl)thiourea The title compound was prepared in accordance with the general method described in Example 12(a) by using 2H-pyrazol-3-yl-methylamine (1.20 g, 12.4 mmol), benzoyl isothiocyanate (1.8 mL, 13.6 mmol) and ammonia in methanol (7N, 60 mL) with the exception that the crude product isolated by filtration (1.39 g, 72% yield) was used in the next step without further purification. MS (ESI) m/z 157 (M+1)

(b) 6-Amino-1-(1H-pyrazol-3-ylmethyl)-2-thioxo-2,3-dihydropyrimidin-4(1H)-one

The title compound was prepared in accordance with the general method described in Example 12(b) by using 1-(1H-pyrazol-3-ylmethyl)thiourea (1.39 g, 8.87 mmol obtained from Example 13(a)), sodium ethoxide (21% w/v, 8.62 mL, 26.6 mmol) and ethyl cyanoacetate (2.84 mL, 26.6 mmol) with the exception that it was necessary to maintain the cloudy solution at 5° C. overnight to obtain precipitation (0.87 g, 44% yield).
$^1$H NMR (DMSO-$d_6$) δ ppm 12.83 (1H), 11.90 (1H), 7.71 (1H), 6.93 (2H), 6.26 (1H), 5.64 (2H), 4.89 (1H); MS (ESI) m/z 224 (M+1).

(c) 5,6-Diamino-1-(1H-pyrazol-3-ylmethyl)-2-thioxo-2,3-dihydropyrimidin-4(1H)-one The title compound was prepared in accordance with the general method described in Example 12(c) by using 6-amino-1-(1H-pyrazol-3-ylmethyl)-2-thioxo-2,3-dihydropyrimidin-4(1H)-one (0.87 g, 3.88 mmol, obtained from Example 13(b)), sodium nitrite (0.30 g, 4.27 mmol) and sodium dithionite (1.35 g, 7.77 mmol) which gave the title compound (0.63 g, 67% yield).
$^1$H NMR (DMSO-$d_6$) δ ppm 12.88 (1H), 12.17 (1H), 7.72 (1H), 6.32 (1H), 6.16 (2H), 5.70 (2H), 3.59-3.38 (2H); MS (ESI) m/z 239 (M+1).

(d) 3-(1H-Pyrazol-3-ylmethyl)-2-thioxo-1,2,3,7-tetrahydro-6H-purin-6-one

The title compound was prepared in accordance with the general method described in Example 12(d) by using 5,6-diamino-1-(1H-pyrazol-3-ylmethyl)-2-thioxo-2,3-dihydropyrimidin-4(1H)-one (0.63 g, 2.64 mmol, obtained from Example 13(c)) and formamidine acetate (0.41 g, 3.95 mmol) with the exception that after the reaction mixture had cooled to r.t., water (10 mL) was added. The cloudy solution was maintained at 0° C. for 3 h and the precipitate that formed was collected by filtration, washed with water and methanol and dried in vacuo. The material was further purified by recrystallization from DMSO/water to give the title compound (0.20 g, 31% yield).
$^1$H NMR (DMSO-$d_6$) δ ppm 13.83 (1H), 12.75-12.47 (2H), 8.12 (1H), 7.59 (0.8H, tautomer), 7.34 (0.2H, tautomer), 6.11 (1H), 5.69 (s, 2H); MS (ESI) m/z 249 (M+1).

Example 14

3-[(5-Methylpyrazin-2-yl)methyl)-2-thioxo-1,2,3,7-tetrahydro-6H-purin-6-one (a) 1-[(5-Methylpyrazin-2-yl)methyl]thiourea The title compound was prepared in accordance with the general method described in Example 12(a) by using 2-(aminomethyl)-5-methylpyrazine (1.00 g, 7.89 mmol), benzoyl isothiocyanate (1.20 mL, 8.90 mmol) and ammonia in methanol (7 N, 27 mL) with the exception that the crude product isolated by filtration (1.30 g, 91% yield) was used in the next step without further purification.
$^1$H NMR (DMSO-$d_6$) δ ppm 8.42 (1H), 8.38 (1H), 8.11-8.01 (1H), 7.20 (2H), 4.65 (2H), 2.41 (3H); MS (ESI) m/z 183 (M+1).

(b) 6-Amino-1-[(5-methylpyrazin-2-yl)methyl)-2-thioxo-2,3-dihydropyrimidin-4(1H)-one The title compound was prepared in accordance with the general method described in Example 12(b) by using 1-[(5-methylpyrazin-2-yl)methyl)thiourea (1.30 g, 7.10 mmol, obtained from Example 14(a)), sodium ethoxide (21% w/w, 28.4 ml, 28.4 mmol) and ethyl cyanoacetate (3.00 ml, 28.4 mmol) with the exception that the pH was adjusted by using 2N HCl until the mixture became cloudy. The mixture was then concentrated in vacuo until precipitation occurred. The solid was collected by filtration, washed with water and dried in vacuo to give the title compound (1.50 g, 81% yield) as a yellow solid.

$^1$H NMR (DMSO-$d_6$) δ ppm 11.93 (1H), 8.49 (1H), 8.45 (1H), 6.98 (2H), 5.76 (2H), 4.91 (1H), 2.41 (3H); MS (ESI) m/z 250 (M+1).

(c) 5,6-Diamino-1-[(5-methylpyrazin-2-yl)methyl)-2-thioxo-2,3-dihydropyrimidin-4(1H)-one To 6-amino-1-[(5-methylpyrazin-2-yl)methyl)-2-thioxo-2,3-dihydropyrimidin-4(1H)-one (0.50 g, 2.00 mmol, obtained from Example 14(b)) in 90% acetic acid (7 mL) was added, dropwise, a solution of sodium nitrite (0.14 g, 2.1 mmol) in water (1 mL). After 2 h, sodium dithionite (1.0 g, 5.0 mmol) was added and after another 2 h the mixture was concentrated in vacuo providing the title compound (0.30 g, 57% yield) as a yellow solid. This was used without further purification.

$^1$H NMR (CDCl$_3$) δ ppm 9.09 (1H), 8.36 (1H), 6.48 (2H), 5.75 (2H), 2.58 (3H); MS (ESI) m/z 265 (M+1).

(d) 3-(5-Methyl-pyrazin-2-ylmethyl)-2-thioxo-1,2,3,7-tetrahydro-purin-6-one

To 5,6-diamino-1-[(5-methylpyrazin-2-yl)methyl]-2-thioxo-2,3-dihydropyrimidin-4(1H)-one crude (0.30 g, 1.1 mmol, obtained from Example 14(c)) in DMSO (4 mL) was added formamidine acetate (0.18 g, 1.7 mmol) and the resulting solution was heated at 80° C. for 1 h. The crude mixture was diluted to 6 mL with DMSO. One sixth of that crude was purified by preparative HPLC, providing the title compound (0.014 g, 27% yield).

$^1$H NMR (DMSO-$d_6$) δ ppm 13.89 (1H), 12.59 (1H), 8.47 (1H), 8.39 (1H), 8.13 (1H), 5.80 (2H), 2.45 (3H); MS (ESI) m/z 275 (M+1).

Example 15

3-[(3-Isopropylisoxazol-5-yl)methyl]-2-thioxo-1,2,3,7-tetrahydro-6H-purin-6-one

(a) 1-[(3-Isopropylisoxazol-5-yl)methyl]thiourea

The title compound was prepared in accordance with the general method described in Example 12(a) by using 1-(3-isopropyl-isoxazol-5-yl)methylamine (0.85 g, 6.06 mmol), benzoyl isothiocyanate (0.90 mL, 6.67 mmol) and ammonia in methanol (7 N, 30 mL) with the exception that the reaction time for amine with benzoyl isothiocyanate was 12 h and the reaction mixture in ammonia was stirred o.n. Work-up was done by concentrating the reaction mixture in vacuo and adding ethyl acetate (15 mL) and water (15 mL). The is organic layer was separated, dried over sodium sulfate, filtered and concentrated. The residue was triturated with diethyl ether (10 mL) and the solid was removed by filtration. The filtrate was concentrated in vacuo to give the title compound (1.11 g, 91% yield), which was used in the next step without further purification. MS (ESI) m/z 200 (M+1).

(b) 6-Amino-1-[(3-isopropylisoxazol-5-yl)methyl]-2-thioxo-2,3-dihydropyrimidin-4(1H)-one The title compound was prepared in accordance with the general method described in Example 12(b) by using 1-[(3-isopropylisoxazol-5-yl)methyl]thiourea (1.11 g, 5.55 mmol, obtained from Example 15(a)), sodium ethoxide (21% w/v, 5.4 mL, 16.7 mmol) and ethyl cyanoacetate (1.8 mL, 16.7 mmol) with the exception that the reaction time after completed addition was 2 h. This provided 0.20 g (14% yield) of the title compound.

$^1$H NMR (DMSO-$d_6$) δ ppm 12.05 (1H), 7.11 (2H), 6.30 (1H), 4.90 (1H), 5.84-5.72 (2H), 2.96 (1H), 1.19 (6H); MS (ESI) m/z 267 (M+1).

(c) 5,6-Diamino-1-[(3-isopropylisoxazol-5-yl)methyl]-2-thioxo-2,3-dihydropyrimidin-4(1H)-one The title compound was prepared in accordance with the general method described in Example 12(c) by using 6-amino-1-[(3-isopropylisoxazol-5-yl)methyl]-2-thioxo-2,3-dihydropyrimidin-4(1H)-one (0.20 g, 0.75 mmol, obtained from Example 15(b)), sodium nitrite (0.060 g, 0.83 mmol) and sodium dithionite (0.26 g, 1.5 mmol) giving the title compound (0.070 g, 33% yield). MS (ESI) m/z 282 (M+1).

(d) 3-[(3-Isopropylisoxazol-5-yl)methyl]-2-thioxo-1,2,3,7-tetrahydro-6H-purin-6-one The title compound was prepared in accordance with the general method described in Example 12(d) by using 5,6-diamino-1-[(3-isopropylisoxazol-5-yl)methyl]-2-thioxo-2,3-dihydropyrimidin-4(1H)-one (0.070 g, 0.25 mmol, obtained from Example 15(c)) and formamidine acetate (0.040 g, 0.37 mmol) which yielded the title compound (8.0 mg, 11% yield).

$^1$H NMR (DMSO-$d_6$) δ ppm 13.95 (1H), 12.66 (1H), 8.19 (1H), 6.33 (1H), 5.77 (2H), 2.92 (1H), 1.16 (6H); MS (ESI) m/z 292 (+1).

Example 16

3-[(4-Methyl-1,2,5-oxadiazol-3-yl)methyl]-2-thioxo-1,2,3,7-tetrahydro-6H-purin-6-one

(a) 1-[(4-Methyl-1,2,5-oxadiazol-3-yl)methyl]thiourea

The title compound was prepared in accordance with the general method described in Example 12(a) by using 1-(4-methyl-1,2,5-oxadiazol-3-yl)methylamine (0.46 g, 4.1 mmol), benzoyl isothiocyanate (0.60 mL, 4.5 mmol) and ammonia in methanol (7 N, 25 mL) with the exception that the crude product isolated by filtration (0.55 g, 78% yield) was used in the next step without further purification.

$^1$H NMR (DMSO-$d_6$) δ ppm 8.12 (2H), 7.32 (1H), 4.80 (2H), 2.37 (3H); MS (ESI) m/z 173 (M+1).

(b) 6-Amino-1-[(4-methyl-1,2,5-oxadiazol-3-yl)methyl]-2-thioxo-2,3-dihydropyrimidin-4(1H)-one The title compound was prepared in accordance with the general method described in Example 12(b) by using 1-[(4-methyl-1,2,5-oxadiazol-3-yl)methyl]thiourea (0.55 g, 3.2 mmol, obtained from Example 16(a)), sodium ethoxide (21% w/v, 3.1 mL, 9.5 mmol) and ethyl cyanoacetate (1.0 mL, 9.5 mmol) which provided the title compound (0.44 g, 58% yield).

$^1$H NMR (DMSO-$d_6$) δ ppm 12.08 (1H), 7.11 (2H), 5.72 (2H), 4.92 (1H), 2.40 (3H); MS (ESI) m/z 240 (M+1).

(c) 5,6-Diamino-1-[(4-methyl-1,2,5-oxadiazol-3-yl)methyl]-2-thioxo-2,3-dihydropyrimidin-4(1H)-one The title compound was prepared in accordance with the general method described in Example 12(c) by using 6-amino-1-[(4-methyl-1,2,5-oxadiazol-3-yl)methyl]-2-thioxo-2,3-dihydropyrimidin-4(1H)-one (0.44 g, 1.8 mmol, obtained from Example 16(b)), sodium nitrite (0.14 g, 2.0 mmol) and sodium dithionite (0.64 g, 3.7 mmol) which gave the title compound (0.41 g, 88% yield).

$^1$H NMR (DMSO-$d_6$) δ ppm 12.31 (1H), 6.29 (2H), 5.81 (2H), 3.59-3.37 (2H), 2.40 (3H); MS (ESI) m/z 255 (M+1)

(d) 3-[(4-Methyl-1,2,5-oxadiazol-3-yl)methyl]-2-thioxo-1,2,3,7-tetrahydro-6H-purin-6-one The title compound was prepared in accordance with the general method described in Example 12(d) by using 5,6-diamino-1-[(4-methyl-1,2,5-oxadiazol-3-yl)methyl]-2-thioxo-2,3-dihydropyrimidin-4(1H)-one (0.41 g, 1.6 mmol, obtained from Example 16(c)) and formamidine acetate (0.25 g, 2.4 mmol) with the exception that after the reaction mixture had cooled to r.t., water (20 mL) was added. The cloudy solution was maintained at 5° C. o.n. and the precipitate that formed was collected by filtration, washed with water and methanol and dried. The material was further purified by recrystallization from DMSO/water to give the title compound (59.9 g, 14% yield).

$^1$H NMR (DMSO-$d_6$) δ ppm 13.99 (1H), 12.70 (1H), 8.20 (1H), 5.80 (2H), 2.45 (3H); MS (ESI) m/z 265 (M+1).

Example 17

3-[(6-Butoxypyridin-2-yl)methyl]-2-thioxo-1,2,3,7-tetrahydro-6H-purin-6-one

(a) Methyl 6-chloro-pyridine-2-carboxylate

To 6-hydroxy-pyridine-2-carboxylic acid methyl ester (10.0 g, 71.9 mmol) was added phosphorus oxychloride (138 mL). The mixture was heated in an oil bath at 110° C. for 14 h and the excess phosphorus oxychloride was removed in vacuo. The resulting residue was cooled in an ice bath and anhydrous methanol (146 mL) was slowly added. After 15 min, half of the methanol was removed in vacuo and water (208 mL) was added. The solution was cooled in an ice bath and the precipitate was collected. The solid was dissolved in ethyl acetate and this organic phase was washed with water and then a saturated sodium bicarbonate solution. The combined aqueous layers were extracted with ethyl acetate and diethyl ether. The organic layers were combined, dried over sodium sulfate, filtered and concentrated in vacuo generating 7.47 g (61% yield, 43.5 mmol) of the title compound.

$^1$H NMR (CDCl$_3$) δ ppm 8.07 (1H), 7.82 (1H), 7.54 (1H), 4.01 (3H); MS (ESI) m/z 172 (M+1).

(b) Methyl 6-butoxypyridine-2-carboxylate

To methyl 6-chloro-pyridine-2-carboxylate (2.58 g, 15.0 mmol, obtained from Example 17(a)) was added 1-butanol (35 mL) followed by sodium bis(trimethylsilyl)amide (5.51 g, 30.1 mmol). The suspension was warmed to 130° C. for 24 h after which more sodium bis(trimethylsilyl)amide (5.51 g, 30.1 mmol) was added. After another 24 h at reflux, the solution was cooled to r.t. and was poured into 200 mL 1N HCl in an ice bath. The aqueous solution was extracted twice with ethyl acetate. The organic layers were combined, dried over sodium sulfate, filtered and concentrated in vacuo resulting in 3.79 g of crude 6-butoxy-pyridine-2-carboxylic acid. To the crude 6-butoxy-pyridine-2-carboxylic acid was added thionyl chloride (100 mL) and after 1 h the resulting solution was concentrated in vacuo. To the residue was slowly added anhydrous methanol (100 mL) and after stirring o.n., the solvents were removed in vacuo. The resulting 3.73 g of crude material was purified by silica gel column chromatography (hexanes/ethyl acetate, 8:1) resulting in 2.46 g of the title compound as a colourless oil (78% yield, 11.7 mmol).

$^1$H NMR (CDCl$_3$) δ ppm 7.70-7.65 (2H), 6.91 (1H), 4.39 (2H), 3.95 (3H), 1.81-1.74 (2H), 1.54-1.44 (2H), 0.98 (3H).

(c) (6-Butoxypyridin-2-yl)methanol

Methyl 6-butoxypyridine-2-carboxylate (2.46 g, 11.8 mmol, obtained from Example 17(b)) was dissolved in absolute ethanol (112 mL) and sodium borohydride (1.78 g, 47.0 mmol, 4 equiv.) was added. After refluxing for 1 h, another 2 equivalents of sodium borohydride were added and then after 2 h more an additional 2 equivalents more sodium borohydride were added. After another 3 h the reaction was cooled to r.t. and concentrated in vacuo. The residue was partitioned between water and ethyl acetate. The layers were separated and the aqueous layer was extracted with ethyl acetate. The combined organic layers were dried over sodium sulfate, filtered and concentrated in vacuo producing 1.92 g (91% yield, 10.7 mmol) of the title compound as a clear liquid.

$^1$H NMR (CDCl$_3$) δ ppm 7.55 (1H), 6.77 (1H), 6.62 (1H), 4.66 (2H), 4.31 (2H), 3.51 (1H), 1.80-1.73 (2H), 1.48-1.42 (2H), 0.97 (3H); MS (ESI) m/z 182 (M+H).

(d) 6-Butoxypyridine-2-carbaldehyde

Activated manganese dioxide (2.40 g, 27.6 mmol) was added to a solution of (6-butoxy-pyridin-2-yl)methanol (0.52 g, 2.85 mmol, obtained from Example 17(c)) in anhydrous dichloromethane (5 mL). The resulting solution was heated to reflux for 2 h and then cooled to r.t. and 50 mL of dichloromethane added. The black solid was removed by filtration through silica gel and washed with dichloromethane. The combined filtrate was concentrated in vacuo providing the title compound (0.43 mg, 84%) as a light yellow oil.

$^1$H NMR (DMSO-$d_6$) δ ppm 9.84 (1H), 7.91 (1H), 7.54 (1H), 7.11 (1H), 4.33 (2H), 1.75-1.66 (2H), 1.46-1.36 (2H), 0.91 (3H); MS (ESI) m/z 180 (M+1).

(e) 4-{[(6-Butoxypyridin-2-yl)methyl]amino}-1H-imidazole-5-carboxamide

5-Aminoimidazole-4-carboxamide (0.30 g, 2.4 mmol) was added to the solution of 6-butoxypyridine-2-carbaldehyde (0.43 mg, 2.4 mmol, obtained from Example 17(d)) in anhydrous ethanol (30 mL) and the reaction mixture was refluxed. After 2 h, the reaction mixture was concentrated in vacuo. The light pink solid was suspended in anhydrous ethanol (25 mL), and acetic acid (0.27 mL, 4.8 mmol) was added. After 1.5 h, sodium cyanoborohydride (0.30 g, 4.8 mmol) was added to the mixture. After stirring o.n. at ambient temperature, the reaction mixture was concentrated in vacuo. The resulting 1.2 g of crude title compound was used in the next step without further purification. MS (ESI) m/z 290 (M+1)

(f) 3-[(6-Butoxypyridin-2-yl)methyl]-2-thioxo-1,2,3,7-tetrahydro-6H-purin-6-one Ethoxycarbonyl isothiocyanate (0.55 mL, 4.86 mmol) was added to a suspension of 4-{[(6-butoxypyridin-2-yl)methyl]

amino}-1H-imidazole-5-carboxamide (1.2 g, crude material from previous step) in anhydrous dichloromethane (20 mL). After stirring for 24 h at r.t., starting material remained, an additional amount of ethoxycarbonyl isothiocyanate (0.23 mL, 2.2 mmol) was added and the reaction was heated at reflux for 3 h, and then was left stirring at r.t. o.n. An additional amount of ethoxycarbonyl isothiocyanate (0.46 mL, 4.1 mmol) was added and the reaction was heated to reflux. After 1 h, insoluble material was filtered off and the filtrate was concentrated in vacuo providing 2.73 g of solid. 1.0 g of this solid was suspended in 1N NaOH (20 mL) and heated to reflux. After 1 h, the reaction mixture was cooled down to r.t. and adjusted with 2N HCl to pH~7. The formed precipitate was filtered and washed with methanol and dichloromethane. The solid (161 mg) was purified by preparative HPLC generating 30 mg (10% yield) of the title compound.

$^1$HNMR (DMSO-d$_6$) δ ppm 13.87 (1H), 12.57 (1H), 8.12 (1H), 7.60 (1H), 6.75 (1H), 6.61 (1H), 5.71 (2H), 4.00 (2H), 1.52-1.44 (2H), 1.95-1.30 (2H), 0.84 (3H); MS (ESI) m/z 332 (M+1).

Example 18

3-[(4-Butoxypyridin-2-yl)methyl]-2-thioxo-1,2,3,7-tetrahydro-6H-purin-6-one (a) 4-Butoxypyridine-2-carboxylic acid Sodium bis(trimethylsilyl)amide (28.8 g, 157 mmol) was added slowly to anhydrous n-butanol (52 mL). After 1 h, 4-chloro-pyridine-2-carboxylic acid (3.00 g, 19.1 mmol) was added and the reaction was heated to 150° C. for 3 h. Potassium bis(trimethylsilyl)amide (7.80 g, 39.2 mmol) in n-butanol (30 mL) was added to the reaction mixture and this was heated o.n. The mixture was cooled to r.t and pH was adjusted to 5 with 1N NaHSO$_4$ solution. The mixture was extracted with ethyl acetate. The ethyl acetate layer was dried over sodium sulfate, filtered and the solvent was removed in vacuo to give the title compound (3.40 g, 94% yield) as a solid.

$^1$H NMR (DMSO-d$_6$) δ ppm 8.56 (1H), 7.64 (1H), 7.36 (1H), 4.24 (2H), 1.78-1.71 (2H), 1.49-1.40 (2H), 0.94 (3H); MS (ESI) m/z 196 (M+1).

(b) Methyl 4-butoxypyridine-2-carboxylate

4-Butoxypyridine-2-carboxylic acid (3.40 g, 17.4 mmol, obtained from Example 18(a)) was dissolved in thionyl chloride (5 mL). After 1 h, the solvent was removed in vacuo. Methanol (10 mL) was added to the residue. After 3 h the resulting solution was concentrated in vacuo. The crude was dissolved in ethyl acetate. The organic layer was washed with saturated sodium bicarbonate, brine, dried over sodium sulfate, filtered and concentrated. The crude product was purified by silica gel column chromatography (hexanes/ethyl acetate, 4:1 then 1:1) to give the title compound (1.20 g, 33% yield) as a colorless oil.

$^1$H NMR (CDCl$_3$) δ ppm 8.53 (1H), 7.67 (1H), 6.96 (1H), 4.08 (2H), 4.01 (3H), 1.85-1.78 (2H), 1.56-1.46 (2H), 0.99 (t, 3H); MS (ESI) m/z 210 (M+1).

(c) (4-Butoxypyridin-2-yl)methanol

To a solution of methyl 4-butoxypyridine-2-carboxylate (1.20 g, 5.80 mmol, obtained from Example 18(b)) in methanol (60 mL) was added sodium borohydride (0.85 g, 23.0 mmol). The reaction was monitored by TLC (hexanes/ethyl acetate, 1:2). After the disappearance of starting material, the reaction mixture was concentrated in vacuo and the crude was dissolved in ethyl acetate/water (1:1, 60 mL). The aqueous layer was separated and extracted with ethyl acetate (2×20 mL). The combined organic layers were washed with brine, dried over sodium sulfate, filtered and solvent was removed in vacuo to give the title compound (0.87 g, 84% yield) as a colorless oil.

$^1$H NMR (CDCl$_3$) δ ppm 8.34 (1H), 6.75 (1H), 6.72 (1H), 4.70 (2H), 4.02 (2H), 1.82-1.75 (2H), 1.54-1.44 (2H), 0.98 (3H); MS (ESI) m/z 182 (M+1).

(d) 4-Butoxypyridine-2-carbaldehyde

The title compound was prepared in accordance with the general method described in Example 17(d) using (4-butoxypyridin-2-yl)methanol (0.82 g, 4.50 mmol, obtained from Example 18(c)) and activated manganese dioxide (3.50 g, 40.5 mmol). 0.67 g of title compound (82% yield) was obtained as a colorless oil.

$^1$H NMR (CDCl$_3$) δ ppm 10.04 (1H), 8.57 (1H), 7.46 (1H), 7.01 (1H), 4.09 (2H), 1.82-1.75 (2H), 1.54-1.44 (2H), 0.99 (3H).

(e) 4-{([(4-Butoxypyridin-2-yl)methyl]amino}-1H-imidazole-5-carboxamide

The title compound was prepared in accordance with the general method described in Example 17(e) using 4-butoxypyridine-2-carbaldehyde (0.67 g, 5.0 mmol, obtained from Example 18(d)), 5-aminoimidazole-4-carboxamide (0.81 g, 4.5 mmol), acetic acid (0.58 mL, 9.0 mmol) and sodium cyanoborohydride (0.57 g, 9.0 mmol) with the exception for the following change in work-up. The crude product was dissolved in ethyl acetate/water (1:1, 60 mL). The pH was adjusted to 8. The aqueous layer was separated and extracted with ethyl acetate (2×20 mL). The combined organic layers were washed with brine, dried over sodium sulfate, filtered and concentrated in vacuo to give the title compound (1.20 g, 90% yield). MS (ESI) m/z 290 (M+1).

(f) (3-[(4-Butoxypyridin-2-yl)methlyl]-2-thioxo-1,2,3,7-tetrahydro-6H-purin-6-one To a solution of 4-{[(4-butoxypyridin-2-yl)methyl]amino}-3-1H-imidazole-5-carboxamide (0.42 g, 1.45 mmol, obtained from Example 18(e)) in dichloromethane (10 mL) was added dropwise ethoxycarbonyl isothiocyanate (0.20 mL, 1.74 mmol). After stirring o.n., the solvent was evaporated in vacuo. To the residue was added 1N NaOH (7 mL) and the mixture was refluxed for 3 h. The reaction mixture was neutralized with 2N HCl producing a solid that was filtered and dried. The product was purified by recrystallization from DMSO/H$_2$O (0.060 g, 12% yield).

$^1$H NMR (DMSO-d$_6$) δ ppm 13.86 (1H), 12.55 (1H), 8.22 (1H), 8.10 (1H), 6.84 (1H), 6.71 (1H), 5.72 (2H), 4.01 (2H), 1.70-1.63 (2H), 1.44-1.37 (2H), 0.91 (3H); MS (ESI) m/z 332 (M+1).

Example 19

3-[(3-Butoxypyridin-2-yl)methyl]-2-thioxo-1,2,3,7-tetrahydro-6H-purin-6-one (a) 3-Butoxypyridine-2-carbaldehyde The title compound was made in a related procedure described by Daines, R. A. et al. (*J. Med. Chem.* 1993, 36, 3321-3332). To a solution of 2-hydroxy-pyridine-2-carbaldehyde (0.998 g, 8.11 mmol) in DMF (11.4 mL) was added 1-iodobutane (1.10 mL, 9.73 mmol) followed by anhydrous potassium carbonate (3.36 g, 24.3 mmol). After 1 h at 90° C., the solution was cooled to r.t. and poured into ethyl acetate. The organic layer was washed once with water, twice with brine and then was dried over sodium sulfate, filtered and concentrated in vacuo generating 1.31 g (90% yield, 7.30 mmol) of the title compound as a liquid. This material was used in the next step without further purification.

$^1$H NMR (CDCl$_3$) δ ppm 10.43 (1H), 8.39 (1H), 7.46 (1H), 7.41 (1H), 4.12 (2H), 1.91-1.84 (2H), 1.58-1.50 (2H), 1.00 (3H).

(b) 4-{[(3-Butoxypyridin-2-yl)methyl]amino}-1)-1H-imidazole-5-carboxamide

The title compound was prepared in accordance with the general method described in Example 17(e) using 3-butoxypyridine-2-carbaldehyde (1.30 g, 7.29 mmol, obtained from Example 19(a)), 5-aminoimidazole-4-carboxamide (0.613 g, 4.86 mmol), acetic acid (0.84 mL, 14.6 mmol) and sodium cyanoborohydride (0.916 g, 14.6 mmol) with the exception that the crude product was purified by silica gel column chromatography (dichloromethane/methanol, 99:1 to 80:20) resulting in 1.84 g of the title compound.

MS (ESI) m/z 290 (M+1).

(c) 3-[(3-Butoxypyridin-2-yl)methyl]-2-thioxo-1,2,3,7-tetrahydro-6H-purin-6-one

To 4-{[(3-butoxypyridin-2-yl)methyl]amino}-1H-imidazole-5-carboxamide (0.991 g, 3.43 mmol, obtained from Example 19(b)) was added dichloromethane (20 mL), ethoxycarbonyl isothiocyanate (0.47 mL, 4.11 mmol) and absolute ethanol (2 mL). After stirring o.n., more ethoxycarbonyl isothiocyanate (0.23 mL) was added and the solution was heated to reflux for 2 h upon, which more ethoxycarbonyl isothiocyanate (0.10 mL) was added and the solution was refluxed for 2 h more. The volatiles were removed in vacuo and 1 N sodium hydroxide (20 mL) was added and the suspension was heated to reflux for 4 h. After cooling to r.t. the solution was neutralized with 2 N hydrochloric acid. The resulting precipitate was filtered, washed with water and dried resulting in 0.699 g of crude product. Purification was achieved with a portion of the crude material (300 mg) by trituration with methanol and dichloromethane and then concentrating the organic layer followed by prep HPLC providing 0.103 g (16% yield, 0.231 mmol) of the title compound as its trifluoroacetic acid salt.

1H NMR (DMSO-d$_6$) δ ppm 12.50 (1H), 8.06 (s, 1H), 7.87 (1H), 7.44 (1H), 7.23 (1H), 5.78 (2H), 4.12 (2H), 1.80-1.73 (2H), 1.55-1.45 (2H), 0.97 (3H); $^{19}$F NMR (DMSO-D$_6$) δ ppm −74.9 (3F); MS (ESI) m/z 332 (M+H).

Example 20

3-[2-(Pyridin-2-ylmethoxy)propyl]-2-thioxo-1,2,3,7-tetrahydro-6H-purin-6-one (a)
2-[(2,2-Dimethoxy-1-methylethoxy)methyl]pyridine Sodium hydride (1.80 g, 45.0 mmol, 60% dispersion in mineral oil) was added slowly to a solution of 1,1-dimethoxypropan-2-ol (2.16 g, 18.0 mmol) (Prepared according to the method described by Hunter et al. *Tetrahedron*, 1994, 50, 871-888.) in DMF (25 mL) immersed in an ice bath. After the addition was complete, the ice bath was removed to allow the solution to warm to r.t. Then the reaction flask was placed in an ice bath and 2-picolylchloride hydrochloride (2.95 g, 18.0 mmol) was slowly added. After warming to r.t. overnight, diethyl ether, water and brine were added. The organic layer was separated and the aqueous layer was extracted with diethyl ether. The combined organic layers were dried over sodium sulfate, filtered and concentrated in vacuo. The product was purified by silica gel column chromatography (hexanes/ethyl acetate, first 4:1 then 1:1) resulting in the isolation of 1.74 g (46% yield, 8.22 mmol) of the title compound.

$^1$H NMR (CDCl$_3$) δ ppm 8.55-8.51 (1H), 7.69 (1H), 7.51 (1H), 7.19-7.16 (1H), 4.76 (2H), 4.27 (1H), 3.68-3.62 (1H), 3.45 (3H), 3.44 (3H), 1.24 (3H); MS (ESI) m/z 212 (M+1).

(b) 2-(Pyridin-2-ylmethoxy)-propanal

To a solution of 2-[(2,2-dimethoxy-1-methylethoxy)methyl]pyridine (1.66 g, 7.85 mmol, obtained from Example 20(a)) in THF (30 mL) was added water (10 mL) and concentrated sulfuric acid (1 mL) and the resulting solution was refluxed for 12 h. After cooling to r.t., the volatile components were removed in vacuo and dichloromethane was added followed by saturated sodium bicarbonate solution until the aqueous layer was pH 7. The layers were separated and the aqueous phase was extracted with dichloromethane. The organic layers were combined, dried over sodium sulfate, filtered and concentrated yielding 0.875 g (68% yield) of the title compound. This material was used in the next step without further purification.

$^1$H NMR (CDCl$_3$) δ ppm 9.74 (1H), 8.57 (1H), 7.73 (1H), 7.49 (1H), 7.23 (1H), 4.78 (1H), 4.73 (1H), 4.01 (1H), 1.39 (3H).

(c) 4-{([2-(Pyridin-2-ylmethoxy)propyl]amino}-1H-imidazole-5-carboxamide

The title compound was prepared in accordance with the general method described in Example 17(e) using 2-(pyridin-2-ylmethoxy)-propanal (0.875 g, 5.30 mmol, obtained from Example 20(b)), 5-aminoimidazole-4-carboxamide (0.668 g, 5.30 mmol), acetic acid (0.61 mL, 10.6 mmol) and sodium cyanoborohydride (0.666 g, 10.6 mmol) with the exception that the solution of aldehyde and carboxamide was stirred for 1 h and that sodium cyanoborohydride was added after 15 min. This yielded 1.32 g of the title compound, which was used in the next step without purification. MS (ESI) m/z 276 (M+1).

(d) 3-[2-(Pyridin-2-ylmethoxy)propyl]-2-thioxo-1,2,3,7-tetrahydro-6H-purin-6-one Ethoxycarbonyl isothiocyanate (0.246 mL, 2.18 mmol) was added to a suspension of 4-{[2-(pyridin-2-ylmethoxy)propyl]amino}-1H-imidazole-5-carboxamide (0.500 g, 1.82 mmol, obtained from Example 20(c)) in dichloromethane (10 mL). After 0.5 h, methanol (2 mL) was added. The solvent was removed in vacuo and acetone (5 mL) and another portion of ethoxycarbonyl isothiocyanate (0.246 mL, 2.18 mmol) were added. After o.n. stirring, the reaction was concentrated in vacuo. To the residue was added 1 N NaOH (10 mL) and the resulting solution was heated for 4 h at 100° C. After cooling to r.t., 2 N HCl was added until pH~6. The mixture was concentrated in vacuo. The product was purified by preparative HPLC resulting in 54.3 mg (9% yield) of the title compound.

¹H NMR (DMSO-d₆) δ ppm 12.43 (1H), 8.43-8.41 (1H), 8.13 (1H), 7.64 (1H), 7.23-7.20 (1H), 7.11 (1H), 4.74 (1H), 4.62 (1H), 4.44 (1H), 4.43 (1H), 4.38-4.31 (1H), 1.21 (3H); MS (ESI) m/z 318 (M+1).

Example 21

3-[(3,5-Dimethylisoxazol-4-yl)methyl]-2-thioxo-1,2,3,7-tetrahydro-6H-purin-6-one (a) 4-{[(3,5-Dimethylisoxazol-4-yl)methyl]amino}-1H-imidazole-5-carboxamide The title compound was prepared in accordance with the general method described in Example 17(e) using 3,5-dimethylisoxazole-4-carbaldehyde (0.50 g, 4.0 mmol), 5-amino-imidazole-4-carboxamide (0.50 g, 4.0 mmol), acetic acid (0.23 mL, 4.0 mmol) and sodium cyanoborohydride (0.30 g, 4.8 mmol) with the exception that after stirring o.n., more sodium cyanoborohydride (0.04 g, 0.6 mmol) was added and the reaction mixture refluxed for 2 h. The reaction mixture was then concentrated in vacuo and the crude product was triturated with ethyl ether and the solid removed by filtration. The filtrate was concentrated to give the title compound (0.91 g, 97% yield). This material was used in the next step without further purification. MS (ESI) m/z 236 (M+1).

(b) 3-[(3,5-Dimethylisoxazol-4-yl)methyl]-2-thioxo-1,2,3,7-tetrahydro-6H-purin-6-one Benzoyl isothiocyanate (0.62 mL, 4.64 mmol) was added, dropwise, to a solution of 4-{[(3,5-dimethylisoxazol-4-yl)methyl]amino}-1H-imidazole-5-carboxamide (0.91 g, 3.86 mmol, obtained from Example 21(a)) in acetone (20 mL). After stirring o.n., the solvent was evaporated in vacuo and the residue triturated with dichloromethane. The solid was removed by filtration and the filtrate was concentrated in vacuo. A solution of ammonia in methanol (7 N, 20 mL) was added to the resulting residue and this solution was transferred to a sealable tube. The vessel was sealed and placed in an 80° C. oil bath for 3 h. After cooling to r.t., the solution was concentrated in vacuo. The product was purified by recrystallization from DMSO/water, filtered and triturated sequentially with water, methanol and dichloromethane, providing the title compound (0.10 g, 10% yield) as a solid.
¹H NMR (DMSO-d₆) δ ppm 13.92 (1H), 12.56 (1H), 8.17 (1H), 5.47 (2H), 2.31 (3H), 2.15 (3H); MS (ESI) m/z 278 (M+1).

Example 22

3-[(1-Methyl-1H-indol-2-yl)methyl]-2-thioxo-1,2,3,7-tetrahydro-6H-purin-6-one (a) 4-{[1-Methyl-1H-indol-2-yl)methyl]amino}-1H-imidazole-5-carboxamide Triethylamine (0.47 mL, 3.4 mmol) was added to 5-amino-imidazole-4-carboxamide hydrochloride (0.50 g, 3.1 mmol) in anhydrous methanol (20 mL) and stirred at r.t. for 10 minutes. 1-Methylindole-2-carboxaldehyde (0.59 g, 3.7 mmol) was added followed by acetic acid (0.09 mL, 1.5 mmol). After stirring at r.t for 4 h, sodium cyanoborohydride (0.23 g, 3.7 mmol) was added and the mixture was stirred at r.t. overnight. Additional sodium cyanoborohydride (0.23 g, 3.7 mmol) was added and the mixture was stirred for two days at r.t., then at 50° C. overnight. The reaction mixture was concentrated in vacuo and the crude product was purified by flash chromatography (DCM/MeOH, 0 to 10%), giving the title compound (0.73 g, 89% yield) as an oil.
¹H NMR (DMSO-d₆) δ ppm 11.93-11.76 (1H), 7.45 (1H), 7.39 (1H), 7.09 (1H), 6.97 (1H), 6.79 (2H), 6.31 (1H), 4.62 (2H), 3.72 (3H); MS (ESI) m/z 270 (M+1).

(b) 3-[(1-Methyl-1H-indol-2-yl)methyl]-2-thioxo-1,2,3,7-tetrahydro-6H-purin-6-one Ethoxycarbonyl isothiocyanate (0.29 mL, 2.6 mmol) was added to a solution of 4-{[1-methyl-1H-indol-2-yl)methyl]amino}-1H-imidazole-5-carboxamide (obtained from Example 22(a)) in DCM/MeOH (9:1, 20 mL) and the mixture was stirred at r.t. for 1.5 h. The solvent was evaporated and the residue was dissolved in a solution sodium hydroxide (2% aq., 30 mL) and stirred at 60° C. for 2 h. After cooling to r.t. the mixture was neutralized with 4 N HCl. The precipitated product was collected by filtration. The crude product was purified by preparative HPLC, giving 0.049 g of the title compound (6% yield).
¹H NMR (DMSO-d₆) δ ppm 13.93 (1H), 11.03 (1H), 8.17 (s), 7.44 (1H), 7.37 (1H), 7.10 (1H), 6.96 (1H), 6.05 (1H), 5.89 (2H), 3.89 (3H); MS (ESI) m/z 312 (M+1).

Example 23

3-(2-Phenyl-2-pyridin-2-ylethyl)-2-thioxo-1,2,3,7-tetrahydro-6H-purin-6-one (a) 4-[(2-Phenyl-2-pyridin-2-ylethyl)amino]-1H-imidazole-5-carboxamide 5-Amino-imidazole-4-carboxamide hydrochloride (0.89 g, 5.5 mmol) and triethylamine (0.8 mL, 6.1 mmol) was stirred in anhydrous methanol (50 mL) for 15 min. Acetic acid (0.2 mL) and phenyl(pyridin-2-yl)acetaldehyde (1.6 g, 8 mmol) (Prepared according to a method described in Jpn. Kokai Tokkyo Koho (1982), 3 pp.; JP57072963) were added. The mixture was stirred for 5 h. A solution of saturated sodium hydrogencarbonate was added and most of the methanol was removed in vacuo. The mixture was extracted with ethyl acetate. The combined organic phases were dried over magnesium sulfate and concentrated. Purification by silica gel column chromatography (dichloromethane/ammonia (7 N in methanol), 0-10%) gave the imine intermediate as a yellow solid. This solid was dissolved in anhydrous methanol and platinum oxide (50 mg) was added. The mixture was shaken under a hydrogen atmosphere for 30 h. The catalyst was removed by filtration through celite and the filtrate concentrated. Silica gel column chromatography (dichloromethane/ammonia (7 N in methanol), 0-7%) gave 1.0 g (60% yield) of the title compound. MS (ESI) m/z 306 (M−1).

(b) 3-(2-phenyl-2-pyridin-2-ylethyl)-2-thioxo-1,2,3,7-tetrahydro-6H-purin-6-one

Ethoxycarbonyl isothiocyanate (0.12 mL, 0.99 mmol) was added to 4-[(2-phenyl-2-pyridin-2-ylethyl)amino]-1H-imidazole-5-carboxamide (0.28 g, 0.9 mmol, obtained from Example 23(a)) in dry dichloromethane (10 mL) and dry methanol (0.11 mL). The mixture was stirred for 5 h and then concentrated, redissolved in aqueous potassium hydroxide (1.2 N, 7 mL) and heated at 80° C. for 3 h. After cooling to r.t., pH was adjusted to 7 using hydrochloric acid (2 N). The mixture was filtered and the solid was purified using preparative HPLC, giving the title compound 36 mg (11% yield) as a solid.

$^1$H NMR (DMSO-d$_6$) δ ppm 13.61 (1H), 12.35 (1H), 8.51-8.55 (1H), 7.97 (1H), 7.63-7.69 (1H), 7.20-7.29 (4H), 7.07-7.18 (3H), 5.43-5.51 (1H), 5.24-5.29 (1H), 4.95-5.01 (1H); MS (ESI) m/z 348 (M−1).

Example 24

3-(Quinolin-4-ylmethyl)-2-thioxo-1,2,3,7-tetrahydro-6H-purin-6-one (a) 4-[(Quinolin-4-ylmethyl)amino]-1H-imidazole-4-carboxamide The title compound was prepared in accordance with the general method described in Example 17(e) using quinoline-4-carbaldehyde (1.0 g, 6.4 mmol), 5-aminoimidazole-4-carboxamide (0.80 g, 6.4 mmol), acetic acid (0.44 mL, 7.6 mmol) and sodium cyanoborohydride (0.48 g, 7.6 mmol) with the exception that after stirring o.n., another portion of sodium cyanoborohydride (0.48 g, 7.6 mmol) was added and the mixture heated to reflux for 4 h. After cooling to r.t., the solution was concentrated in vacuo. A portion of the 2.9 g of crude material obtained was used in the next step without further purification. MS (ESI) m/z 268 (M+1).

(b) 3-(Quinolin-4-ylmethyl)-2-thioxo-1,2,3,7-tetrahydro-6H-purin-6-one

Ethoxycarbonyl isothiocyanate (0.5 ml, 4.18 mmol) was added to a solution of 4-[(quinolin-4-ylmethyl)amino]-1H-imidazole-4-carboxamide (0.93 g, crude material from Example 24(a)) dissolved in anhydrous dichloromethane (10 mL) and methanol (5 mL) mixture. After o.n. (over night) at r.t., the solution was concentrated in vacuo and the residue was dissolved in 1N NaOH solution (30 mL) and refluxed for 3.5 h. After cooling to r.t., the pH was adjusted to ~6.5 with 2 N HCl. The solid that formed was collected by filtration and dried generating 0.35 g of crude material. A portion of the solid (150 mg) was purified by preparative HPLC, and the solid obtained was washed with dichloromethane and ether, generating 25.9 mg (9% yield over two steps) of the title compound.

$^1$H NMR (DMSO-d$_6$) δ 13.98 (1H), 12.69 (1H), 8.71 (1H), 8.32 (1H), 8.09 (1H), 8.06 (1H), 7.86-7.82 (1H), 7.75-7.70 (1H), 6.88 (1H), 6.23 (2H); MS (ESI) m/z 310 (M+1).

Example 25

3-[(6-Phenoxypyridin-3-yl)methyl]-2-thioxo-1,2,3,7-tetrahydro-6H-purin-6-one (a) 4-{[(6-Phenoxypyridin-3-yl)methyl]amino}-1H-imidazole-5-carboxamide Triethylamine (0.47 mL, 3.38 mmol) was added to 5-aminoimidazole-4-carboxamide hydrochloride (0.50 g, 3.1 mmol) in anhydrous methanol (12 mL). The reaction mixture was stirred for 10 min and 6-phenoxynicotinaldehyde (0.74 g, 3.7 mmol) and acetic acid (0.09 mL, 1.57 mmol) were added. The dark solution was stirred over night and sodium cyanoborohydride (0.23 g, 3.7 mmol) was added. More sodium cyanoborohydride (0.15 g, 2.4 mmol) was added after 40 min and the mixture was stirred for another 3 h. The reaction mixture was heated at 50° C. for 3 h, sodium cyanoborohydride (0.15 g, 2.4 mmol) was added and the mixture was heated at 50° C. over night. Sodium borohydride (0.12 g, 3.2 mmol) was added and the mixture was heated at 50° C. for 1 h, more sodium borohydride (0.15 g, 4.0 mmol) and NMP (1.0 mL) were added and the mixture was heated at 60° C. for 3.5 h. After cooling, NaHCO$_3$ (sat., 20 mL) was added and some of the methanol was removed in vacuo. The mixture was extracted with EtOAc, the organic phase was extracted with 1N HCl (2×30 mL) and the acidic phase was made basic with 2N NaOH and was extracted with DCM. The organic phase was dried over MgSO$_4$, filtered and concentrated. The crude product was purified by column chromatography on silica (0 to 10% MeOH in DCM+NH$_3$) to yield 0.25 g (0.81 mmol, 26%) of a slightly green syrup.

$^1$H NMR (CDCl$_3$) δ ppm 7.98 (1H) 7.68 (1H) 7.38 (2H) 7.18 (1H) 7.09 (2H) 6.99 (1H) 6.86 (1H) 6.46 (1H) 5.95 (2H) 4.37 (2H); MS (ESI) m/z 308 (M−1).

(b) 3-[(6-Phenoxypyridin-3-yl)methyl]-2-thioxo-1,2,3,7-tetrahydro-6H-purin-6-one Ethoxycarbonyl isothiocyanate (0.096 mL, 0.85 mmol) was added to 4-{[(6-phenoxypyridin-3-yl)methyl]amino}-1H-imidazole-5-carboxamide (0.25 g, 0.81 mmol, obtained from Example 25(a)) in anhydrous dichloromethane (3.0 mL). After stirring for 2.5 h at ambient temperature the mixture was concentrated to dryness. Sodium hydroxide (10 mL, 2% w/v) was added and the solution was heated at 50° C. over night. After cooling, the pH was adjusted to 4-5 using 2N HCl. The solid was collected by filtration and recrystallized from DMSO/water to give a white crystalline material. A portion of this material was recrystallized from MeOH to give 35 mg (0.10 mmol, 12% yield) of the title compound.

$^1$H NMR (DMSO-d$_6$) δ ppm 8.23 (1H) 8.17 (1H) 7.91 (1H) 7.39 (2H) 7.19 (1H) 7.09 (2H) 6.96 (1H) 5.67 (2H); MS (ESI) m/z 352 (M+1).

Example 26

3-{2-[(Quinolin-4-ylmethyl)amino]ethyl}-2-thioxo-1,2,3,7-tetrahydro-6H-purin-6-one (a) tert-Butyl {2-[(5-carbamoyl-1H-imidazol-4-yl)amino]ethyl}carbamate The reaction mixture of 5-amino-imidazole-4-carboxamide hydrochloride (10 g, 62 mmol) and triethylamine (8.7 mL, 63 mmol) in anhydrous methanol (100 mL) was stirred for 15 min. Acetic acid (0.9 mL, 16 mmol) and N-boc-2-aminoacetaldehyde (11 g, 67 mmol) were added. The reaction mixture was stirred for 3 h, then sodium cyanoborohydride (5 g, 80 mmol) was added and the mixture was stirred o.n. A solution of saturated sodium bicarbonate was added and most of the methanol was removed in vacuo. The mixture was extracted with ethyl acetate. The combined organic phases were dried over magnesium sulfate and concentrated. Purification by silica gel column chromatography, (dichloromethane/ammonia (7N in methanol), 0-6%) gave 9.2 g (55% yield) of the title compound.

$^1$H NMR (DMSO-d$_6$) δ ppm 6.87 (1H), 6.67 (2H), 3.25 (2H), 3.03-3.09 (2H), 1.37 (9H); MS (ESI) m/z 268 (M−1).

(b) 3-(2-Aminoethyl)-2-thioxo-1,2,3,7-tetrahydro-6H-purin-6-one trifluoroacetate Benzoyl isothiocyanate (1.3 mL, 9.8 mmol) was added to tert-butyl {2-[(5-carbamoyl-1H-imidazol-4-yl)amino]

ethyl}carbamate (2.5 g, 9.3 mmol, obtained from Example 26(a)) in dichloromethane (25 mL) and methanol (0.050 mL) at 0° C. The mixture was allowed to reach r.t. and stirred for 3 h. After removal of solvents, the residue was dissolved in ammonia (7 N in methanol, 30 mL) and subjected to microwave heating at 80° C. for 5 h. The solvent was then evaporated and the Boc-protected product was purified by silica gel column chromatography (dichloromethane/methanol 95:5) which gave 1.5 g (52% yield). This material (1.5 g, 4.9 mmol) was dissolved in dichloromethane (50 mL) and treated with trifluoroacetic acid (7 mL). After 2 h, the mixture was concentrated, diethyl ether was added and the solid was collected and dried in vacuo to afford 1.1 g (67% yield) of the title compound as its trifluoroacetic acid salt.

$^1$H NMR (DMSO-d$_6$) δ ppm 13.93 (1H), 12.57 (1H), 8.22 (1H), 4.76 (2H), 3.29 (2H); MS (ESI) m/z 210 (M−1).

(c) 3-{2-[(Quinolin-4-ylmethyl)amino]ethyl}-2-thioxo-1,2,3,7-tetrahydro-6H-purin-6-one 3-(2-Aminoethyl)-2-thioxo-1,2,3,7-tetrahydro-6H-purin-6-one trifluoroacetate (98 mg, 0.3 mmol, obtained from Example 26(b)) and triethylamine (0.043 mL, 0.31 mmol) was stirred in dry methanol for 15 min. 4-Quinoline carboxaldehyde (47 mg, 0.3 mmol) and acetic acid (3 drops) were added and the mixture was stirred o.n. Sodium cyanoborohydride (28 mg, 0.45 mmol) was added and the mixture was stirred for 5 h. The mixture was then concentrated and purified by preparative HPLC, giving 31 mg (29% yield) of the title compound $^1$H NMR (DMSO-d$_6$) δ ppm 12.39 (1H), 8.80 (1H), 8.11-8.17 (2H), 8.00 (1H), 7.71-7.77 (1H), 7.55-7.62 (1H), 7.49 (1H), 4.66 (2H), 4.28 (2H), 3.09 (2H); MS (ESI) m/z 351 (M−1).

Example 27

3-(2-{[(1-Methyl-1H-indol-3-yl)methyl]amino}ethyl)-2-thioxo-1,2,3,7-tetrahydro-6H-purin-6-one The title compound was prepared in accordance with the general method described in Example 26(c) by using 3-(2-aminoethyl)-2-thioxo-1,2,3,7-tetrahydro-6H-purin-6-one trifluoroacetate (98 mg, 0.3 mmol, obtained from Example 26(b)) and 1-methylindole-3-aldehyde (51 mg, 0.03 mmol) which yielded 0.021 g (20% yield) of the title compound.

$^1$H NMR (DMSO-d$_6$) δ ppm 7.96 (1H), 7.56-7.60 (1H), 7.36-7.39 (1H), 7.22 (1H), 7.11-7.16 (1H), 6.98-7.03 (1H), 4.66 (2H), 3.99 (2H), 3.73 (3H), 3.08 (2H); MS (ESI) m/z 353 (M−1).

Example 28

3-{2-[Methyl(quinolin-4-ylmethyl)amino]ethyl}-2-thioxo-1,2,3,7-tetrahydro-6H-purin-6-one (a) tert-Butyl methyl(2-oxoethyl)carbamate Dess-Martin periodinane (22 g, 52 mmol) was added in portions to 2-N-Boc-methylamino)ethanol (8.8 g, 50 mmol) in dicholoromethane at 0° C. The mixture was allowed to reach r.t. and stirred for 3 h. Saturated solutions of aqueous sodium hydrogencarbonate and sodium thiosulfate were added and the resulting solution stirred for is 0.5 h. The organic phase was separated and washed with saturated sodium hydrogencarbonate solution, dried over magnesium sulfate and concentrated to give 9 g (quantitative yield) of the title compound. GC-MS m/z 174 (M+1).

(b) tert-Butyl {2-[(5-carbamoyl-1H-imidazol-4-yl)amino]ethyl}methylcarbamate

The title compound was prepared in accordance with the general method described in Example 27(a) by using 5-amino-imidazole-4-carboxamide hydrochloride (5.7 g, 35 mmol, obtained from Example 28(a), triethylamime (5.3 mL, 39 mmol), tert-butyl methyl(2-oxoethyl)carbamate (9 g, 50 mmol), acetic acid (0.5 mL) and sodium cyanoborohydride (3.8 g, 60 mmol), which yielded 7.4 g (74% yield) of the title compound.

$^1$H NMR (CDCl$_3$) δ ppm 7.20 (1H), 3.35-3.41 (2H), 3.29-3.35 (2H), 2.94 (3H), 1.51 (9H); MS (ESI) m/z 282 (M−1).

(c) 3-[2-(Methylamino)ethyl]-2-thioxo-1,2,3,7-tetrahydro-6H-purin-6-one trifluoroacetate Ethoxycarbonyl isothiocyanate (0.67 mL, 5.7 mmol) was added to tert-butyl {2-[(5-carbamoyl-1H-imidazol-4-yl)amino]ethylmethylcarbamate (1.5 g, 5.3 mmol, obtained from Example 28(b)) in anhydrous dichloromethane (15 mL). The mixture was stirred for 1 h, concentrated and dissolved in aqueous sodium hydroxide (2 N, 15 mL) and then subjected to microwave heating at 120° C. for 15 min. The reaction mixture was adjusted to acidic pH by using hydrochloric acid (6 N). The precipitated solid was collected and dried, giving 1.8 g of material. This solid was dissolved in dichloromethane (15 mL) and treated with trifluoracetic acid (5 mL) for 1 h. The reaction mixture was concentrated and diethyl ether (40 mL) was added. The resulting solid was collected and dried, giving 0.93 g (52% yield) of the title compound.

$^1$H NMR (DMSO-d$_6$) δ ppm 13.96 (1H), 12.60 (1H), 8.22 (1H), 4.79 (2H), 3.40-3.42 (2H), 2.61 (3H); MS (ESI) m/z 224 (M−1).

(d) 3-{2-[Methyl(quinolin-4-ylmethyl)amino]ethyl}-2-thioxo-1,2,3,7-tetrahydro-6H-purin-6-one The title compound was prepared in accordance with the general method described in Example 26(c) by using 3-[2-(methylamino)ethyl]-2-thioxo-1,2,3,7-tetrahydro-6H-purin-6-one trifluoroacetate (0.10 g, 0.29 mmol, obtained from Example 28(c)), triethylamine (0.032 mL, 0.32 mmol), 4-quinoline carboxaldehyde (0.060 g, 0.38 mmol) and sodium cyanoborohydride (0.028 g, 0.44 mmol) which yielded 0.015 g (14% yield) of the title compound.

$^1$H NMR (DMSO-d$_6$) δ ppm 13.69 (1H), 12.28 (1H), 8.74 (1H), 8.00-8.05 (2H), 7.93-7.97 (1H), 7.64-7.69 (1H), 7.39-7.44 (1H), 7.34 (1H), 4.63 (2H), 3.97 (2H), 2.93 (2H), 2.38 (3H); MS (ESI) m/z 365 (M−1).

Example 29

3-(2-Aminopropyl)-2-thioxo-1,2,3,7-tetrahydro-6H-purin-6-one trifluoroacetate (a) tert-Butyl (1-methyl-2-oxoethyl-carbamate To a stirred solution of N-Boc-2-amino-1-propanol (1.8 g, 10 mmol) in dichloromethane (34 mL) was added tetrabutylammonium chloride (0.28 g, 1.0 mmol), TEMPO (0.16 g, 1.0 mmol), N-chlorosuccinimide (2.1 g, 15.4 mmol) and NaHCO$_3$/K$_2$CO$_3$ (0.5 N/0.05N, 34 mL). After 3 h, the organic layer was separated. The aqueous layer was extracted with dichloromethane. The combine organic layers were washed with brine, dried over sodium sulfate, filtered and concentrated. The crude product was purified by silica gel column chromatography (hexanes/ethyl acetate, 12:1 then 2:1) to give the title compound (0.95 g, 55% yield) as a white solid.

$^1$H NMR (CDCl$_3$) δ ppm 9.57 (1H), 5.18 (1H), 4.26-4.18 (1H), 1.46 (9H), 1.34 (3H).

(b) tert-Butyl {2-[(5-carbamoyl-1H-imidazol-4-yl)amino]-1-methylethyl}carbamate

To a stirred solution tert-butyl (1-methyl-2-oxoethyl-carbamate (0.82 g, 4.8 mmol, obtained from Example 29(a)) in ethanol (10 mL) was added 5-aminoimidazole-4-carboxamide (9.4 mL, 67 mmol). After 1 h, glacial acetic acid (0.28 mL, 4.0 mmol) was added. After another 1 h, sodium cyanoborohydride (0.48 g, 4.0 mmol) was added. After 20 h, the solvent was removed in vacuo. The product was purified by silica gel column chromatography (dichloromethane/methanol, 95:5 then 90:10) to give the title compound (0.95 g, 66% yield) as a solid.

$^1$H NMR (CDCl$_3$) δ ppm 7.17 (1H), 6.51 (1H), 4.71 (1H), 3.57-3.46 (1H), 3.40 (1H), 3.06-2.96 (1H), 1.48 (9H), 1.25 (3H); MS (ESI) m/z 284 (M+1).

(c) 3-(2-Aminopropyl)-2-thioxo-1,2,3,7-tetrahydro-6H-purin-6-one trifluoroacetate To a stirred solution tert-butyl {2-[(5-carbamoyl-1H-imidazol-4-yl)amino]-1-methylethyl}carbamate (0.70 g, 2.8 mmol, obtained from Example 29(b)) in dichloromethane (10 mL) was added dropwise benzoyl isothiocyanate (0.50 ml, 3.6 mmol). After stirring o.n., the precipitate was filtered and dried to give a white solid (0.69 g, 1.5 mmol). This solid was mixed with ammonia in methanol (7 N, 17 mL) in a sealable tube. The vessel was sealed and placed in an 80° C. oil bath for 3 h. After cooling to r.t., the solution was concentrated in vacuo. The product was purified by silica gel column chromatography (dichloromethane/ethyl acetate, 50 to 100%) to give the Boc protected compound (0.27 g, 54% yield). Part of this white solid (0.16 g, 0.50 mmol) was dissolved in trifluoroacetic acid and dichloromethane (1:1, 5 mL). After 2 at r.t., the volatiles were removed in vacuo. The residue was treated with dichloromethane and then concentrated. After repeating the dichloromethane treatment a second time dichloromethane was added and the precipitate that formed was filtered, dried in vacuo providing 0.15 g of crude product. The product was purified by preparative HPLC to give the title compound (0.08 g, 48% yield) as its trifluoroacetic acid salt.

$^1$H NMR (DMSO-d$_6$) δ ppm 13.95 (1H), 12.63 (1H), 8.23 (1H), 7.90 (3H), 4.70 (1H), 4.55 (1H), 3.94-3.84 (1H), 1.27 (3H); $^{19}$F NMR (DMSO-d$_6$) δ ppm -74 (3F); MS (ESI) m/z 226 (M+1).

General Method Used for Examples 30 to 56

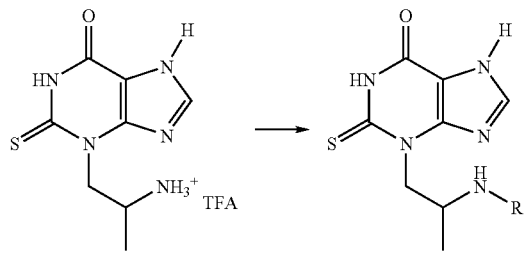

Aldehyde (0.33 mmol, 0.95 equiv.) and triethylamine (0.35 mmol, 1 equiv.) were added to a suspension of 3-(2-aminopropyl)-2-thioxo-1,2,3,7-tetrahydro-6H-purin-6-one (0.35 mmol, obtained from Example 18(c)) in anhydrous methanol (3 mL). After 15 min at r.t., the reaction mixture was concentrated in vacuo. The residue was suspended in anhydrous methanol (3 mL) and after 10 min, acetic acid (0.35 mmol, 1 equiv.) was added. After another 15 min, sodium cyanoborohydride (0.34 mmol, 0.97 equiv.) was added to the mixture. After o.n. at r.t., ten drops of trifluoroacetic acid or acetic acid were added and the reaction mixture was concentrated in vacuo. The product was purified by preparative HPLC, giving the desired compound after lyophilization. R is defined as R$^1$ for formula (I) above.

Example 30

3-{2-[(Pyridin-2-ylmethyl)amino]propyl}-2-thioxo-1,2,3,7-tetrahydro-6H-purin-6-one trifluoroacetate The title compound was synthesized in accordance with general method described above by using pyridine-2-carbaldehyde (27 μl, 0.28 mmol), which yielded 35 mg (27% yield, 0.081 mmol) of the title compound as the trifluoroacetic acid salt.

$^1$H NMR (DMSO-d$_6$) δ ppm 13.98 (1H), 12.63 (1H), 9.16 (2H), 8.59 (1H), 8.22 (1H), 7.89 (1H), 7.47 (1H), 7.43 (1H), 4.99 (1H), 4.63 (1H), 4.59 (1H), 4.38 (1H), 4.06 (1H), 1.39 (3H); MS (ESI) m/z 317 (M+H).

Example 31

3-{2-[Pyridin-3-ylmethyl)amino]propyl}-2-thioxo-1,2,3,7-tetrahydro-6H-purin-6-one The title compound was prepared in accordance with the general method described above by using pyridine-3-carbaldehyde (60 mg, 0.56 mmol) which generated 34 mg of the title compound (18% yield).

$^1$H NMR (DMSO-d$_6$) δ 12.39 (1H), 8.39 (1H), 8.38 (1H), 8.12 (1H), 7.59 (1H), 7.24 (1H), 4.58 (1H), 4.36 (1H), 3.84 (1H), 3.70 (1H), 3.42-3.34 (1H), 1.03 (3H); MS (ESI) m/z 317 (M+1).

Example 32

3-{2-[(Pyridin-4-ylmethyl)amino]propyl}-2-thioxo-1,2,3,7-tetrahydro-6H-purin-6-one The title compound was prepared in accordance with the general method described above by using 4-pyridinecarboxaldehyde (36 mg, 0.34 mmol), which yielded 52 mg (46% yield) of the title compound.

$^1$H NMR (DMSO-d$_6$) δ 12.37 (1H), 8.39-8.38 (2H), 8.10 (1H), 7.21-7.19 (2H), 4.57 (1H), 4.37 (1H), 3.84 (1H), 3.70 (1H), 3.40-3.35 (1H), 1.03 (3H); MS (ESI) m/z 317 (M+1).

Example 33

3-(2-{[(6-Chloropyridin-3-yl)methyl]amino}propyl)-2-thioxo-1,2,3,7-tetrahydro-6H-purin-6-one trifluoroacetate The title compound was prepared in accordance with the general method described above by using 6-chloropyridine-3-carbaldehyde (48 mg, 0.34 mmol), which yielded 27 mg (16% yield) of the desired product as the trifluoroacetic acid salt.

¹H NMR (DMSO-d$_6$) δ ppm 12.67 (1H), 9.07 (2H), 8.50 (1H), 8.25 (1H), 7.96 (1H), 7.64 (1H), 4.91 (1H), 4.67 (1H), 4.46 (1H), 4.32 (1H), 4.11-4.07 (1H), 1.36 (3H); ¹⁹F NMR (DMSO-d$_6$) δ ppm −73.8 (3F); MS (ESI) m/z 351 (M+1).

Example 34

3-[2-({[6-(Trifluoromethyl)pyridin-3-yl]methyl}amino)propyl]-2-thioxo-1,2,3,7-tetrahydro-6H-purin-6-one trifluoroacetate The title compound was synthesized in accordance with the general method described above by using 6-(trifluoromethyl)pyridine-3-carbaldehyde (59 mg, 0.34 mmol), which yielded 22 mg (12% yield) of the desired product as its trifluoroacetic acid salt.
¹H NMR (DMSO-d$_6$) δ ppm 12.67 (1H), 9.22 (2H), 8.84 (1H), 8.25 (1H), 8.20 (1H), 8.03 (1H), 4.90 (1H), 4.67 (1H), 4.61-4.50 (1H), 4.50-4.36 (1H), 4.20-4.12 (1H), 1.36 (3H). ¹⁹F NMR (DMSO-d$_6$) δ ppm −69.0 (3F), −73.8 (3F); MS (ESI) m/z 385 (M+1).

Example 35

3-(2-{[(4,6-Dichloropyrimidin-5-yl)methyl]amino}propyl)-2-thioxo-1,2,3,7-tetrahydro-6H-purin-6-one The title compound was prepared in accordance with the general method described above by using 4,6-dichloropyrimidine-5-carbaldehyde (87 mg, 0.49 mmol), which generated 135 mg of the product. Further purification of a portion of the material (60 mg) was accomplished by recrystallization from DMSO/water generating 55 mg (65% yield) of the title compound.
¹H NMR (DMSO-d$_6$) δ ppm 12.37 (1H), 8.72 (1H), 8.10 (1H), 4.55 (1H), 4.26 (1H), 3.89 (2H), 3.42-3.35 (1H), 1.11 (3H); MS (ESI) m/z 386 (M+1).

Example 36

3-[2-({[2-(Dimethylamino)pyrimidin-5-yl]methyl}amino)propyl]-2-thioxo-1,2,3,7-tetrahydro-6H-purin-6-one The title compound was prepared in accordance with the general method described above by using 2-dimethylaminopyrimidine-5-carbaldehyde (71 mg, 0.47 mmol), which after preparative HPLC and trituration with water and methanol yielded, 6.0 mg (3% yield) of the title compound.
¹H NMR (DMSO-d$_6$) δ ppm 8.11 (2H), 8.06 (1H), 4.56 (1H), 4.29 (1H), 3.62 (1H), 3.45 (1H), 3.41-3.39 (1H), 3.05 (6H), 0.99 (3H); MS (ESI) m/z 361 (M+1).

Example 37

3-{2-[(Quinolin-2-ylmethyl)amino]propyl}-2-thioxo-1,2,3,7-tetrahydro-6H-purin-6-one trifluoroacetate The title compound was synthesized in accordance with the general method described above by using 2-quinolinecarbaldehyde (53 mg, 0.34 mmol), which yielded 20 mg (12% yield) of the desired product as its trifluoroacetic acid salt.
¹H NMR (DMSO-d$_6$) δ ppm 13.99 (1H), 12.67 (1H), 9.22 (2H), 8.45 (1H), 8.29 (1H), 8.03 (1H), 7.98 (1H), 7.83 (1H), 7.66 (1H), 7.54 (1H), 5.04 (1H), 4.78 (1H), 4.69 (1H), 4.55 (1H), 4.13-4.09 (1H), 1.45 (3H); ¹⁹F NMR (DMSO-d$_6$) δ ppm −74.0 (3F); MS (ESI) m/z 370 (M+1).

Example 38

3-{2-[(Quinolin-3-ylmethyl)amino]propyl}-2-thioxo-1,2,3,7-tetrahydro-6H-purin-6-one The title compound was prepared in accordance with the general method described above by using quinoline-3-carbaldehyde (88 mg, 0.56 mmol), which generated 43 mg of the title compound (20% yield).
¹H NMR (DMSO-d$_6$) δ 12.35 (1H), 8.74 (1H), 8.08-8.05 (2H), 7.96 (1H), 7.84 (1H), 7.72-7.67 (1H), 7.59-7.54 (1H), 4.62 (1H), 4.40 (1H), 4.04 (1H), 3.89 (1H), 3.49-3.43 (1H), 1.07 (3H); MS (ESI) m/z 367 (M+1).

Example 39

3-(2-{[(1-tert-Butyl-3,5-dimethyl-1H-pyrazol-4-yl)methyl]amino}propyl)-2-thioxo-1,2,3,7-tetrahydro-6H-purin-6-one The title compound was synthesized in accordance with the general method described is above by using 1-tert-butyl-3,5-dimethyl-1H-pyrazol-4-carboxaldehyde (61 mg, 0.34 mmol), which yielded 25 mg (18% yield) of the desired product.
¹H NMR (DMSO-d$_6$) δ ppm 7.72 (1H), 4.52 (1H), 4.38 (1H), 3.48 (1H), 3.40-3.30 (2H), 2.15 (3H), 1.88 (3H), 1.47 (9H), 1.04 (3H); MS (ESI) m/z 390 (M+1).

Example 40

3-[2-({[1-(1,1-Dioxidotetrahydro-3-thienyl)-3,5-dimethyl-1H-pyrazol-4-yl]methyl}amino)propyl]-2-thioxo-1,2,3,7-tetrahydro-6H-purin-6-one The title compound was prepared in accordance with the general method described above by using 1-(1,1-dioxidotetrahydro-3-thienyl)-3,5-dimethyl-1H-pyrazole-4-carbaldehyde (114 mg, 0.47 mmol), which generated 128 mg of the product. Further purification was accomplished with a portion of this material (64 mg) by washing with water and dichloromethane, which after drying generated 34 mg (32% yield) of the title compound.
¹H NMR (DMSO-d$_6$) δ ppm 8.04 (1H), 5.09-5.01 (1H), 4.54 (1H), 4.32 (1H), 3.68-3.59 (1H), 3.53 (1H), 3.46-3.36 (1H), 3.33-3.15 (4H), 2.46-2.31 (2H), 2.09 (3H), 1.92 (3H), 1.07 (3H); MS (ESI) m/z 452 (M+1).

Example 41

3-{2-[(1H-Benzoimidazol-2-ylmethyl)amino]propyl}-2-thioxo-1,2,3,7-tetrahydro-6H-purin-6-one The title compound was synthesized in accordance with the general method described above by using 1H-benzoimidazol-2-carboxaldehyde (62 mg, 0.42 mmol), which yielded 8.3 mg (4% yield) of the desired product.
¹H NMR (DMSO-d$_6$) δ ppm 12.30 (1H), 8.06 (1H), 7.46-7.40 (2H), 7.12-7.07 (2H), 4.59 (1H), 4.42 (1H), 4.01 (1H), 3.96 (1H), 3.48-3.30 (2H), 1.03 (3H); MS (ESI) m/z 356 (M+1).

Example 42

3-[2-({[1-(Phenylsulfonyl)-1H-pyrrol-2-yl]methyl}amino]propyl]-2-thioxo-1,2,3,7-tetrahydro-6H-purin-6-one trifluoroacetate The title compound was prepared in accordance with the general method described above by using 1-(phenylsulfonyl)-2-pyrrolecarboxaldehyde (79 mg, 0.34 mmol), which yielded 121 mg (61% yield) of the desired product as its trifluoroacetic acid salt.

$^1$H NMR (DMSO-$d_6$) δ ppm 14.05 (1H), 12.66 (1H), 9.20 (1H), 8.90 (1H), 8.23 (1H), 7.97 (2H), 7.73 (1H), 7.66 (2H), 7.56 (1H), 6.48 (1H), 6.40 (1H), 4.88 (1H), 4.71 (1H), 4.60-4.47 (2H), 4.15-4.05 (1H), 1.36 (3H); MS (ESI) m/z 445 (M+1).

Example 43

3-{2-[({1-[(4-methylphenyl)sulfonyl]-1H-pyrrol-2-yl}methyl)amino]propyl}-2-thioxo-1,2,3,7-tetrahydro-6H-purin-6-one trifluoroacetate The title compound was synthesized in accordance with the general method described above by using 1-[(4-methylphenyl)sulfonyl]-1H-pyrrole-2-carbaldehyde (84 mg, 0.34 mmol), which yielded the title compound as the trifluoroacetic acid salt (92 mg, 46% yield).

$^1$H NMR (DMSO-$d_6$) δ 14.02 (1H), 12.69 (1H), 9.14 (1H), 8.48 (1H), 8.26 (1H), 7.88 (2H), 7.57-7.55 (1H), 7.47 (2H), 6.48-6.47 (1H), 6.40 (1H), 4.89 (1H), 4.72 (1H), 4.54-4.51 (2H), 4.11 (1H), 2.39 (3H), 1.37 (3H); $^{19}$F (DMSO-$d_6$) δ −74.01 (3F); MS (ESI) m/z 459 (M+1).

Example 44

3-(2-{[(1-methyl-1H-pyrrol-2-yl)methyl]amino}propyl)-2-thioxo-1,2,3,7-tetrahydro-6H-purin-6-one The title compound was prepared in accordance with the general method described above by using 1-methyl-1H-pyrrole-2-carbaldehyde (37 mg, 0.34 mmol), which yielded 44 mg (35% yield) of the desired compound.

$^1$H NMR (DMSO-$d_6$) δ 8.06 (1H), 6.53 (1H), 5.77-5.74 (2H), 4.56 (1H), 4.35 (1H), 3.73 (1H), 3.55 (1H), 3.45-3.42 (1H), 3.40 (3H), 1.02 (3H); MS (ESI) m/z 319 (M+1).

Example 45

3-[2-({[1-(4-sec-Butylphenyl)-1H-pyrrol-2-yl]methyl}amino)propyl)-2-thioxo-1,2,3,7-tetrahydro-6H-purin-6-one The title compound was prepared in accordance with the general method described above by using 1-(4-sec-butylphenyl)-1H-pyrrole-2-carbaldehyde (77 mg, 0.34 mmol), which generated 26 mg of the title compound (16% yield).

$^1$H NMR (DMSO-$d_6$) δ 12.42 (1H), 8.12 (1H), 7.31 (2H), 7.17 (2H), 6.82 (1H), 6.06-6.03 (2H), 4.48 (1H), 4.29 (1H), 3.75-3.65 (1H), 3.46-3.38 (2H), 2.64-2.56 (1H), 1.58-1.52 (2H), 1.19 (3H), 0.98 (3H), 0.77 (3H); MS (ESI) m/z 437 (M+1).

Example 46

3-[2-({[1-(3-Methoxyphenyl)-1H-pyrrol-2-yl]methyl}amino)propyl]-2-thioxo-1,2,3,7-tetrahydro-6H-purin-6-one The title compound was prepared in accordance with the general method described above by using 1-(3-methoxyphenyl)-1H-pyrrole-2-carbaldehyde (113 mg, 0.56 mmol), which generated 55 mg (23% yield) of the title compound.

$^1$H NMR (DMSO-$d_6$) δ 12.36 (1H), 8.10 (1H), 7.26 (1H), 7.04 (1H), 6.70-6.96 (1H), 6.88-6.85 (2H), 6.07-6.03 (2H), 4.48 (1H), 4.32 (1H), 3.78 (3H), 3.74 (1H), 3.54 (1H), 3.41-3.34 (1H), 0.99 (3H); MS (ESI) m/z 411 (M+1).

Example 47

3-[2-({[2,5-Dimethyl-1-(1,3-thiazol-2-yl)-1H-pyrrol-3-yl]methyl}amino)propyl]-2-thioxo-1,2,3,7-tetrahydro-6H-purin-6-one The title compound was prepared in accordance with the general method described above by using 2,5-dimethyl-1-thiazol-2-yl-1H-pyrrole-3-carbaldehyde (116 mg, 0.56 mmol), which generated 50 mg of the title compound (20% yield).

$^1$H NMR (DMSO-$d_6$) δ 7.93 (1H), 7.85 (1H), 7.81 (1H), 5.79 (1H), 4.66 (1H), 4.44 (1H), 3.68 (1H), 3.58-3.48 (2H), 2.05 (3H), 1.99 (3H), 1.10 (3H); MS (ESI) m/z 416 (M+1).

Example 48

3-[2-({[4-(3-Chlorobenzoyl)-1-methyl-1H-pyrrol-2-yl]methyl}amino)propyl]-2-thioxo-1,2,3,7-tetrahydro-6H-purin-6-one The title compound was prepared in accordance with the general method described above by using 4-(3-chlorobenzoyl)-1-methyl-1H-pyrrole-2-carbaldehyde (117 mg, 0.47 mmol), is which generated 127 mg of impure material. The desired compound was further purified by washing 65 mg of impure material with water and ether yielding 38 mg (35% yield) of the title compound.

$^1$H NMR (DMSO-$d_6$) δ ppm 12.40 (1H), 8.11 (1H), 7.66-7.63 (3H), 7.55-7.51 (1H), 7.32 (1H), 6.32 (1H), 4.58 (1H), 4.35 (1H), 3.79 (1H), 3.61 (1H), 3.53 (3H), 3.48-3.41 (1H), 1.05 (3H); MS (ESI) m/z 457 (M+1).

Example 49

3-{2-[(1H-Imidazol-2-ylmethyl)amino]propyl}-2-thioxo-1,2,3,7-tetrahydro-6H-purin-6-one The title compound was synthesized in accordance with the general method described above by using imidazole-2-carbaldehyde (32 mg, 0.34 mmol), which yielded 35 mg of the desired product (25% yield).

$^1$H NMR (DMSO-$d_6$) δ ppm 7.93 (1H), 6.83 (2H), 4.51-4.47 (1H), 4.41-4.35 (1H), 3.80-3.68 (2H), 3.45-3.35 (1H), 0.97 (3H); MS (ESI) m/z 306 (M+1).

Example 50

3-(2-{[(1-Methyl-1H-imidazol-2-yl)methyl]amino}propyl)-2-thioxo-1,2,3,7-tetrahydro-6H-purin-6-one The title compound was prepared in accordance with the general method described above by using 1-methyl-1H-imidazole-2-carbaldehyde (52 mg, 0.47 mmol), which generated 30 mg of the title compound (20% yield).

$^1$H NMR (DMSO-d$_6$) δ ppm 12.38 (1H), 8.10 (1H), 6.95 (1H), 6.65 (1H), 4.55 (1H), 4.34 (1H), 3.81 (1H), 3.68 (1H), 3.47 (3H), 3.40-3.37 (1H), 1.03 (3H); MS (ESI) m/z 320 (M+1).

Example 51

3-(2-{[(4-Bromo-1-methyl-1H-imidazol-5-yl)methyl]amino}propyl)-2-thioxo-1,2,3,7-tetrahydro-6H-purin-6-one The title compound was prepared in accordance with the general method described above by using 4-bromo-1-methyl-1H-imidazole-5-carbaldehyde (106 mg, 0.56 mmol), which generated 22 mg (9% yield) of the title compound.

$^1$H NMR (DMSO-d$_6$) δ ppm 12.41 (1H), 8.12 (1H), 7.47 (1H), 4.54 (1H), 4.31 (1H), 3.70 (1H), 3.59 (1H), 3.46 (3H), 3.34-3.31 (1H), 1.05 (3H); MS (ESI) m/z 398 (M+1).

Example 52

3-(2-{[(1-Methyl-1H-indol-3-yl)methyl]amino}propyl)-2-thioxo-1,2,3,7-tetrahydro-6H-purin-6-one The title compound was prepared in accordance with the general method described above by using 1-methyl-1H-indole-3-carbaldehyde (87 mg, 0.55 mmol), which after preparative HPLC generated 100 mg of impure product. Further purification of a portion of the impure material (41 mg) was accomplished by washing with water and methanol yielding 39 mg (47% yield) of the title compound.

$^1$H NMR (DMSO-d$_6$) δ ppm 7.88 (1H), 7.41 (1H), 7.34 (1H), 7.12-7.07 (2H), 6.93 (1H), 4.65 (1H), 4.44 (1H), 4.02 (1H), 3.87 (1H), 3.68 (3H), 3.57-3.52 (1H), 1.08 (3H); MS (ESI) m/z 369 (M+1).

Example 53

2-Thioxo-3-{2-[(1H-1,2,3-triazol-5-ylmethyl)amino]propyl}-1,2,3,7-tetrahydro-6H-purin-6-one The title compound was prepared in accordance with the general method described above by using 1H-1,2,3-triazole-5-carbaldehyde (54 mg, 0.56 mmol), which generated 25 mg of the title compound (14% yield).

$^1$H NMR (DMSO-d$_6$) δ 12.37 (1H), 8.11 (1H), 7.51 (1H), 4.54 (1H), 4.38 (1H), 3.89 (1H), 3.78 (1H), 3.45-3.34 (1H), 1.02 (3H); MS (ESI) m/z 307 (M+1).

Example 54

3-[2-({[1-(Benzyloxy)-1H-imidazol-2-yl]methyl}amino)propyl]-2-thioxo-1,2,3,7-tetrahydro-6H-purin-6-one The title compound was prepared in accordance with the general method described above by using 1-benzyloxy-1H-imidazole-2-carbaldehyde (40 mg, 0.20 mmol), which generated is 40 mg (40% yield) of the title compound.

$^1$H NMR (DMSO-d$_6$) δ 12.36 (1H), 8.09 (1H), 7.43-7.36 (3H), 7.33-7.31 (2H), 7.23 (1H), 6.63 (1H), 5.13 (1H), 5.10 (1H), 4.53 (1H), 4.33 (1H), 3.63 (1H), 3.53 (1H), 3.43-3.34 (1H), 1.01 (3H); MS (ESI) m/z 412 (M+1).

Example 55

3-(2-{[(6-Bromo-2-methylimidazo[1,2-a]pyridin-3-yl)methyl]amino}propyl}-2-thioxo-1,2,3,7-tetrahydro-6H-purin-6-one The title compound was prepared in accordance with the general method described above using 3-(2-aminopropyl)-2-thioxo-1,2,3,7-tetrahydro-6H-purin-6-one (60 mg, 0.18 mmol, obtained from Example 29(c)) and 6-bromo-2-methylimidazo[1,2-a]pyridine-3-carbaldehyde (33.8 mg, 0.14 mmol), with the exception that the imine formation was allowed to run for 48 h, which generated 15 mg (24% yield) of the title compound.

$^1$H NMR (DMSO-d$_6$) δ ppm 12.22 (1H), 8.31 (1H), 7.99 (1H), 7.33 (1H), 7.2 (1H), 4.55 (1H), 4.25 (1H), 4.08 (1H), 3.95 (1H), 3.42-3.39 (1H), 2.27 (3H), 1.07 (3H); MS (ESI) m/z 448 (M+1).

Example 56

3-{2-[({1-[2-(2-Methoxyphenoxy)ethyl]-1H-pyrrol-2-yl}methyl)amino]propyl]-2-thioxo-1,2,3,7-tetrahydro-6H-purin-6-one The title compound was prepared in accordance with the general method described above using 3-(2-aminopropyl)-2-thioxo-1,2,3,7-tetrahydro-6H-purin-6-one (0.18 g, 0.54 mmol, obtained from Example 29(c)) and 1-[2-(2-methoxyphenoxy)ethyl]-1H-pyrrole-2-carbaldehyde (125.8 mg; 0.513 mmol), which after preparative HPLC generated 0.17 g of the product. Further purification was accomplished with a portion of this material (0.76 g) by trituration with water, which after drying in vacuo, generated 30.0 mg (29% yield) of the title compound.

$^1$H NMR (DMSO-d$_6$) δ ppm 12.37 (1H), 8.09 (1H), 6.95-6.93 (1H), 6.93-6.83 (3H), 6.75-6.73 (1H), 5.84 (1H), 5.79-5.76 (1H), 4.59 (1H), 4.38 (1H), 4.20 (2H), 4.11 (2H), 3.87 (1H), 3.73 (3H), 3.70 (1H), 3.50-3.45 (1H), 1.04 (3H); MS (ESI) m/z 453 (M−1).

General Method Used for Examples 57 to 63

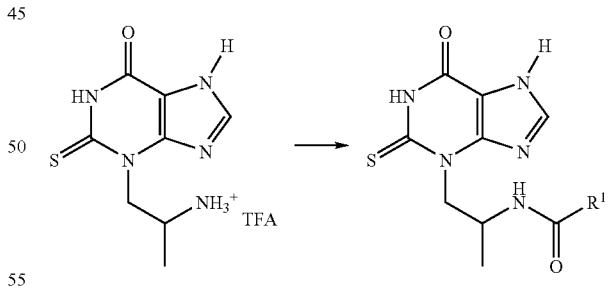

wherein R$^1$ is defined as in formula (I) above.

O-Benzotriazol-1-yl-N,N,N,N-tetramethyluronium tetrafluoroborate (0.35 mmol) was added to a solution of the carboxylic acid (0.35 mmol) in anhydrous DMF (3 mL), followed by addition of diisopropylethylamine (1.2 mmol). After 10 min. at room temperature, 3-(2-aminopropyl)-2-thioxo-1,2,3,7-tetrahydro-6H-purin-6-one (120 mg, 0.35 mmol, obtained from Example 29(c)) was added. After 1 h at r.t., the reaction mixture was concentrated in vacuo. The residue was suspended in dichloromethane and 34 drops of trifluoroacetic acid was added. The resulting mixture was concentrated or filtered and the desired product was purified by preparative HPLC or by recrystallization.

Example 57

N-[1-Methyl-2-(6-oxo-2-thioxo-1,2,6,7-tetrahydro-3H-purin-3-yl)ethyl]pyridine-2-carboxamide The title compound was synthesized in accordance with the general method described above by using 2-picolinic acid (44 mg, 0.35 mmol), which yielded 50 mg (43% yield) of the desired product as white powder after purification by preparative HPLC.

$^1$H NMR (DMSO-$d_6$) δ ppm 13.74 (1H), 12.44 (1H), 8.70 (1H), 8.57 (1H), 8.10 (1H), 7.92 (1H), 7.84 (1H), 7.57-7.52 (1H), 4.82-4.77 (2H), 4.59 (11), 1.28 (3H); MS (ESI) m/z 331 (M+1).

Example 58

N-[1-Methyl-2-(6-oxo-2-thioxo-1,2,6,7-tetrahydro-3H-purin-3-yl)ethyl]nicotinamide The title compound was prepared in accordance with the general method described above by using nicotinic acid (44 mg, 0.35 mmol). The crude compound was purified by trituration is with water, methanol and then dichloromethane and the resulting solid was then dissolved in DMSO (~10 mL) and precipitated by addition of water (~4 mL). After filtering and washing with water the compound was dried in vacuo generating 65 mg (56% yield) of the title compound.

$^1$H NMR (DMSO-$d_6$) δ ppm 13.73 (1H), 12.41 (1H), 8.77 (1H), 8.64 (1H), 8.52 (1H), 8.10 (1H), 7.96 (1H), 7.43 (1H), 4.84-4.79 (1H), 4.73 (1H), 4.56 (1H), 1.26 (3H); MS (ESI) m/z 331 (M+1).

Example 59

N-[1-Methyl-2-(6-oxo-2-thioxo-1,2,6,7-tetrahydro-3H-purin-3-yl)-ethyl]isonicotinamide The title compound was prepared in accordance with the general method described above by using isonicotinic acid (44 mg, 0.35 mmol). Purification was accomplished by trituration with dichloromethane yielding 54 mg (46% yield) of the title compound.

$^1$H NMR (DMSO-$d_6$) δ 13.73 (1H), 12.43 (1H), 8.66-8.64 (2H), 8.62 (1H), 8.11 (1H), 7.55-7.53 (2H), 4.85-4.77 (1H), 4.72 (1H), 4.57 (1H), 1.26 (3H); MS (ESI) m/z 331 (M+1).

Example 60

N-[1-methyl-2-(6-oxo-2-thioxo-1,2,6,7-tetrahydro-3H-purin-3-yl)ethyl]-1,8-naphthyridine-2-carboxamide The title compound was prepared in accordance with the general method described above by using 1,8-naphthyridine-2-carboxylic acid (62 mg, 0.35 mmol). The product was purified by recrystallization from DMSO/$H_2O$, filtering and washing the solid with water, methanol and dichloromethane and then drying in vacuo, which provided 40 mg (30% yield) of the title compound.

$^1$H NMR (DMSO-$d_6$) δ ppm 12.43 (1H), 9.21 (1H), 8.98 (1H), 8.61 (1H), 8.56 (1H), 8.07 (1H), 8.04 (1H), 7.73 (1H), 4.90-4.81 (2H), 4.66 (1H), 1.36 (3H); MS (ESI) m/z 382 (M+1).

Example 61

N-[1-Methyl-2-(6-oxo-2-thioxo-1,2,6,7-tetrahydro-3H-purin-3-yl)ethyl]quinoline-2-carboxamide The title compound was prepared in accordance with the general method described above by using quinoline-2-carboxylic acid (61 mg, 0.35 mmol), which yielded the title compound (45 mg, 34%) after purification by preparative HPLC.

$^1$H NMR (DMSO-$d_6$) δ ppm 12.43 (1H), 8.97 (1H), 8.49 (1H), 8.18 (1H), 8.14 (1H), 8.05 (1H), 7.98 (1H), 7.87 (1H), 7.71 (1H), 4.88 (1H), 4.81-4.74 (1H), 4.65 (1H), 1.35 (3H); MS (ESI) m/z 381 (M+1).

Example 62

N-[1-Methyl-2-(6-oxo-2-thioxo-1,2,6,7-tetrahydro-3H-purin-3-yl)ethyl]pyrimidine-2-carboxamide The title compound was prepared in accordance with the general method described above by using pyrimidine-2-carboxylic acid (28 mg, 0.23 mmol). Purification of the 60 mg of crude was accomplished by precipitation from DMSO/water, collecting the precipitate and then washing it with water and methanol. The material was then treated with water and the suspension was sonicated to separate water-soluble impurities from the desired compound. After filtering and drying 17 mg (22% yield, 0.051 mmol) of the title compound was obtained.

1H NMR (DMSO-$D_6$) δ ppm 12.43 (1H), 8.89 (2H), 8.84 (1H), 8.09 (1H), 7.64 (1H), 4.83-4.71 (2H), 4.62-4.58 (1H), 1.29 (3H); MS (ESI) m/z 332 (M+H).

Example 63

N-[1-Methyl-2-(6-oxo-2-thioxo-1,2,6,7-tetrahydro-3H-purin-3-yl)ethyl]-1H-imidazole-2-carboxamide trifluoroacetate The title compound was synthesized in accordance with the general method described above by using 1H-imidazole-2-carboxylic acid (40 mg, 0.35 mmol), which yielded 47 mg (30% yield) of the desired product as the trifluoroacetic acid salt, after purification by preparative HPLC.

$^1$H NMR (DMSO-$d_6$) δ ppm 13.76 (1H), 12.87 (1H), 12.45 (1H), 8.17-8.10 (2H), 7.05 (2H), 4.82-4.75 (2H), 4.55 (1H), 1.26 (3H); MS (ESI) m/z 320 (M+1).

Screens

Methods for the determination of MPO inhibitory activity are disclosed in patent application WO 02/090575. The pharmacological activity of compounds according to the invention was tested in the following screen in which the compounds were either tested alone or in the presence of added tyrosine:

Assay buffer: 20 mM sodium/potassium phosphate buffer pH 6.5 containing 10 mM taurine and 100 mM NaCl.

Developing reagent: 2 mM 3,3',5,5'-tetramethylbenzidine (TMB), 200 μM KI, 200 mM acetate buffer pH 5.4 with 20% DMF.

To 10 μl of diluted compounds in assay buffer, 40 μl of human MPO (final concentration 2.5 nM), with or without 20 μM tyrosine (final concentration, if present, 8 μM), was added and the mixture was incubated for 10 minutes at ambient temperature. Then 50 μl of $H_2O_2$ (final concentration 100 μM), or assay buffer alone as a control, were added. After incubation for 10 minutes at ambient temperature, the reaction was stopped by adding 10 μl 0.2 mg/ml of catalase (final concentration 18 μg/ml). The reaction mixture was left for an additional 5 minutes before 100 μl of TMB developing reagent was added. The amount of oxidised 3,3',5,5'-tetramethylbenzidine formed was then measured after about 5 minutes using absorbance spectroscopy at about 650 nM. $IC_{50}$ values were then determined using standard procedures.

When tested in at least one version of the above screen, the compounds of Examples 1 to 51 gave $IC_{50}$ values of less than 60 μM, indicating that they are expected to show useful therapeutic activity. Representative results are shown in the following Table.

| Compound | Inhibition of MPO (in the presence of tyrosine) $IC_{50}$ μM |
| --- | --- |
| Example 3 | 0.1 |
| Example 9 | 10 |
| Example 44 | 2.2 |

The invention claimed is:
1. A compound of Formula (I) or a pharmaceutically acceptable salt thereof:

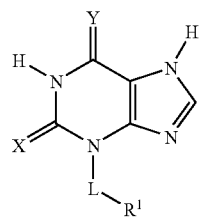

I wherein
at least one of X and Y is S, and the other is O or S;
L is ethylene, methylene, —$CH_2CH(CH_3)OCH_2$—, —$CH_2CH(C_6H_5)$—, —$CH_2CH_2NHCH_2$—, —$CH_2CH_2N(CH_3)CH_2$—, —$CH_2CH(CH_3)NHCH_2$—, or —$CH_2CH(CH_3)NHC(O)$—;
$R^1$ selected from indole, isoindole, benzimidazole, quinoline, naphthyridine, imidazo[1,2-a]pyridine, pyrazole, pyrazine, oxadiazole, pyridine, isoxazole, pyrimidine, pyrrole, imidazole, furazan and triazole; wherein each $R^1$ is independently and optionally substituted with one or more substituents independently selected from halogen, $CHF_2$, $CH_2F$, $CF_3$, $SO_{(n)}R^9$, $SO_{(n)}NR^9R^{10}$, $(CH_2)_nR^3$, $NR^4R^5$, OH, C1 to 7 alkyl, C1 to 7 alkoxy, phenoxy, aryl, CN, $C(O)NR^2R^3$, $NR^2C(O)R^3$, $C(O)R^3$, a 5- or 6-membered saturated or partially saturated ring containing one or more atoms selected from C, N, O, and S, and a mono- or bicyclic heteroaromatic ring system containing one or more heteroatoms selected from N, S, and O; and wherein said C1 to 7 alkoxy is optionally substituted with C1 to 6 alkoxy or aryl; wherein said C1 to 7 alkyl is optionally substituted with hydroxy or C1 to 6 alkoxy; wherein said C1 to 7 alkyl is optionally incorporating a carbonyl at any position in the C1 to 7 alkyl; and wherein said phenoxy is optionally substituted with C1 to 6 alkyl, halogen or C1 to 6 alkoxy;
at each occurrence, $R^2$, $R^3$, $R^4$, $R^5$, $R^9$ and $R^{10}$ are independently selected from hydrogen, C1 to 6 alkyl, C1 to 6 alkoxy, aryl, and phenoxy; and said C1 to 6 alkyl is optionally substituted with halogen, C1 to 6 alkoxy, CHO, C2 to 6 alkanoyl, OH, $C(O)NR^7R^8$ or $NR^7C(O)R^8$; and said aryl or said phenoxy is optionally substituted with C1 to 6 alkyl, halogen or C1 to 6 alkoxy;
or the groups $NR^2R^3$, $NR^4R^5$ and $NR^9R^{10}$ each independently represents a 5 to 7 membered saturated azacyclic ring optionally incorporating one additional heteroatom selected from O, S and $NR^{11}$, said ring being optionally further substituted with halogen, C1 to 6 alkoxy, CHO, C2 to 6 alkanoyl, OH, $C(O)NR^7R^8$ or $NR^7C(O)R^8$;
at each occurrence $R^7$, $R^8$ and $R^{11}$ independently represent hydrogen or C1 to 6 alkyl, or the group $NR^7R^8$ represents a 5 to 7 membered saturated azacyclic ring optionally incorporating one additional heteroatom selected from O, S, and $NR^{11}$; and
n is 0, 1 or 2.
2. A compound according to claim 1, wherein X is S and Y is O.
3. A pharmaceutical composition comprising a compound according to claim 1, or a pharmaceutically acceptable salt thereof, optionally in admixture with a pharmaceutically acceptable adjuvant, diluent or carrier.
4. A compound selected from:
3-(pyridin-2-ylmethyl)-2-thioxo-1,2,3,7-tetrahydro-6H-purin-6-one;
3-(pyridin-3-ylmethyl)-2-thioxo-1,2,3,7-tetrahydro-6H-purin-6-one;
3-(pyridin-4-ylmethyl)-2-thioxo-1,2,3,7-tetrahydro-6H-purin-6-one;
3-{[3-ethoxy-4-(2-ethoxyethoxy)pyridin-2-yl]methyl}-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(2-butyl-4-chloro-1H-imidazol-5-yl)methyl]-2-thioxo-1,2,3,7-tetrahydro-6H-purin-6-one;
3-(1H-benzimidazol-2-ylmethyl)-2-thioxo-1,2,3,7-tetrahydro-6H-purin-6-one;
3-[1-(1H-benzimidazol-2-yl)ethyl]-2-thioxo-1,2,3,7-tetrahydro-6H-purin-6-one;
3-[(5-chloro-1H-indol-3-yl)methyl]-2-thioxo-1,2,3,7-tetrahydro-6H-purin-6-one; and
3-[(4-fluoro-1H-indol-3-yl)methyl]-2-thioxo-1,2,3,7-tetrahydro-6H-purin-6-one;
or a pharmaceutically acceptable salt thereof.
5. A pharmaceutical composition comprising a compound according to claim 4, or a pharmaceutically acceptable salt thereof, optionally in admixture with a pharmaceutically acceptable adjuvant, diluent or carrier.
6. A compound selected from:
3-[2-(1H-Benzimidazol-2-yl)ethyl]-2-thioxo-1,2,3,7-tetrahydro-6H-purin-6-one;
3-(1H-Pyrazol-3-ylmethyl)-2-thioxo-1,2,3,7-tetrahydro-6H-purin-6-one;
3-[(5-Methylpyrazin-2-yl)methyl]-2-thioxo-1,2,3,7-tetrahydro-6H-purin-6-one;
3-[(3-Isopropylisoxazol-5-yl)methyl]-2-thioxo-1,2,3,7-tetrahydro-6H-purin-6-one;
3-[(4-Methyl-1,2,5-oxadiazol-3-yl)methyl]-2-thioxo-1,2,3,7-tetrahydro-6H-purin-6-one;
3-[(6-Butoxypyridin-2-yl)methyl]-2-thioxo-1,2,3,7-tetrahydro-6H-purin-6-one;
3-[(4-Butoxypyridin-2-yl)methyl]-2-thioxo-1,2,3,7-tetrahydro-6H-purin-6-one;
3-[(3-Butoxypyridin-2-yl)methyl]-2-thioxo-1,2,3,7-tetrahydro-6H-purin-6-one;

3-[2-(Pyridin-2-ylmethoxy)propyl]-2-thioxo-1,2,3,7-tetrahydro-6H-purin-6-one;
3-[(3,5-Dimethylisoxazol-4-yl)methyl]-2-thioxo-1,2,3,7-tetrahydro-6H-purin-6-one;
3-[(1-Methyl-1H-indol-2-yl)methyl]-2-thioxo-1,2,3,7-tetrahydro-6H-purin-6-one;
3-(2-Phenyl-2-pyridin-2-ylethyl)-2-thioxo-1,2,3,7-tetrahydro-6H-purin-6-one;
3-(Quinolin-4-ylmethyl)-2-thioxo-1,2,3,7-tetrahydro-6H-purin-6-one;
3-[(6-Phenoxypyridin-3-yl)methyl]-2-thioxo-1,2,3,7-tetrahydro-6H-purin-6-one;
3-{2-[(Quinolin-4-ylmethyl)amino]ethyl}-2-thioxo-1,2,3,7-tetrahydro-6H-purin-6-one;
3-(2-{[(1-Methyl-1H-indol-3-yl)methyl]amino}ethyl)-2-thioxo-1,2,3,7-tetrahydro-6H-purin-6-one;
3-{2-[Methyl(quinolin-4-ylmethyl)amino]ethyl}-2-thioxo-1,2,3,7-tetrahydro-6H-purin-6-one;
3-(2-Aminopropyl)-2-thioxo-1,2,3,7-tetrahydro-6H-purin-6-one trifluoroacetate;
3-{2-[(Pyridin-2-ylmethyl)amino]propyl}-2-thioxo-1,2,3,7-tetrahydro-6H-purin-6-one trifluoroacetate;
3-{2-[(Pyridin-3-ylmethyl)amino]propyl}-2-thioxo-1,2,3,7-tetrahydro-6H-purin-6-one;
3-{2-[(Pyridin-4-ylmethyl)amino]propyl}-2-thioxo-1,2,3,7-tetrahydro-6H-purin-6-one;
3-(2-{[(6-Chloropyridin-3-yl)methyl]amino}propyl)-2-thioxo-1,2,3,7-tetrahydro-6H-purin-6-one trifluoroacetate;
3-[2-({[6-(Trifluoromethyl)pyridin-3-yl]methyl}amino)propyl]-2-thioxo-1,2,3,7-tetrahydro-6H-purin-6-one trifluoroacetate;
3-(2-{[(4,6-Dichloropyrimidin-5-yl)methyl]amino}propyl)-2-thioxo-1,2,3,7-tetrahydro-6H-purin-6-one;
3-[2-({[2-(Dimethylamino)pyrimidin-5-yl]methyl}amino)propyl]-2-thioxo-1,2,3,7-tetrahydro-6H-purin-6-one;
3-{2-[(Quinolin-2-ylmethyl)amino]propyl}-2-thioxo-1,2,3,7-tetrahydro-6H-purin-6-one trifluoroacetate;
3-{2-[(Quinolin-3-ylmethyl)amino]propyl}-2-thioxo-1,2,3,7-tetrahydro-6H-purin-6-one;
3-(2-{[(1-tert-Butyl-3,5-dimethyl-1H-pyrazol-4-yl)methyl]amino}propyl)-2-thioxo-1,2,3,7-tetrahydro-6H-purin-6-one;
3-[2-({[1-(1,1-Dioxidotetrahydro-3-thienyl)-3,5-dimethyl-1H-pyrazol-4-yl]methyl}amino)propyl]-2-thioxo-1,2,3,7-tetrahydro-6H-purin-6-one;
3-{2-[(1H-Benzoimidazol-2-ylmethyl)amino]propyl}-2-thioxo-1,2,3,7-tetrahydro-6H-purin-6-one;
3-[2-({[1-(Phenylsulfonyl)-1H-pyrrol-2-yl]methyl}amino]propyl]-2-thioxo-1,2,3,7-tetrahydro-6H-purin-6-one trifluoroacetate;
3-{2-[({1-[(4-methylphenyl)sulfonyl]-1H-pyrrol-2-yl}methyl)amino]propyl}-2-thioxo-1,2,3,7-tetrahydro-6H-purin-6-one trifluoroacetate;
3-(2-{[(1-methyl-1H-pyrrol-2-yl)methyl]amino}propyl)-2-thioxo-1,2,3,7-tetrahydro-6H-purin-6-one;
3-[2-({[1-(4-sec-Butylphenyl)-1H-pyrrol-2-yl]methyl}amino)propyl]-2-thioxo-1,2,3,7-tetrahydro-6H-purin-6-one;
3-[2-({[1-(3-Methoxyphenyl)-1H-pyrrol-2-yl]methyl}amino)propyl]-2-thioxo-1,2,3,7-tetrahydro-6H-purin-6-one;
3-[2-({[2,5-Dimethyl-1-(1,3-thiazol-2-yl)-1H-pyrrol-3-yl]methyl}amino)propyl]-2-thioxo-1,2,3,7-tetrahydro-6H-purin-6-one;
3-[2-({[4-(3-Chlorobenzoyl)-1-methyl-1H-pyrrol-2-yl]methyl}amino)propyl]-2-thioxo-1,2,3,7-tetrahydro-6H-purin-6-one;
3-{2-[(1H-Imidazol-2-ylmethyl)amino]propyl}-2-thioxo-1,2,3,7-tetrahydro-6H-purin-6-one;
3-(2-{[(1-Methyl-1H-imidazol-2-yl)methyl]amino}propyl)-2-thioxo-1,2,3,7-tetrahydro-6H-purin-6-one;
3-(2-{[(4-Bromo-1-methyl-1H-imidazol-5-yl)methyl]amino}propyl)-2-thioxo-1,2,3,7-tetrahydro-6H-purin-6-one;
3-(2-{[(1-Methyl-1H-indol-3-yl)methyl]amino}propyl)-2-thioxo-1,2,3,7-tetrahydro-6H-purin-6-one;
2-Thioxo-3-{2-[(1H-1,2,3-triazol-5-ylmethyl)amino]propyl}-1,2,3,7-tetrahydro-6H-purin-6-one;
3-[2-({[1-(Benzyloxy)-1H-imidazol-2-yl]methyl}amino)propyl]-2-thioxo-1,2,3,7-tetrahydro-6H-purin-6-one;
3-(2-{[(6-Bromo-2-methylimidazo[1,2-a]pyridin-3-yl)methyl]amino}propyl)-2-thioxo-1,2,3,7-tetrahydro-6H-purin-6-one;
3-{2-[({1-[2-(2-Methoxyphenoxy)ethyl]-1H-pyrrol-2-yl}methyl)amino]propyl]-2-thioxo-1,2,3,7-tetrahydro-6H-purin-6-one;
N-[1-Methyl-2-(6-oxo-2-thioxo-1,2,6,7-tetrahydro-3H-purin-3-yl)ethyl]pyridine-2-carboxamide;
N-[1-Methyl-2-(6-oxo-2-thioxo-1,2,6,7-tetrahydro-3H-purin-3-yl)ethyl]nicotinamide;
N-[1-Methyl-2-(6-oxo-2-thioxo-1,2,6,7-tetrahydro-3H-purin-3-yl)-ethyl] isonicotinamide;
N-[1-methyl-2-(6-oxo-2-thioxo-1,2,6,7-tetrahydro-3H-purin-3-yl)ethyl]-1,8-naphthyridine-2-carboxamide;
N-[1-Methyl-2-(6-oxo-2-thioxo-1,2,6,7-tetrahydro-3H-purin-3-yl)ethyl]quinoline-2-carboxamide;
N-[1-Methyl-2-(6-oxo-2-thioxo-1,2,6,7-tetrahydro-3H-purin-3-yl)ethyl]pyrimidine-2-carboxamide; and
N-[1-Methyl-2-(6-oxo-2-thioxo-1,2,6,7-tetrahydro-3H-purin-3-yl)ethyl]-1H-imidazole-2-carboxamide trifluoroaceate;

or a pharmaceutically acceptable salt thereof.

7. A pharmaceutical composition comprising a compound according to claim 6, or a pharmaceutically acceptable salt thereof, optionally in admixture with a pharmaceutically acceptable adjuvant, diluent or carrier.

* * * * *